(12) United States Patent
George et al.

(10) Patent No.: US 11,066,707 B2
(45) Date of Patent: Jul. 20, 2021

(54) DETECTION OF TARGET NUCLEIC ACID VARIANTS

(71) Applicant: SAGA DIAGNOSTICS AB, Lund (SE)

(72) Inventors: Anthony Miles George, Lund (SE); Lao Hayamizu Saal, Lund (SE)

(73) Assignee: SAGA DIAGNOSTICS AB, Lund (SE)

( * ) Notice: Subject to any disclaimer, the term of this patent is extended or adjusted under 35 U.S.C. 154(b) by 250 days.

(21) Appl. No.: 15/572,023

(22) PCT Filed: May 18, 2016

(86) PCT No.: PCT/EP2016/061121
§ 371 (c)(1),
(2) Date: Nov. 6, 2017

(87) PCT Pub. No.: WO2016/184902
PCT Pub. Date: Nov. 24, 2016

(65) Prior Publication Data
US 2018/0340230 A1    Nov. 29, 2018

(30) Foreign Application Priority Data

May 18, 2015   (SE) .................................. 1550629-8

(51) Int. Cl.
*C12Q 1/68* (2018.01)
*C12Q 1/6886* (2018.01)
*C12Q 1/686* (2018.01)

(52) U.S. Cl.
CPC ........... *C12Q 1/6886* (2013.01); *C12Q 1/686* (2013.01); *C12Q 2527/107* (2013.01); *C12Q 2531/107* (2013.01); *C12Q 2563/159* (2013.01); *C12Q 2600/112* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 3,996,345 A | 12/1976 | Ullman et al. | |
| 4,351,760 A | 9/1982 | Khanna et al. | |
| 6,326,145 B1 | 12/2001 | Whitcombe et al. | |
| 6,548,254 B2 | 4/2003 | Beckman et al. | |
| 7,622,280 B2 | 11/2009 | Holliger et al. | |
| 2004/0023207 A1* | 2/2004 | Polansky | A61K 31/00 435/5 |
| 2010/0221702 A1* | 9/2010 | Moser | C12Q 1/6827 435/5 |
| 2011/0097764 A1* | 4/2011 | Johnson | C12Q 1/6853 435/91.21 |
| 2012/0164652 A1 | 6/2012 | Clemens et al. | |
| 2012/0316074 A1* | 12/2012 | Saxonov | C12N 15/10 506/2 |
| 2014/0178889 A1* | 6/2014 | Do | C12Q 1/686 435/6.12 |

FOREIGN PATENT DOCUMENTS

| | | | |
|---|---|---|---|
| WO | 03/054233 A1 | 7/2003 | |
| WO | 03/072809 A1 | 9/2003 | |
| WO | 2006/094360 A1 | 9/2006 | |
| WO | 2009/017784 A2 | 2/2009 | |
| WO | 2010/036352 A1 | 4/2010 | |
| WO | WO-2012033875 A2 * | 3/2012 | ........... C12Q 1/6858 |
| WO | 2012/075231 A1 | 6/2012 | |
| WO | 2015/058176 A1 | 4/2015 | |

OTHER PUBLICATIONS

Osterback R, Tevaluoto T, Ylinen T, Peltola V, Susi P, Hyypiä T, Waris M. Simultaneous detection and differentiation of human rhino- and enteroviruses in clinical specimens by real-time PCR with locked nucleic Acid probes. J Clin Microbiol. Dec. 2013; 51(12): 3960-7. Epub Sep. 18, 2013. (Year: 2013).*

Mouritzen P, Nielsen AT, Pfundheller HM, Choleva Y, Kongsbak L, Møller S. Single nucleotide polymorphism genotyping using locked nucleic acid (LNA). Expert Rev Mol Diagn. Jan. 2003; 3(1):27-38. (Year: 2003).*

Milbury CA, Zhong Q, Lin J, Williams M, Olson J, Link DR, Hutchison B. Determining lower limits of detection of digital PCR assays for cancer-relatedvgene mutations. Biomol Detect Quantif. Aug. 20, 2014; b1(1):8-22. eCollection Sep. 2014 (Year: 2014).*

Taly et al. Multiplex picodroplet digital PCR to detect KRAS mutations in circulating DNA from the plasma of colorectal cancer patients. Clin Chem. Dec. 2013; 59(12):1722-31. Epub Aug. 12, 2013. (Year: 2013).*

Hindson, B.J., et al., "High-Throughput Droplet Digital PCR System for Absolute Quantitation of DNA Copy Number" Anal. Chem. (2011) 83:8604-8610.

Miotke, L., et al., "High sensitivity detection and quantitation of DNA copy number and single nucleotide variants with single color droplet digital PCR" Anal. Chem. (2014) 86(5):2618-24.

Sanchez, J.A., et al., "Two-temperature LATE-PCR endpoint genotyping" BMC Biotechnology (2006) 6:44.

Zhou, W., et al., "Counting alleles to predict recurrence of early-stage colorectal cancers" Lancet (2002) 359 (9302):219-25.

Zhu, G., et al., "Highly Sensitive Droplet Digital PCR Method for Detection of EGFR-Activating Mutations in Plasma Cell-Free DNA from Patients with Advanced Non-Small Cell Lung Cancer" J. Mol. Diagn. (2015) 17:265e272.

Chang, H.W., et al., "Digital single-nucleotide polymorphism analysis for allelic imbalance" Methods Mol. Med. (2005) 103:137-41.

(Continued)

*Primary Examiner* — Teresa E Strzelecka
*Assistant Examiner* — Olayinka A Oyeyemi
(74) *Attorney, Agent, or Firm* — Robert C. Netter, Jr.; Dann, Dorfman, Herrell & Skillman

(57) ABSTRACT

The present invention relates to highly sensitive and specific methods for detection of nucleic acids, which for example are useful for detection of rare mutations, or for detection of low-abundance variants in nucleic acids sequences. The methods involve an asymmetric incremental polymerase reaction (AIPR) followed by an exponential polymerase chain reaction (PCR).

13 Claims, 22 Drawing Sheets

Specification includes a Sequence Listing.

(56) References Cited

OTHER PUBLICATIONS

Breslauer, K.J., et al., "Predicting DNA duplex stability from the base sequence" Proc. Natl. Acad. Sci. (1986) 83 (11):3746-50.
Brown, E.L., "Chemical synthesis and cloning of a tyrosine tRNA gene" Methods Enzymol. (1979) 68:109-51.
Heid, C.A., et al., "Real time quantitative PCR" Genome Res. (1996) 6(10):986-94.
Leone, G., et al., "Molecular beacon probes combined with amplification by NASBA enable homogeneous, real-time detection of RNA" Nucleic Acids Res. (1998) 26(9):2150-5.
Whitcombe, D., et al., "Detection of PCR products using self-probing amplicons and fluorescence" Nat. Biotechnol. (1999) 17(8): 804-7.
Tyagi, S., et al., "Multicolor molecular beacons for allele discrimination" Nat. Biotechnol. (1998) 16(1):49-53.
Tyagi, S., et al., "Molecular beacons: probes that fluoresce upon hybridization" Nat. Biotechnol. (1996) 14(3):303-8.
Nazarenko, I.A., et al., "A closed tube format for amplification and detection of DNA based on energy transfer" Nucleic Acids Res. (1997) 25(12):2516-21.
Wu, P., et al., "Resonance energy transfer: methods and applications" Anal. Biochem. (1994) 218(1):1-13.
Milbury, C.A., et al., "PCR-based methods for the enrichment of minority alleles and mutations" Clin. Chem. (2009) 55(4):632-40.
Narang, S.A., et al., "Improved phosphotriester method for the synthesis of gene fragments" Methods Enzymol. (1979) 68:90-8.
Clegg, R.M., "Fluorescence resonance energy transfer and nucleic acids" Methods Enzymol. (1992) 211:353-88.

\* cited by examiner

PIK3CA c.3140A>G (H1047R)

```
       5'                        Primer-H
       AAGACCCTAGCCTTAGATAAAACTGAGCAAGA
(+) GAAAGACCCTAGCCTTAGATAAAACTGAGCAAGA
(-) CTTTCTGGGATCGGAATCTATTTTGACTCGTTCT Primer-H                        3'
    GGCTTTGGAGTATTTCATGAAACAAATG
    GGCTTTGGAGTATTTCATGAAACAAATGAATGAT
    CCGAAACCTCATAAAGTACTTTGTTTACTTACTA GCACATCATGGTGGCTGGACAACAAAAATGGA
    CGTGTAGTACCACCGACCTGTTGTTTTACCT
    CGTGCAGTACCACCGACCTGTTGTTTTAC
    CGTGTAGTACCACC                    Primer-L  5'
    3'                  5'
    ─MUT Probe (FAM)
    ─WT Probe (HEX)
```

Fig. 2

PIK3CA c.1624G>A (E542K)

```
                                              WT Probe (HEX)┐
                                              MUT Probe (FAM)┤
                                          5'                3'
       5'   Primer-L    3'              CT CT GA A A T CA CT GA G
       CT AC AC GA GA TC                TCT CT A A A A T CA CT GA
(+) T T CT A CA CGA GA T CCT CT CT CT GA A A T CA CT GA G CA GGA
(-) A A GA T GT GCT CT A GGA GA GA GA C T T T A GT GA CT CGT CCT GA A A GA T T T T CT A T GGA GT CA CA GGT A A GT GCT A A A A T
       CT T T CT A A A A GA T A CCT CA GT GT CCA T T CA CGA T T T T A
                    GA T A CCT CA GT GT CCA T T CA CGA T T T T A
                    3'                     Primer-H GGA GA T T CT CT GT T T CT T T T T CT T T A T T A CA GA A
       CCT CT A A GA GA CA A A GA A A A A GA A A T A A T GT CT T
       CCT CT A A GA GA CA A A GA A A A A GA A A T A A T GT C
                    Primer-H                                  5'
```

Fig. 2 - Continued

```
                                    5' CTGAGCAAGAGGCTTT

5' TAGCCTTAGATAAAACTGAGCAAGAGGCTTT (+) strand CCTAGCCTTAGATAAAACTGAGCAAGAGGCTTT
(-) strand GGATCGGAATCTATTTTGACTCGTTCTCCGAAA GGAGTATTTCATGAAACAAATG                    Primer-H (beta1)

GGAGTATTTCATGAAACAAATGAATGATG             Primer-H (beta2)

GGAGTATTTCATGAAACAAATGAATGATGCACATCATGGTGG
CCTCATAAGTACTTTGTTTACTTACTACGTGTAGTACC

MUT Probe (FAM)  ACGTGCAGTACCACC
                                        3'             5'
                       WT Probe (HEX)   ACGTGTAGTACCACC
                                        3'             5'

CTGGACAACAAAAATGGATTGGATC (+) strand
GACCTGTTGTTTTACCTAACCTAG  (-) strand

GTTGTTTTACCTAACCT
     3'     Primer-L     5'
```

Fig. 4

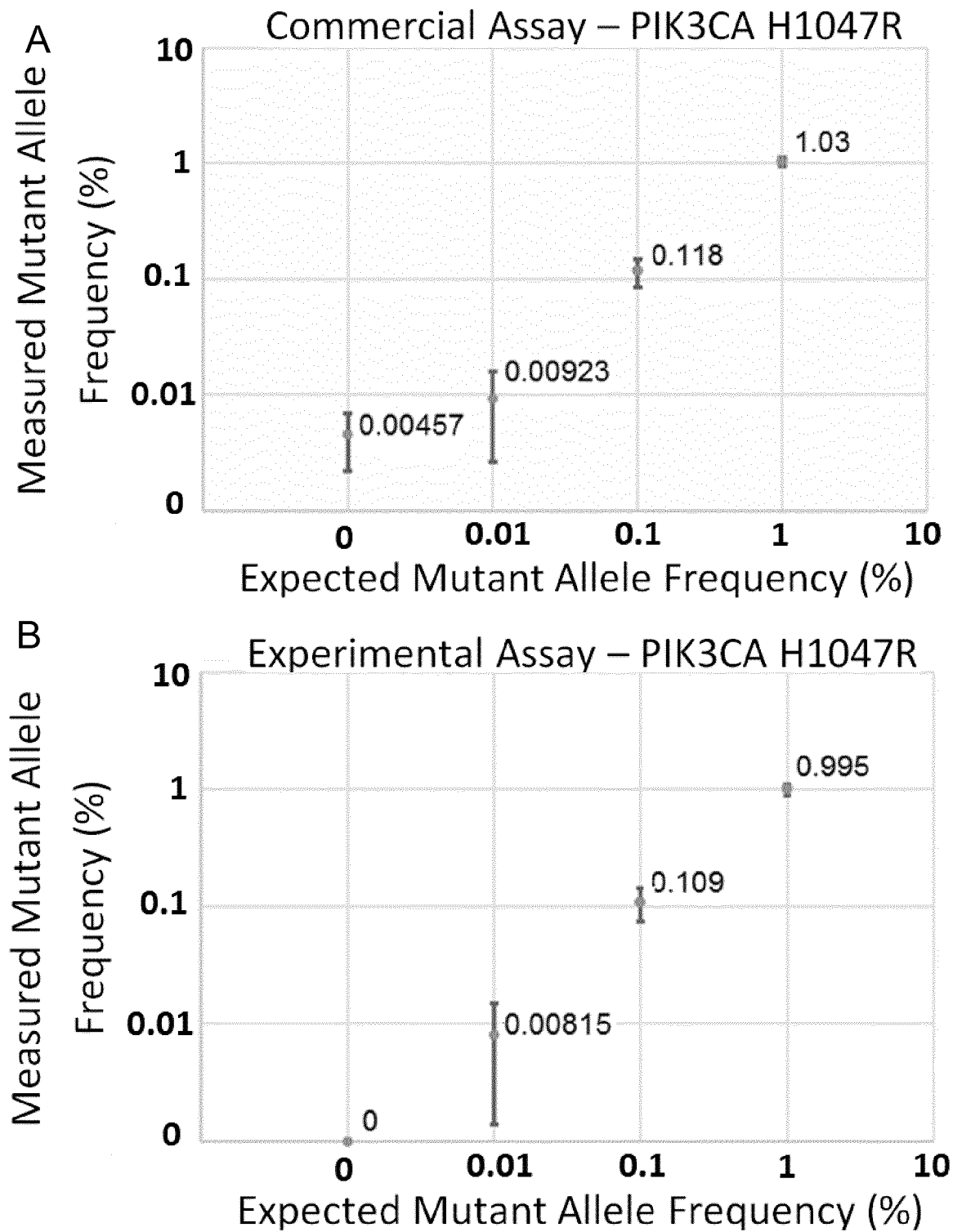
Fig. 6A-B

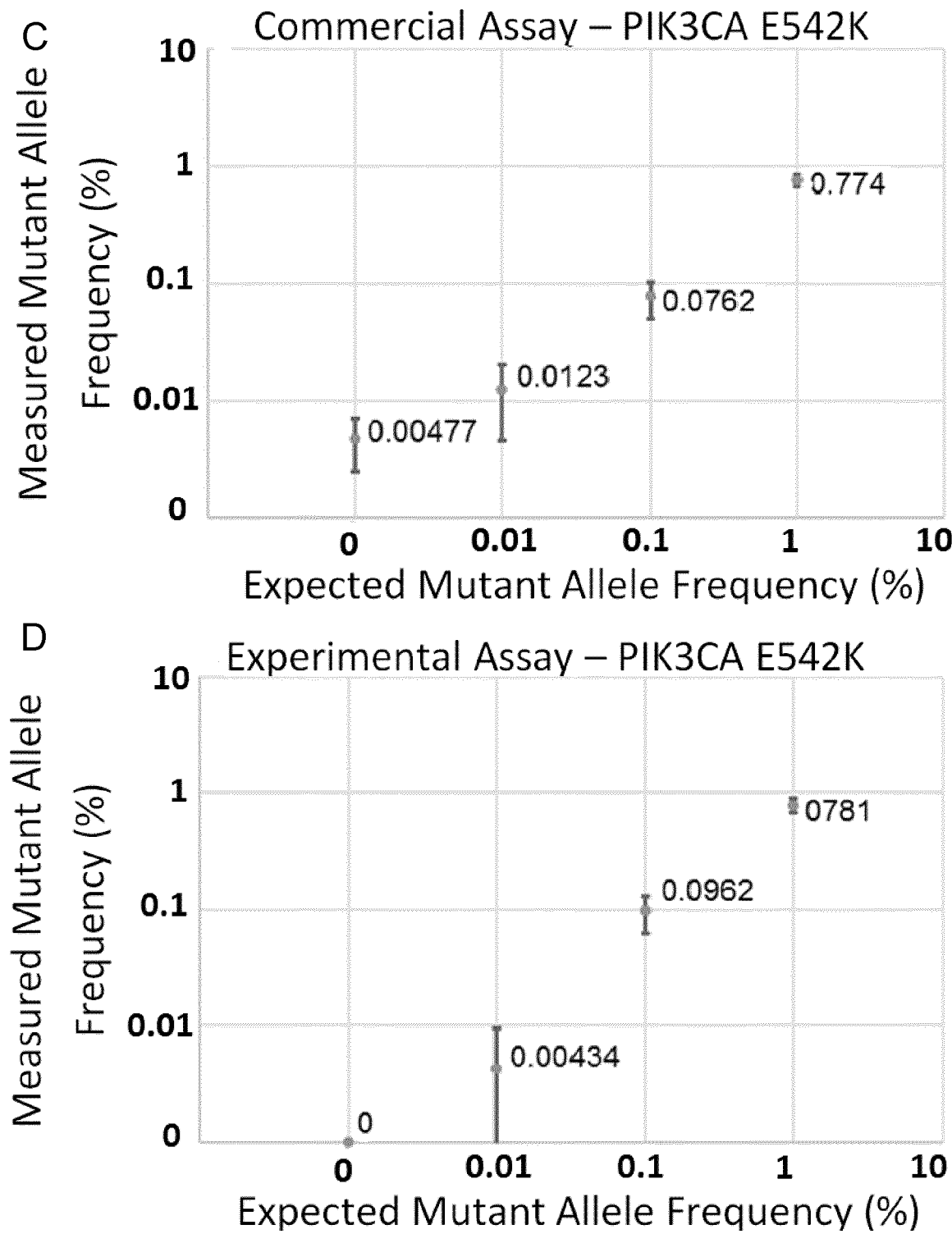
Fig. 6C-D

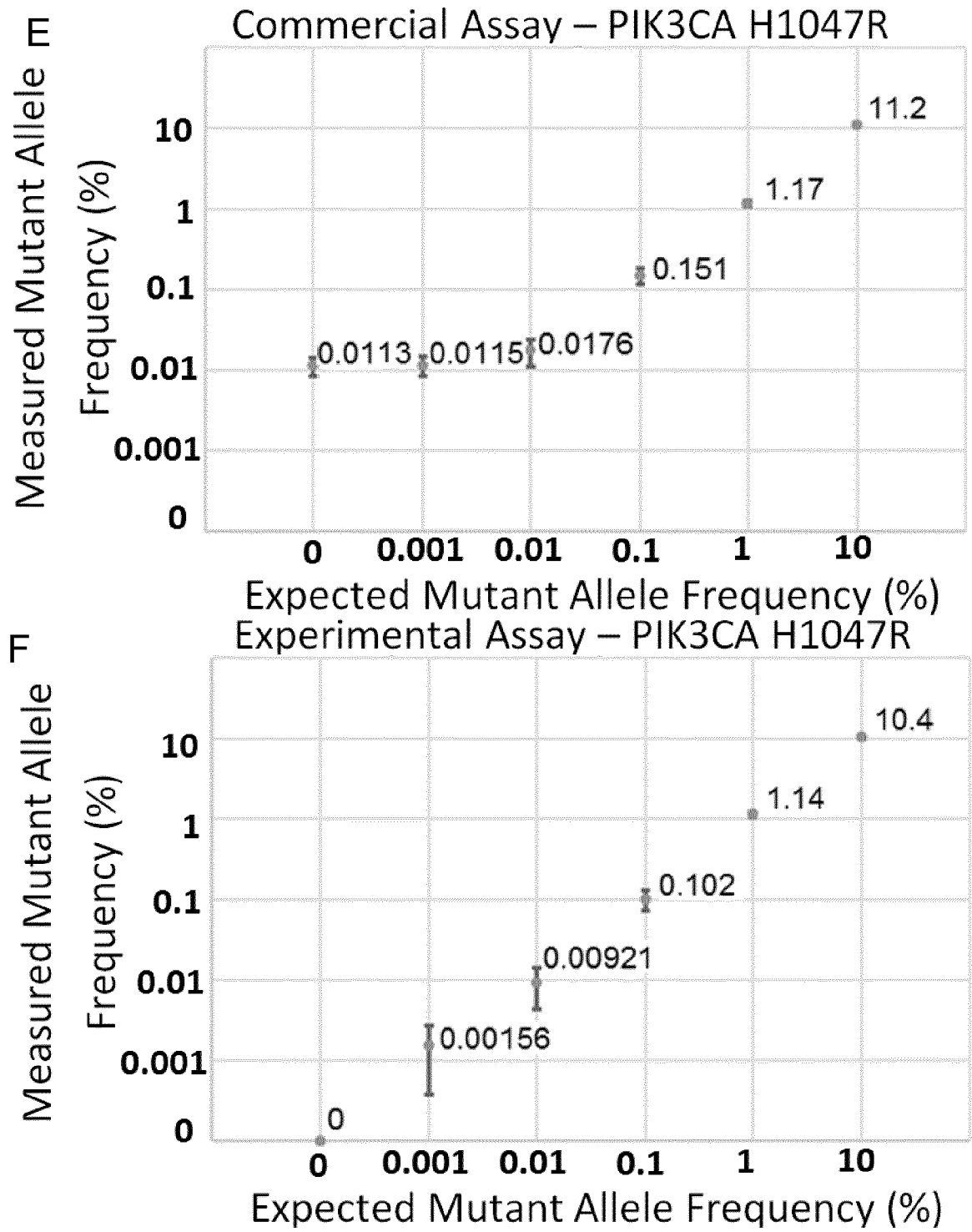
Fig. 6E-F

"mismatch modified primer-L"

mismatched   matched
nucleotides  nucleotides

5' CCTCAAACTTGTGGTAG 3'

(+) strand  ATGACTGAATATAAACTTGTGGTAGTTGGAG
(-) strand  TACTGACTTATATTTGAACACCATCAACCTC 5' CTGGTGGCGTAGG 3'     WT Probe (HEX)

5' CTGGTGACGTAGGCAA 3'  MUT Probe (FAM)

CTGGTGGCGTAGGCAAGAGTGCCTTGACGATACAGCTAA
GACCACCGCATCCGTTCTCACGGAACTGCTATGTCGATT
                     CTCGCGGAACTGCTATGTCGATT
           3'              Primer-H

TTCAGAATCATTTTGTGGACGAATATGATCCAACAAT
AAGTCTTAGTAAAACACCTGCTTATACTAGGTTGTTA

AAGTCTTAGTAAAACACCTGCTTATACTAGGTTGTTA
           Primer-H                  5'

Fig. 7A

DETECTION OF TARGET NUCLEIC ACID VARIANTS

This application is a § 371 application of PCT/EP2016/061121, filed May 18, 2016, which in turn claims priority to SE Application 1550629-8, filed May 18, 2015. The entire disclosure of each of the foregoing applications is incorporated by reference herein.

Incorporated herein by reference in its entirety is the Sequence Listing being concurrently submitted via EFS-Web as a text file named SeqList.txt, created Nov. 2, 2017, and having a size of 27,193 bytes.

FIELD OF INVENTION

The present invention relates to the field of methods for detection of nucleic acids. The methods of the invention are highly sensitive and specific and are thus for example useful for detection of rare mutations, or for detection of low-abundance variants in nucleic acids sequences.

BACKGROUND OF INVENTION

Detection of nucleic acids present in very low quantities and/or at low frequency is desirable for many applications. Detection of gene mutations is for example important for a myriad of diseases, such as cystic fibrosis, sickle cell anemia, and cancers. It is increasingly being recognized that exceptionally sensitive and specific methods for mutation detection are necessary, in particular for low-input samples such as circulating tumor DNA (ctDNA) and analysis of single cells. Today's conventional methods can suffer from a constellation of issues, including a high requirement of input sample DNA quantity, high per-sample cost, complex and laborious workflows, insufficient sensitivity and/or specificity, and inability to detect low-abundance mutated DNA sequences within a high background of normal wild-type sequence (so-called mutant allele fraction; MAF). Nearly all mutation detection methods rely on DNA amplification using the polymerase chain-reaction (PCR) to copy, exponentially, the target DNA regions of interest using a DNA polymerase enzyme.

When the purpose is to discriminate between normal wild-type sequence and a variant (mutant) sequence which may differ by as little as only one single nucleotide base, the fidelity of the DNA polymerase enzyme can become a significant limitation to discriminatory power (affecting most measures of mutation detection performance). Every polymerase enzyme has some rate of base incorporation error for each possible incorrect base change, typically in the range of 0.5 to 300 errors per million base pairs amplified (i.e., $5 \times 10^{-7}$ to $3 \times 10^{-4}$). For many applications, these single-base polymerase base incorporation errors are tolerable. For example, if vast quantities of DNA are available and the MAF is moderate to high, e.g. >10-20%, an ordinary PCR may be sufficient. However, in applications involving the detection of low-abundance variants, there is a need for ultra-sensitive detection methods so that a true-positive mutation can be discriminated from a false-positive induced by polymerase error. Current mutation detection assays have detection limits of 10-20% MAF (Sanger sequencing), 5-10% MAF (pyrosequencing), 1-5% MAF (next-generation sequencing), and 0.1% MAF (digital PCR, COLD-PCR, ultra-deep next-generation sequencing).

Digital PCR is a method that partitions a PCR reaction into many smaller individual reactions so that each reaction partition contains zero to only a very few target sequence molecules. The partitioning of all molecules is random and follows a Poisson distribution. The partitioning transforms the situation of an extremely low relative abundance of a rare variant sequence among an abundance of wild-type sequence, to a situation where most partitions have only wild-type sequence and some partitions have a very high relative abundance of the rare variant sequence compared to wild-type sequence. The result is an increase in sensitivity for rare variant sequence detection through the diluting away of the wild-type sequence within each partition. However, polymerase error is still a significant problem even for digital PCR that can lead to false-positives, thus negatively impacting the discriminatory performance and detection limits.

Different PCR-based methods for enrichment and detection of minority alleles and mutations have been described e.g. by Milbury et al., Clin Chem. 2009 April; 55(4): 632-640, however none of these methods are extremely sensitive and easy to perform.

SUMMARY OF INVENTION

There is thus an unmet need for extremely sensitive methods for detecting low-abundance nucleic acids with a very low frequency of false positives.

The inventors found that in methods employing standard PCR, the error rates of the DNA polymerase create a performance barrier to the limit of detection, because as DNA is exponentially amplified to numbers in the billions of copies, errors are randomly introduced into many DNA copies, including falsely generating the sequence variants of interest, and these errors are copied and amplified.

The maximum achievable sensitivity in a standard digital PCR assay is also limited by the fidelity of the polymerase enzyme used in the reaction. When a wild-type sequence is copied incorrectly by polymerase, this may create a copy carrying a false mutant sequence, and such a reaction can be read as positive for the mutant target sequence. Depending on how many PCR cycles are performed and at which cycle the false mutant sequence is introduced, the signal can be indistinguishable from that of a true-positive and it will therefore be read as a false-positive. If this polymerase error event occurs during a late PCR cycle, true-positive signals will have already gained a "head-start" on the potential false-positive signals and there may be a possibility to distinguish between the true-positives and false-positives.

The methods of the invention reliably give true-positive reactions a consistent signal advantage over any potential false-positive reactions.

Thus, the invention provides a method that is able to counteract the consequences of polymerase errors to increase assay performance by at least an order of magnitude. The methods of the invention achieve exceedingly high sensitivity and specificity, have a simple workflow and are relatively inexpensive.

The present invention provides extremely sensitive methods for detecting low-abundance nucleic acids with a very low frequency of false positives. The methods of the invention generally consist of an asymmetric incremental polymerase reaction (AIPR) stage using a high annealing temperature, followed by a more conventional symmetric PCR stage using a lower annealing temperature, both performed within partitioned reactions such as droplet digital PCR.

Methods for amplifying nucleic acids using PCR based assays using primers with different melting temperatures (Tm) are known in the art. WO2006/094360 for example describes a single closed-tube PCR, wherein two sequential symmetric PCRs are performed. In a first round a nucleic acid at a locus of interest is specifically amplified using tagged locus-specific primers suitable for performing exhaustive PCR. In a second round, the first round amplification product is then amplified using tag primers having lower Tm than the tagged locus-specific primers.

Due to the high sensitivity and specificity, the methods of the invention are useful for detection of low-abundance nucleic acid sequences. In particular, the methods are useful for detection of rare single-base variants among a hugely abundant wild-type allele, and are even useful when the total sample input quantity is low, as may be the case for circulating tumour DNA (ctDNA) in patient blood plasma.

The methods of the invention generally consist of an asymmetric incremental polymerase reaction (AIPR) stage followed by a more conventional symmetric PCR stage. In the AIPR stage in general only one strand of the target nucleic acid sequence is copied, which gives rise to a plurality of templates for the conventional symmetric PCR. Thus, whereas a conventional PCR in principle is exponential amplification, then AIPR in principle is linear amplification. For amplification of any given target sequence of interest, at least two primers are designed flanking the sequence of interest such that one primer (termed here a "primer-H") has a very high melting temperature (Tm) and another primer on the opposite strand and orientation, has a much lower Tm ("primer-L"). The two stages (AIPR and PCR) differ in the thermocycling conditions and the primers that are functionally active during each stage.

In the AIPR stage, the target single-strand sequence is copied by the polymerase which is primed using the primer-H oligonucleotide complementary to one end of the target sequence of interest and only a single copy (e.g. the sequence complementary to the template) is synthesized per thermal cycle. This is generally accomplished by thermal cycling to 1) a temperature to denature the DNA into single-stranded molecules; 2) to a temperature that is permissible for annealing of the primer-H to prime monodirectional copying of the target sequence of interest by a DNA polymerase, but the temperature not permissible for annealing of primer-L; 3) to a temperature to allow extension of the synthesized strand by a DNA polymerase but at which primer-L still cannot anneal; 4) repeat steps 1 to 3 in repeated cycles as needed, with one additional complementary copy synthesized per cycle that is primed and extended from primer-H. The synthesized copy is the Watson-Crick complement to the single-strand sequence to which the primer-H anneals and thus each synthesized copy does not become a template for further amplification during any thermal cycles of the AIPR stage. Several to very many rounds of AIPR copying only in a single direction are performed by cycling as above the thermal conditions where only the mono-directional primer-H is able to anneal and extend to synthesize a nucleic acid strand. Therefore, from each original single-strand template and for each thermal cycle, a single complementary target sequence is generated such that, for example, after X-number of asymmetric cycles run, there will be X new complementary DNA molecules at the end of the stage for every Y-number of single-strand starting template molecules in the partition (the total number of new complementary DNA molecules in the reaction partition will therefore be X*Y). For example, after 64 cycles with only 1 single-strand target template in the reaction partition, there will be the 1 single-strand template plus 1*64=64 complementary copies in the partition. With a very high probability, the vast majority of these new molecules will be an exact complementary copy of the original template molecule, as the polymerase error rate is low (0.5 to 300 errors per million basepairs amplified) and only e.g. 64 copies of several dozen to several thousands basepairs length each are synthesized. Even in the event that a polymerase error occurred during one of these AIPR cycles in a reaction partition that contained only 1 wild-type target sequence molecule and 0 mutant target sequences to begin with, of the 64 new DNA molecules, only 1 would be mutant among 63 non-mutant. This error-induced mutant target sequence would be potentially problematic if it occurred at the exact sequence position of highest interest, but may not be problematic if it occurred at another position. Conversely, in a true-positive reaction partition that started with 1 true mutant target sequence molecule and 0 wild-type targets, there would be 64 new mutant containing DNA molecules, and exceedingly rarely, 63 new mutant containing molecules and 1 falsely-wild-type molecule. Thus, in a digital PCR reaction, the true-positive reaction partitions would have 62 to 64 additional mutant target molecules than the rarely occurring partition that now contains a false-positive mutant sequence due to polymerase error. After this AIPR stage, the conventional symmetric PCR stage begins and the true-positive reaction partitions have the equivalent of approximately $\log_2(X)$ cycles "head-start" in terms of molecular copies over false-positive reaction partitions. In other words, in the example above with X=64 asymmetric cycles, the true-positive reaction partitions will have approximately $\log_2(64)=6$ cycles head-start.

In a digital PCR system using quenched fluorescent probes, complementary to the target sequence of interest, that anneals to its target sequence and whose fluorophore is cleaved and thus unquenched by the exonuclease activity of a polymerase, the released fluorophores accumulate in the partition and increases its fluorescent signal. The conventional PCR is continued until the true-positive signal is discernible and the false-positive signal is still lagging behind by a number of cycles. A threshold is made to separate the two signals. Other methods for detecting the product of the conventional PCR may also be used.

FIG. 1 provides an overview of the method according to one embodiment of the invention.

One way to achieve single-directional copying of only one template strand during the asymmetric stage while avoiding opposite direction (opposite strand) copying is to only include a single primer during the AIPR stage and adding the second primer at the start of the symmetric PCR stage. Most partition-based digital PCR methods, however, do not currently permit the addition of reagents once the partitioning has occurred, for example it is difficult to add reactants into reaction droplets in droplet digital PCR (ddPCR).

In one embodiment the present invention provides a method for assay design that produces primers that allow for AIPR with both primers present in the reaction by utilizing primer pairs with greatly different melting temperatures. A high-Tm primer (primer-H) is designed for one strand at the end of the target sequence of interest and a low-Tm (primer-L) is designed for the other strand at the other end of the target sequence of interest. The methods also include means for detecting specific alleles. Said means may for example be allele-specific probes positioned over a variant base. The AIPR stage is run at a very high temperature where the high-Tm primer-H is able to anneal efficiently and the low-Tm primer-L is not. The conventional symmetric PCR stage is run at a lower temperature where the low-Tm primer-L and high-Tm primer-H are able to efficiently bind to specific template. If the system uses allele specific probes, then these are preferably designed so that they bind at or near the lower annealing temperature. The Tm of the primers, and thus the activity during the two stages, can be manipulated by primer length, introduction of designed sequence mismatches in the primer, and/or by primer modifications (e.g. by use of variant nucleotides, such as locked nucleic acid [LNA] bases, or other oligonucleotide modifications such as addition of minor groove binder [MGB]). It is critical that the primer-L activity is suppressed during the asymmetric AIPR stage because whenever low-Tm primer binding and extension does occur, there is symmetric copying of both strands, which increases the substrate for potential polymerase errors that will then be propagated during every subsequent cycle. Because of this, the preferred assay design in terms of false-positive avoidance is one in which the difference between the asymmetric stage annealing temperature and low-Tm primer melting temperature is high.

It is thus an aspect of the invention to provide methods for detection of the presence of a target nucleic acid sequence or detection of the presence of a variant sequence in a target nucleic acid sequence in a sample comprising the steps of
a) providing a sample comprising template nucleic acids
b) providing a set of primers comprising at least a pair of primers specifically capable of amplification of the target nucleic acid sequence, wherein the set of primers at least comprises a primer-H and a primer-L, wherein the melting temperature of primer-H is at least 15° C. higher than the melting temperature of primer-L, and wherein primer-L contains a sequence complementary to a fragment of the elongation product of primer-H,
c) providing a nucleic acid polymerase having polymerase activity at an elongation temperature,
d) preparing partitioned PCR reactions each comprising a part of the sample, the set of primers, the nucleic acid polymerase, PCR reagents and optionally detection reagents
e) performing an asymmetric incremental polymerase reaction (AIPR) comprising the steps of:
 i. incubating the partitioned PCR reactions at a denaturation temperature, thereby denaturing DNA to single-stranded molecules
 ii. incubating the partitioned PCR reactions at a high annealing temperature allowing annealing of primer-H, but not of primer-L,
 iii. optionally incubating the partitioned PCR reactions at the elongation temperature,
 iv. optionally repeating steps i to iii,
 v. thereby amplifying only one strand of the target nucleic acid sequence
f) performing a polymerase chain reaction (PCR) comprising the steps of:
 1) incubating the partitioned PCR reactions at a denaturation temperature, thereby denaturing DNA to single-stranded molecules
 2) incubating the PCR at a low annealing temperature allowing annealing of both primer-H and primer-L,
 3) incubating the PCR at the elongation temperature thereby allowing extension of all annealed primers
 4) optionally repeating steps II to IV,
 5) thereby amplifying both strands of the target nucleic acid sequence to obtain a PCR product
g) detecting whether the PCR product comprises the target nucleic acid sequence or the variant sequence in the target nucleic acid sequence.

DESCRIPTION OF DRAWINGS

FIG. 1 shows an overview of an IBSAFE method.

FIG. 2 shows two specific examples of assay designs for two target sequences of interest, both within the oncogene PIK3CA: the H1047R variant located at codon 3140 with nucleotide change of A to G (top), and the E542K variant located at codon 1624 with nucleotide change of G to A (bottom).

FIG. 4 shows an experimental Assay Design-Assay design targeting PIK3CA c.3140A>G (H1047R) with alternate versions of Primer-H (beta 1 and beta 2). Primer-H beta 1 is shorter and thus has a lower melting temperature than Primer-H beta 2. The probes used in this assay are custom TaqMan® MGB Probes (Applied Biosystems) containing a 5' reporter dye (FAM or HEX), a 3' nonfluorescent quencher, and a 3' minor groove binder attached to the quencher molecule.

FIG. 6 shows an example of limit of detection comparison-the measured mutant allele frequency for PrimePCR™ Mutation Assay (left side) and IBSAFE assays (right side) for PIK3CA H1047R variant (top panel and lower panel) and PIK3CA E542K variant (middle panel) are shown. Upper and middle panels show results from assays comprising template DNA comprising 0, 0.01, 0.1 and 1% mutant DNA (the remainder being wild type), whereas the lower panel shows results from assays comprising template DNA comprising 0, 0.001, 0.01, 0.1, 1 and 10% mutant DNA. The false-positive signals for the PrimePCR™ Mutation Assay indicate that the results at 0.01% MAF cannot be trusted (overlap with the negative control), and thus the lower limit of detection is 0.1%. In contrast, for IBSAFE assays, 0.01% MAF is reliable, and even at 0.001% the results are reliable. The lowest limit of detection has yet to be fully tested but is likely, depending on the assay, to be considerably less than 0.001%.

DETAILED DESCRIPTION OF THE INVENTION

Definitions

Figure 1A:
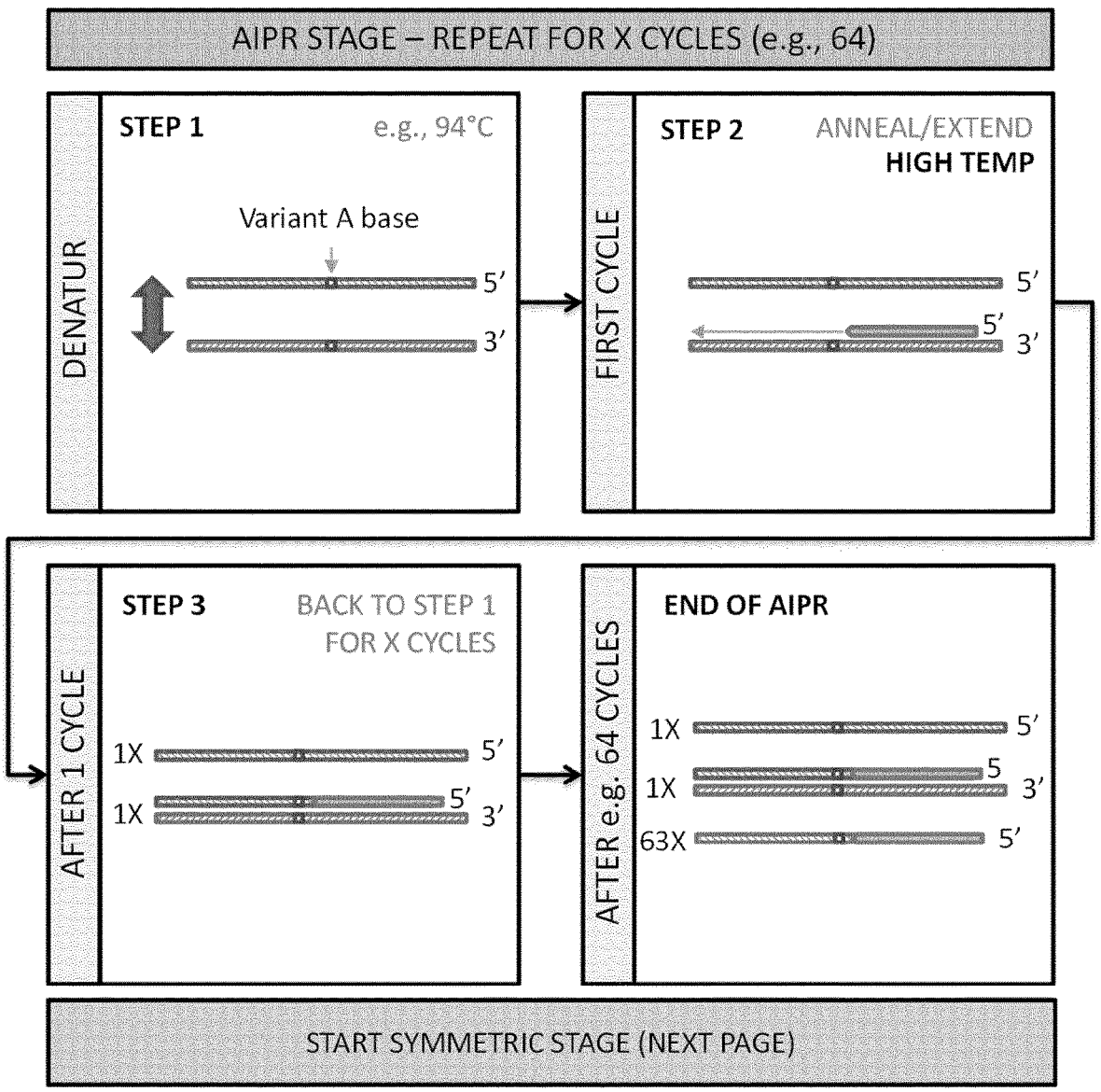
FIG. 1A shows the situation where a mutant template is present. During the AIPR stage complementary copies of the mutant sequence are generated. The temperature is kept sufficiently high so that the primer-L and the probes do not anneal. In the symmetric stage the mutant DNA is exponentially amplified.
Figure 1A:
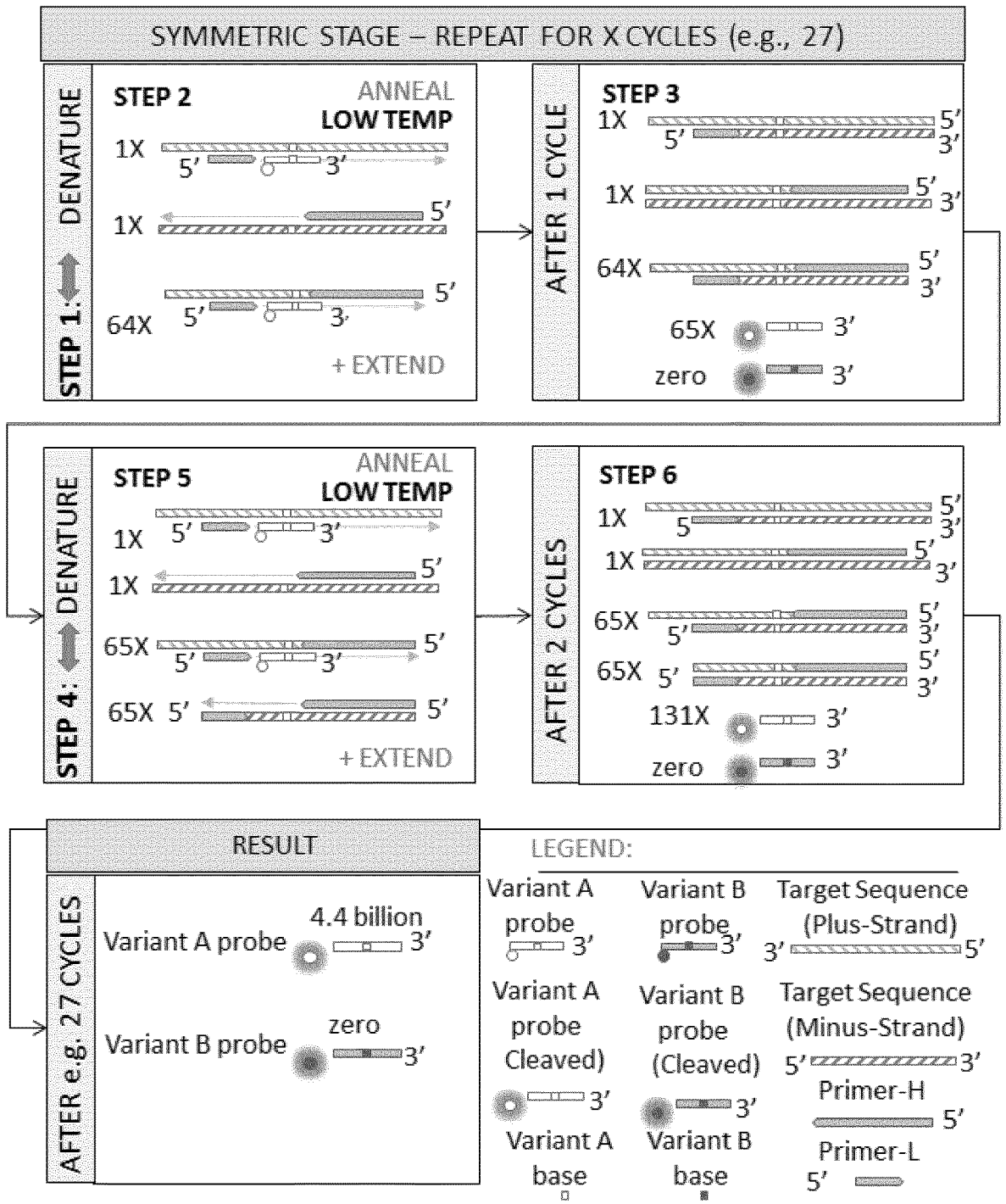

Amplification: Amplification of a nucleic acid is the generation of copies of said nucleic acid. The term "pair of primers capable of amplification of a target nucleic acid" as used herein refers to that if said pair of primers is added to a PCR together with the target nucleic acid, nucleotides and a nucleic acid polymerase, then said PCR will result in production of the target nucleic acid.

Approximately: The term approximately as used herein refers to +/−10%, preferably +/−5%, for example to +/−1%.

Denaturing temperature: The denaturing temperature is a temperature allowing denaturing all DNA molecules in the sample and/or in the PCR reactions and/or the AIPR to denature to single stranded molecules. The denaturing temperature is preferably sufficiently low to ensure that the nucleic acid polymerase is not permanently denatured. Typically, the denaturing temperature is a temperature in the range of 90 to 99° C., such as in the range of 92 to 97° C., for example in the range of 94 to 95° C.

Elongation temperature: The elongation temperature is a temperature allowing enzymatic activity of the nucleic acid polymerase. Typically a nucleic acid polymerase has activity over a temperature range, and thus the elongation temperature may be any temperature within that range. Most nucleic acid polymerases have a temperature optimum, but retain activity at other temperatures than the temperature optimum. In such cases, the elongation temperature may be any temperature where the nucleic acid polymerase has activity even if the temperature is not the optimum temperature. The term "nucleic acid polymerase having polymerase activity at an elongation temperature" as used herein refers to that the nucleic acid polymerase is capable of catalysing synthesis a new nucleic acid strand complementary to the template strand at the elongation temperature. In some embodiments of the invention the elongation temperature is near the melting temperature of the primer-H. Thus, a nucleic acid polymerase may be chosen, which has polymerase activity at a temperature near the melting temperature of primer-H and/or the primer-H may be designed to have a melting temperature near the elongation temperature. The term "near the temperature" as used in this connection may for example be within +/−5° C., such as +/−2° C., for example +/−1° C. of said temperature. Usually, the elongation temperature is in the range of 65 to 80° C., for example in the range of 68 to 75° C.

Melting temperature: The melting temperature of a primer is the temperature at which 50% of the primer forms a stable double helix with its complementary sequence and the other 50% is separated to single strand molecules. The melting temperature may also be referred to as $T_m$. Preferably, the Tm as used herein is calculated using a nearest-neighbor method based on the method described in Breslauer et al., Proc. Natl. Acad. Sci. 83, 3746-50 (1986) using a salt concentration parameter of 50 mM and primer concentration of 900 nM. For example, the method is implemented by the software "Multiple Primer Analyzer" from Life Technologies/Thermo Fisher Scientific Inc.

The term "pair of primers capable of amplification of a target nucleic acid" as used herein refers to that if said pair of primers is added to a PCR together with the target nucleic acid, nucleotides, nucleic acid polymerase, and other PCR reagents, then said PCR will result in production of the target nucleic acid. One of the primers of the pair of primers will be a forward primer, whereas the other will be a reverse primer. If primer-H is a forward primer, then preferably primer-L is a reverse primer and vice versa.

PCR reagents: PCR reagents are reagents which are added to a PCR in addition to nucleic acid polymerase, sample and set of primers. The PCR reagents at least comprise nucleotides. In additional the PCR reagents may comprise other compounds such as salt(s) and buffer(s).

Primer-H and primer-L: A primer-H is a primer having a high melting temperature, whereas primer-L is a primer having a low melting temperature.

Set of primers: A set primers contains two or more different primers. A set of primers contains at least a pair of primers specifically capable of amplification of a target nucleic acid. Furthermore, a set of primers according to the invention contains at least a primer-H and a primer-L. Thus, in embodiments of the invention, wherein the set of primers contains only two different primers, then set of primers contains a primer-H and a primer-L, wherein the primer-H and primer-L are capable of amplification of a target nucleic acid.

Target nucleic acid: Any nucleic acid sequence the presence of which is desirable to detect. The target nucleic acid may for example be a nucleic acid sequence associated with a clinical condition.

Method for Detection of a Variant Sequence or a Target Nucleic Acid

The present invention provides methods for detection of the presence of a variant sequence in a target nucleic acid in a sample.

Such methods may be useful for detecting whether a variant sequence is present in a sample, which may comprise a mixture of target nucleic acids wherein only a portion of the target nucleic acids may comprise the variant sequence. In particular, the methods are useful for detecting the presence of a variant sequence in a sample comprising target nucleic acids of which only a minor fraction may potentially comprise the variant sequence.

Said variant sequence may be any variant sequence which is desirable to detect. For example, the variant sequence may be associated with a clinical condition as described herein below in more detail in the section "Method of predicting the presence of a clinical condition". In particular, the variant sequence may be any of the variant sequences described below in the section "Variant sequence and target nucleic acid sequence".

The sample may be any sample in which it is desirable to detect, whether said variant sequence is present. For example if the variant sequence is indicative of a clinical condition, the sample may be a sample from an individual at risk of acquiring said clinical condition.

The present invention also provides methods for detection of the presence of a target nucleic acid sequence in a sample.

Such methods may be useful for detecting whether a target nucleic acid sequence is present in a sample. Said sample may comprise a mixture of template nucleic acids potentially comprising the target nucleic acid sequence. In particular, the methods are useful for detecting the presence of a target nucleic acid sequence in a sample, which potentially may comprise only a very low level of said target nucleic acid sequence.

Said target nucleic acid sequence may be any target nucleic acid sequence, which is desirable to detect. For example, the presence of the target nucleic acid sequence may be associated with a clinical condition as described herein below in the more detail in the section "Method of predicting the presence of a clinical condition". In particular, the target nucleic acid sequence may be any of the target nucleic acid sequences described below in the section "Variant sequence and target nucleic acid sequence".

The sample may be any sample in which it is desirable to detect, whether said target nucleic acid sequence is present. For example if the target nucleic acid sequence is indicative of a clinical condition, the sample may be a sample from an individual at risk of acquiring said clinical condition.

The methods of detecting the presence of a target nucleic acid sequence or the presence of a variant nucleic acid in a sample in general comprises the following steps:
a) providing a sample comprising template nucleic acids;
b) providing a set of primers which for example may be any of the sets of primers described herein below in the section "Set of primers",
c) providing a nucleic acid polymerase having polymerase activity at an elongation temperature, which for example may be any of the nucleic acid polymerases described herein below in the section "PCR reagents";
d) preparing partitioned PCR reactions for example as described herein below in the section "Partitioned PCR reactions"
e) performing an asymmetric incremental polymerase reaction (AIPR) for example as described herein below in the section "Asymmetric incremental polymerase reaction"
f) performing a polymerase chain reaction (PCR), preferably an exponential PCR reaction as described herein below in the section "Exponential PCR"
g) detecting whether the PCR product comprises the target nucleic acid sequence or the variant sequence in the target nucleic acid sequence, wherein said detection for example may be performed as described herein below in the section "Detection".

Each partitioned PCR reaction should comprise at least part of the sample, the set of primers, and sufficient PCR reagents to allow a PCR reaction. Methods and reagents useful for performing a PCR reaction are well known to the skilled person. For example each partitioned PCR reaction may comprise any of the nucleic acid polymerase and PCR reagents, described herein below in the section "PCR reagents".

Depending on the mode of detecting whether the PCR product comprises the variant sequence, each partitioned PCR reaction may also comprise detection reagents, such as any of the detection reagent described below in the section "Detection".

The methods of the invention are for example useful for applications that require high-performance discrimination between any two sequences that a number of nucleotides. For example the methods of the invention are useful for applications that require high-performance discrimination between any two sequences that differs by only one or a few nucleotide bases and where the inherent polymerase base incorporation error rate can lead to falsely-positive target sequences of interest. The methods can be used with probe-based discrimination of single-nucleotide variants for example as described herein below in the section "Detection" or with primer-based discrimination. The method can be applied to any type of unmodified or modified deoxyribonucleic or ribonucleic acid (DNA/RNA) sequences of interest in any organism and of any length from a few dozen nucleotides in length to many hundreds to thousands of nucleotides in length. The method can be used with unmodified or modified primers, with or without unmodified or modified probes. The method can be performed in multiplex with many simultaneous interrogations of multiple target sequences of interest.

In general the methods of the invention have a very low limit of detection. This enables a detection of target nucleic acid sequence potentially present at very low levels, and/or detection of the presence of variant sequences potentially present at very low levels in mixtures comprising other target nucleic acid sequences. In general, a large difference between the melting temperature of primer-H and primer-L may enable a very low limit of detection. Useful melting temperatures of primer-H and primer-L are described herein below. Also a large difference between the applied high annealing temperature and low annealing temperature may enable a very low limit of detection. Useful high and low annealing temperatures are described herein below.

The limit of detection may be determined in various manners. For example the limit of detection may be determined by determining the minimum mutant allele fraction (MAF) that can be reliably differentiated from a negative control containing only wild-type template. The mutant allele fraction is the fraction of mutant alleles detected in compared to the total number of alleles (wild-type plus mutant) detected. In theory, the MAF should be zero when the input template is wild-type only, however due to false positives the fraction may be higher than zero. False-positives lead to a poorer limit of detection for a method because very low MAF in a true positive cannot be distinguished from the very low MAF detected in a true negative. Preferably, the methods of the invention has a limit of detection MAF which is lower than 0.01%, for example it may be lower than 0.001%. The MAF may for example be determined as described herein below in Example 1.

A Kit-of-Parts
The present invention also provides kit-of-parts comprising:
a) a set of primers, which for example may be any of the sets of primers described herein below in the section "Set of primers",
b) a detection probe being capable of hybridizing to the target nucleic acid sequence, said probe being linked to at least one fluorophore and at least one quencher, wherein said detection probe for example may be any of the detection probes described herein below in the section "Detection",
c) a nucleic acid polymerase, which for example may be any of the nucleic acid polymerases described herein below in the section "PCR reagents";
d) PCR reagents, which for example may be any of the reagents described herein below in the section "PCR reagents";
e) reagents for preparing droplets containing partitioned PCR reactions, which for example may be any of the reagents described herein below in the section "Partitioned PCR reactions".

The kit-of-parts are particularly useful for performing the methods of the invention.

Variant Sequence and Target Nucleic Acid Sequence

As described above the methods of the invention are useful for detecting the presence of a variant sequence in a target nucleic acid sequence.

Frequently, said variant sequence may be a mutated sequence. Thus, the target nucleic acid sequence may be a nucleic acid sequence, which may be present either as a wild-type sequence or as a mutated sequence.

It is also possible that the variant sequence is a polymorphism, and thus the target nucleic acid sequence may be present as various different polymorphs. In order to simplify the discussion the most commonly occurring target nucleic acid sequence is herein also referred to as the "wild-type sequence" even though strictly speaking also the variant sequence in some circumstances can be considered a wild-type sequence.

Thus, the methods of the invention may be methods for detecting the presence of a variant sequence in a target nucleic acids sequence, wherein said target nucleic acid sequence potentially can be present as a wild-type sequence or it may comprise the variant sequence.

The variant sequence may differ from the wild-type sequence by substitution(s), deletion(s) and/or insertions(s). It may be preferred that both the wild-type sequence and the variant sequence can be amplified in a PCR reaction by the pair of primers specifically capable of amplification of the target nucleic acid sequence. Accordingly, it may be preferred that the wild-type sequence and the variant sequence does not differ too much from each other in length. The variant sequence may for example differ from the wild-type sequence by insertion of in the range of 1 to 1000 nucleotides, such as in the range of 1 to 100 nucleotides, for example in the range of 1 to 50 nucleotides, such as in the range of 1 to 10 nucleotides, for example in the range of 1 to 5, nucleotides, such as insertion of 1 nucleotide. Similarly, the variant sequence may for example differ from the wild-type sequence by deletion of in the range of 1 to 1000 nucleotides, such as in the range of 1 to 100 nucleotides, for example in the range of 1 to 50 nucleotides, such as in the range of 1 to 10 nucleotides, for example in the range of 1 to 5, nucleotides, such as deletion of 1 nucleotide. The variant sequence may also differ from the wild-type sequence by substitution, for example by substitution of in the range of 1 to 1000 nucleotides, such as in the range of 1 to 100 nucleotides, for example in the range of 1 to 50 nucleotides, such as in the range of 1 to 10 nucleotides, for example in the range of 1 to 5, nucleotides, such as substitution of 1 nucleotide.

Thus, in one embodiment of the invention, the variant sequence may differ from the wild-type sequence by only one nucleotide, e.g. by deletion, insertion or substitution of 1 nucleotide. Thus, the variant sequence may be a single nucleotide variation or single nucleotide mutation. The variant sequence may also be a polymorphism, such as a single nucleotide polymorphism.

As explained above, it may be preferred that both the wild-type sequence and the variant sequence can be amplified in a PCR reaction using the pair of primers specifically capable of amplification of the target nucleic acid sequence. Said pair of primers consists of a forward primer and a reverse primer. It is preferred that the forward primer comprises or even consists of a sequence identical to a part of the target sequence, which is present both in the wild-type target sequence and in the target sequence comprising the variant sequence. It is however also possible that the forward primer comprises or even consists of a sequence identical to a part of the target sequence expect for a few mismatches, e.g. except for up to 10 mismatches, such as up to 5 mismatches, for example up to 2 mismatches. Similarly, it is preferred that the reverse primer comprises or even consists of a sequence complementary to a part of the target sequence, which is present both in the wild-type target sequence and in the target sequence comprising the variant sequence. It is however also possible that the reverse primer comprises or even consists of a sequence complementary to a part of the target sequence expect for a few mismatches, e.g. except for up to 10 mismatches, such as up to 5 mismatches, for example up to 2 mismatches. Primers may contain mismatches for various reasons for example in order to adjust the primer to a suitable Tm. In that manner the methods of the invention will result in the amplification of both the wild-type target sequence and the target sequence comprising the variant sequence. Thus, the PCR product may comprise both the target nucleic acid sequence comprising the variant sequence and the target nucleic acid sequence not having the variant sequence.

The presence of the variant sequence may then be determined by any method available to the skilled person, for example as described herein below in the section "Detection".

As described herein above the methods of the invention may be used to discriminate between two very similar sequences, and thereby detect the presence of a variant sequence similar to a wild-type sequence.

There may be many different reasons, why it is desirable to detect a given variant sequence. For example the variant sequence may be associated with a clinical condition or a risk of acquiring a clinical condition. The variant sequence may also provide a fingerprint or at least contribute to a fingerprint of an individual, thereby aiding in the identification of an individual. This may have forensic applications.

However, the methods of the invention may also be used simply to detect the presence of a given target nucleic acid sequence. Said target nucleic acid sequence may be any nucleic acid sequence, which is desirable to detect. For example it may be desirable to detect the presence of nucleic acids from a foreign pathogen. It is generally preferred that the target nucleic acid sequence is suitable as a template for nucleic acid polymerases.

Set of Primers

The methods described herein involve use of a set of primers. The set of primers comprises at least a pair of primers specifically capable of amplification of the target nucleic acid sequence, and the set of primers comprise at least a primer-H and a primer-L.

It is comprised within the invention that the primer-H and primer-L can constitute a pair of primers specifically capable of amplification of the target nucleic acid sequence.

Thus, in some embodiments of the invention the set of primers may consist of the primer-H and the primer-L.

In certain embodiments of the invention, the portioned PCR reactions only contain the following nucleic acids: nucleic acids present in the sample, primer-H, primer-L, free nucleotides, and optionally one or more detection probes.

It is however also possible that the pair of primers specifically capable of amplification of the target nucleic acid sequence are different to primer-H and primer-L. It is also comprised within the invention that primer-L together with a primer, which is not primer-H constitutes the pair of primers specifically capable of amplification of the target nucleic acid sequence.

The pair of primers specifically capable of amplification of the target nucleic acid sequence consists of two primers, which may be denoted a forward primer and a reverse primer. The forward primer is preferably capable of annealing to the complementary strand of the target nucleic acid sequence at the 5'-end or close to the 5'-end of the target nucleic acid sequence. Preferably the forward primer comprises a sequence identical to the 5'-end of the target nucleic acid sequence. The forward primer may even consist of a sequence identical to the 5'-end of the target nucleic acid sequence. In the event that the forward primer comprises a sequence not identical to target nucleic acid sequence, it is preferred that the 3'end of the primer consists of a sequence identical to the target nucleic acid sequence. The reverse primer is preferably capable of annealing to the target nucleic acid sequence at the 3'-end or close to the 3'-end of the target nucleic acid sequence. Preferably the reverse primer comprises a sequence complementary to the 3'-end of the target nucleic acid sequence. The reverse primer may even consist of a sequence complementary to the 3'-end of the target nucleic acid sequence. In the event that the reverse primer comprises a sequence not complementary to the target nucleic acid sequence, it is preferred that the 5'-end of the primer consists of a sequence complementary to the target nucleic acid sequence.

It is contemplated that the forward primer may be primer-H, and the reverse primer may be primer-L.

It is also contemplated that the forward primer may be primer-H, and the reverse primer may be a primer, which is neither primer-H nor primer-L.

It is also contemplated that the forward primer may be primer-L, and the reverse primer may be primer-H.

It is also contemplated that the forward primer may be primer-L, and the reverse primer may be a primer, which is neither primer-H nor primer-L.

In embodiments of the invention wherein the forward primer is primer-H, it may be preferred that the PCR reactions only comprise reverse primers having a melting temperature, which is at least 10° C. lower, preferably at least 15° C. lower, such as at least 20° C. lower, for example at least 25° C. lower, such as at least 30° C., such as in the range of 15 to 50° C., for example in the range of 15 to 40° C. lower than the melting temperature of primer-H. In embodiments of the invention, wherein the set of primers comprise several pairs of primers consisting of a primer-H and a reverse primer, then each reverse primer preferably has aforementioned melting temperature in relation the primer-H of the pair of primers.

In embodiments of the invention wherein the reverse primer is primer-H, it may be preferred that the PCR reactions only comprise forward primers having a melting temperature, which is at least 10° C. lower, preferably at least 15° C. lower, such as at least 20° C. lower, for example at least 25° C. lower, such as at least 30° C., for example in the range of 15 to 50° C. lower, for example in the range of 15 to 40° C. lower than the melting temperature of primer-H. In embodiments of the invention, wherein the set of primers comprise several pairs of primers consisting of a primer-H and a forward primer, then each forward primer preferably has aforementioned melting temperature in relation the primer-H of the pair of primers.

The primers may be any oligonucleotide or nucleic acid capable of acting as a point of initiation of DNA synthesis under suitable conditions. Such conditions can include those of AIPR or PCR described herein below in the section "Asymmetric incremental polymerase chain reaction" or "Exponential PCR".

In some cases, a primer may be detectably labeled. In some cases, a primer is not detectably labeled.

The length of the primers can depend on the sequence of the target nucleic acid sequence. As explained herein elsewhere the primer-H has a melting temperature which is significantly higher than the melting temperature of the primer-L. If the set of primers contains more primers than primer-H and primer-L, then it is preferred that the remaining primers are designed to have a melting temperature similar to the melting temperature of primer-L or lower than the melting temperature of primer-L. It is however comprised within the invention that the set of primers may comprise more than one primer-H. In such cases it is preferred that any primer, which together with any of the primer-Hs are capable of amplification of a target nucleic acid have a melting temperature similar to the melting temperature of primer-L or lower than the melting temperature of primer-L.

Thus, it is preferred that the set of primers comprises primer-H and primer-L, wherein primer-H has a melting temperature which is at least 10° C. higher than the melting temperature of all other primers in the set of primers. For example, primer-H may have a melting temperature which is at least 12° C., such as at least 14° C., for example at least 16° C., such as at least 18° C., for example at least 20° C. higher than the melting temperature of all other primers in the set of primers. Primer-H may have an even higher melting temperature, for example a melting temperature which is at least 25° C. higher, such as at least 30° C. higher, for example a melting temperature, which is in the range of 15 to 50° C., such as in the range of 15 to 40° C. higher than the melting temperature of all other primers in the set of primers. If the partitioned PCR reactions also comprises one or more probes, such probes may also have a melting temperature, which is at least 10° C., such as at least 12° C., such as at least 14° C., for example at least 16° C., such as at least 18° C., for example at least 20° C. lower than the melting temperature of primer-H. However, the probes may also have higher melting temperatures.

In one embodiment primer-H is the only primer in the set of primers that has a melting temperature at least 10° C. higher than the melting temperature of primer-L. In said embodiment all other primers have a melting temperature, which is at the most 10° C. higher than the melting temperature of primer-L. For example, all primers except primer-H may have a melting temperature within the range of +/−10° C. of the melting temperature of primer-L, such as within the range of +/−8° C. of the melting temperature of primer-L, for example within the range of +/−6° C. of the melting temperature of primer-L, such as within the range of +/−4° C. of the melting temperature of primer-L. If the partitioned PCR reactions also comprises one or more probes, said probes may also have a melting temperature within the range of +/−10° C. of the melting temperature of primer-L, such as within the range of +/−8° C. of the melting temperature of primer-L, for example within the range of +/−6° C. of the melting temperature of primer-L, such as within the range of +/−4° C. of the melting temperature of primer-L. It is however also comprised within the invention that the probes have a higher melting temperature, for example a melting temperature up to 20° C. higher than the melting temperature of primer-L.

In one embodiment of the invention it is preferred that the set of primers do not comprise any primers:
   a) which have a melting temperature which is in the range of +/−15° C., preferably in the range of +/−20° C., such as in the range of +/−25° C., for example in the range of +/−10° C. of the melting temperature of primer-H, such as within the range of +/−8° C. of the melting temperature of primer-H, for example within the range of +/−6° C. of the melting temperature of primer-H, such as within the range of +/−4° C. of the melting temperature of primer-H; and b) which together with primer-H can constitute a pair of primers specifically capable of amplification of the target nucleic acid sequence.

In one embodiment of the invention it is preferred that all primers within the set of primers, which together with primer-H can constitute a pair of primers specifically capable of amplification of the target nucleic acid sequence, have a melting temperature which at least 10° C., preferably at least 15° C., such as at least 20° C., for example at least 25° C., such as at least 30° C., for example in the range of 15 to 50° C., such as in the range of 15 to 40° C. lower than the melting temperature of primer-H.

Thus, it is preferred that the set of primers comprises primer-H and primer-L, wherein primer-H has a melting temperature which is at least 10° C. higher than the melting temperature of all other primers in the set of primers. For example, primer-H may have a melting temperature which is at least 12° C., such as at least 14° C., for example at least 16° C., such as at least 18° C., for example at least 20° C. higher than the melting temperature of all other primers in the set of primers. If the partitioned PCR reactions also comprises one or more probes, such probes may also have a melting temperature, which is at least 10° C., such as at least 12° C., such as at least 14° C., for example at least 16° C., such as at least 18° C., for example at least 20° C. lower, for example in the range of 20 to 45° C. lower than the melting temperature of primer-H. However, it also comprised within the invention that the probes may have a higher melting temperature, even a melting temperature similar to the melting temperature of primer-H.

The skilled person will be able to design primers having an appropriate melting temperature. In general, the melting temperature of a primer may depend on the length of the primer, the sequence of the primer and also on the presence of nucleotide analogues. There are some restrictions to the sequence of the primer, because it should be able to anneal to the target nucleic acid sequence and/or the complementary sequence. Thus, within the restriction to the sequence, the skilled person may design a primer having the desired melting temperature by adjusting the length of the primer. The melting temperature (Tm) may be determined as described herein above in the section "Definitions".

The melting temperature may also depend on the presence of nucleotide analogues, and thus primers having an appropriate melting temperature can be designed by designing primers comprising one or more nucleotide analogues. The melting temperature may also depend on the presence of nucleotide mismatches to the target nucleic acid, and thus primers having an appropriate melting temperature can be designed comprising one or more nucleotide mismatches.

Primers can incorporate additional features that allow for the detection or immobilization of the primer but do not alter a basic property of the primer (e.g., acting as a point of initiation of DNA synthesis). For example, primers can contain an additional nucleic acid sequence at the 5'-end which does not hybridize to the target nucleic acid sequence or the sequence complementary to the target nucleic acid sequence, but which facilitates cloning or detection of an amplified product. For example, the additional sequence can comprise a restriction enzyme cleavage and/or recognition site. A region of the primer which is sufficiently complementary to a template to hybridize can be referred to herein as a hybridizing region. Primers may also be linked to tags, for example fluorescent, functionalized, or binding tags. Said tags may be bound to their ends, sugars, or nucleobases. Primers can also contain 3'-end mismatch(es) in designs where the primer discriminates between wild-type and variant target nucleic acid sequences, to diminish or extinguish elongation of the undersired template sequence.

The primer may be a single-stranded DNA prior to binding a template nucleic acid. In some cases, the primer initially comprises double-stranded sequence, e.g. the primer may form a hairpin loop. Thus, in general a primer is a polynucleotide or oligonucleotide, and frequently the primers are DNA. However, primers according to the invention may comprise one or more nucleotide analogues as well as comprise ribonucleic acid (RNA).

Nucleotide analogues are well known in the art, and the primers and probes of the invention may incorporate any useful nucleotide analogue. Nucleotide analogues may for example be nucleotide analouges having a modified sugar group, locked nucleic acid (LNA) nucleotide analogues, peptide nucleic acid (PNA) nucleotide analogues, glycol nucleic acid (GNA) nucleotide analogues, threose nucleic acid (TNA) nucleotide analogues, bicyclic and tricyclic nucleoside analogs, phosphonomonoester nucleic acids which incorporate a phosphorus group in the backbone, or polycyclic heterocyclic compounds, which can be used in place of one or more of the naturally-occurring heterocyclic base moieties.

In another embodiment, a primer or a probe utilized in methods and compositions described herein can comprise one or more universal nucleosides. Non-limiting examples of universal nucleosides are 5-nitroindole and inosine.

Primers can be designed according to known parameters for avoiding secondary structures and self-hybridization.

Primers are commercially available from a number of providers and can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)).

Primer-H and Primer-L

The methods and kits of the invention involves use of a set of primers comprising a primer-H and a primer-L, wherein the melting temperature of primer-H is at least 10° C., preferably at least 15° C. higher than the melting temperature of primer-L, and wherein primer-L contains a sequence complementary to the elongation product of primer-H. The set of primers may comprise other primers, for example as described herein above in the section "Set of primers", however the set of primers may also consist of the primer-H and the primer-L, wherein the primer-H and primer-L are specifically capable of amplification of the target nucleic acid sequence.

The primer-H is preferably designed as a primer for amplification of the target sequence or the sequence complementary to the target sequence. Thus, the primer-H is preferably capable of annealing to either the target nucleic acid sequence or to the sequence complementary to the target nucleic acid sequence. For example, primer-H may be capable of annealing to the complementary strand of the target nucleic acid sequence at the 5'-end or close to the 5'-end of the target nucleic acid sequence, or the primer-H may be capable of annealing to the target nucleic acid sequence at the 3'-end or close to the 3'-end of the target nucleic acid sequence. Thus, the primer-H may comprise a sequence identical to the 5'-end of the target nucleic acid sequence. The primer-H may even consist of a sequence identical to the 5'-end of the target nucleic acid sequence. The primer-H may also comprise a sequence identical to the target nucleic acid sequence. Thus, the primer-H may comprise a sequence complementary to the 3'-end of the target nucleic acid sequence. The primer-H may even consist of a sequence complementary to the 3'-end of the target nucleic acid sequence.

Similarly, the primer-L is preferably designed as a primer for amplification of the target sequence or the sequence complementary to the target sequence. If the primer-H is designed for amplification of the target sequence, the primer-L is preferably designed for amplification of the sequence complementary to the target sequence and vice versa. Thus, the primer-L is preferably capable of annealing to either the target nucleic acid sequence or to the sequence complementary to the target nucleic acid sequence. If primer-H is capable of annealing to the target nucleic acid sequence, then primer-L is preferably capable of annealing to the sequence complementary to the target nucleic acid sequence and vice versa. For example, primer-L may be capable of annealing to the complementary strand of the target nucleic acid sequence at the 5'-end or close to the 5'-end of the target nucleic acid sequence, or the primer-L may be capable of annealing to the target nucleic acid sequence at the 3'-end or close to the 3'-end of the target nucleic acid sequence. Thus, the primer-L may comprise a sequence identical to the 5'-end of the target nucleic acid sequence. The primer-L may even consist of a sequence identical to the 5'-end of the target nucleic acid sequence. The primer-L may also comprise a sequence identical to the target nucleic acid sequence. Thus, the primer-L may comprise a sequence complementary to the 3'-end of the target nucleic acid sequence. The primer-L may even consist of a sequence complementary to the 3'-end of the target nucleic acid sequence.

In one embodiment of the invention the primer-H comprises or consists of a nucleotide sequence, which is identical to the sequence at the 5'-end of the target nucleic acid sequence and the primer-L comprises or consists of a sequence identical to the complementary sequence of the 3'-end of the target nucleic acid sequence.

In another embodiment of the invention the primer-L comprises or consists of a nucleotide sequence, which is identical to the sequence at the 5'-end of the target nucleic acid sequence and the primer-H comprises or consists of a sequence identical to the complementary sequence of the 3'-end of the target nucleic acid sequence.

In yet another embodiment of the invention primer-L consists of two parts, one part being complementary or identical to a fragment of the target nucleic acid sequence and another part which is not complementary or identical to the target nucleic acid sequence. Such primers may also be referred to as "mismatch modified primer-L" herein. Said part being complementary or identical to a fragment of the target nucleic acid sequence may have a very low melting temperature, and may be referred to as the "non-mismatched part of primer-L". The non-mismatched part of primer-L may typically consists of in the range of 7 to 15, nucleotides, for example in the range of 7 to 12 nucleotides. Said part which is not complementary or identical to the target nucleic acid sequence may contain a random sequence and may be referred to as the "mismatched part of primer-L". The mismatched part of primer-L may typically consist of 2 to 8 nucleotides, such as in the range of 2 to 6 nucleotides, but could be 1 nucleotide or >8 nucleotides. This may in particular be the case in embodiments of the invention comprising a step of low temperature PCR as described herein above in the section "Low temperature PCR". The 3'-end of said primer-L may for example be at a base which varies between a true target nucleic acid sequence and a closely homologous non-target. The mismatched part, upon incorporation into newly synthesized nucleic acids and following synthesis of the $2^{nd}$ complementary strand, may become a proper hybridization region.

The primer-H and the primer-L are designed to have the melting temperatures as indicated herein. The skilled person will be capable of designed primer-H and primer-L to have the desired melting temperature by adjusting the sequence of the primers, the length of the primers and optionally by incorporating nucleotide analogues as described herein above in the section "Set of primers".

The primer-H is designed so that the primer-H has an annealing temperature which is significantly higher than the annealing temperature of primer-L, for example at least 10° C. higher. Thus, the melting temperature of the primer-H may be at least 12° C. higher, for example at least 15° C. higher, preferably at least 14° C. higher, even more preferably at least 16° C. higher, yet more preferably 18° C. higher, such as at least 20° C. higher, for example in the range of 15 to 50° C., such as in the range of 15 to 40° C., for example in the range of 15 to 25° C. higher than the melting temperature of the primer-L. In some embodiments it is preferred that the melting temperature of the primer-H is at least 30° higher, such as in the range of 30 to 50.

In general it is preferred that the melting temperature of primer-H is as high as possible, but not higher than the highest functional elongation temperature of at least one nucleic acid polymerase. Said elongation temperature does not need to be the optimum temperature for said nucleic acid polymerase, but it is preferred that at least one nucleic acid polymerase has activity at the melting temperature primer-H. Thus, the melting temperature of the primer-H may approach or may even exceed 80° C.

Primer-H may comprise one or more nucleotide analogues, for example any of the nucleotide analogues described herein above in the section "Set of primers". Incorporation of some nucleotide analogues may increase the melting temperature, and accordingly, Primer-H may in particular comprise nucleotide analogues, wherein the incorporation of said nucleotide analogues increase the melting temperature of the primer. Thus, Primer-H may comprise one or more LNAs, PNAs, GNAs and/or TNAs. For example, Primer-H may comprise in the range of 1 to 20, such as in the range of 1 to 15, for example in the range of 5 to 10 nucleotide analogues, for example LNA.

Since it is also preferred that the melting temperature of primer-L is sufficiently high to ensure specific annealing of primer-L to the target nucleic acid sequence/the complementary sequence of the target nucleic acid sequence, and the melting temperature of primer-H should be significantly higher than the melting temperature of primer-H, then frequently, the melting temperature of primer-H is at least 60° C. The melting temperature of primer-H may also frequently be at least 70° C. The melting temperature of primer-H may for example be in the range of 60 to 90° C., for example in the range of 60 to 85° C., such as in the range of 70 to 85° C., for example in the range of 70 to 80° C.

The melting temperature of primer-L is preferably sufficiently high to ensure specific annealing of primer-L to the target nucleic acid sequence/the complementary sequence of the target nucleic acid sequence, but also significantly lower than the melting temperature of primer-H. Frequently, the melting temperature of the primer-L is in the range of 30 to 55° C., such as in the range of 35 to 55° C., preferably in the range of 40 to 50° C.

PCR Reagents

The methods of the invention involve steps of performing PCR. The skilled person is well aware of how perform a PCR and which reagents may be useful for performing a PCR. Such reagents are referred to as PCR reagents herein. The kit-of-parts of the invention also comprise PCR reagents.

For most purposes the PCR reagents comprise nucleotides. Thus, the PCR reagents may comprise deoxynucleoside triphosphates (dNTPs), in particular all of the four naturally-occurring deoxynucleoside triphosphates (dNTPs).

The PCR reagents frequently comprise deoxyribonucleoside triphosphate molecules, including all of dATP, dCTP, dGTP, dTTP. In some cases dUTP is added.

The PCR reagents may also comprise compounds useful in assisting the activity of the nucleic acid polymerase. Thus, the PCR reagent may comprise a divalent cation, e.g., magnesium ions. Said magnesium ions may be added on the form of e.g. magnesium chloride or magnesium acetate (MgCl2) or magnesium sulfate is used.

The PCR reagents may also comprise one or more of the following:
non-specific blocking agents such as BSA or gelatin from bovine skin, betalactoglobulin, casein, dry milk, or other common blocking agents,
non-specific background/blocking nucleic acids (e.g., salmon sperm DNA),
biopreservatives (e.g. sodium azide),
PCR enhancers (e.g. Betaine, Trehalose, etc.),
inhibitors (e.g. RNAse inhibitors).

The PCR reagent a may also contain other additives, e.g., dimethyl sulfoxide (DMSO), glycerol, betaine (mono)hydrate (N,N,N-trimethylglycine=[caroxy-methyl]trimethyl-ammonium), trehalose, 7-Deaza-2'-deoxyguanosine triphosphate (dC7GTP or 7-deaza-2'-dGTP), formamide (methanamide), tettrmethylammonium chloride (TMAC), other tetraalkylammonium derivaties (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q.

The PCR reagents may comprise a buffering agent.

In some cases, a non-ionic Ethylene Oxide/Propylene Oxide block copolymer is added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

The methods of the invention also involves use of a nucleic acid polymerase and the kit-of-part of invention also comprise a nucleic acid polymerase. Said nucleic acid polymerase may be any nucleic acid polymerase, such as a DNA polymerase. The nucleic acid polymerase should have activity at the elongation temperature.

In some embodiments the nucleic acid polymerase is a DNA polymerase with 5' to 3' exonuclease activity. This may in particular be the case in embodiments of the invention, wherein the methods or kits involves use of a detection probe, such as a Taqman detection probe.

Any DNA polymerase, e.g., a DNA polymerase with 5' to 3' exonuclease activity that catalyzes primer extension can be used. For example, a thermostable DNA polymerase can be used.

In one embodiment the nucleic acid polymerase is a Taq polymerase.

Partitioning PCR Reactions

The methods of the invention in general comprising a step of preparing partitioned PCR reactions. The partitioned PCR reaction may then be subjected to a step of AIPR followed by one or more PCRs as described herein. Preparing partitioned PCR reactions involves dividing the sample into multiple smaller fractions, which each comprises a set of primers, nucleic acid polymerase, PCR reagents and optionally detection reagents.

The partitioned PCR reactions may be prepared by a number of different methods. In general it involves dividing the PCR reactions into physically and spatially separated compartments. Said compartments may be obtained in a number of ways, for example the PCR reactions may be divided into different containers. The partitioned PCR reactions may also be prepared by dividing the PCR reaction into wells of microtiter plates. The partitioned PCR reactions may also be prepared by dividing the PCR reaction into microwells, microfluidic chambers, capillaries, dispersed phase of an emulsion, a chamber (e.g., a chamber in an array of miniaturized chambers), a droplet, or a nucleic acid binding surface. The partitioned PCR reactions may also be prepared by dividing the PCR reaction onto discrete spots on a solid support.

It is preferred that the PCR reactions are partitioned in a manner so that each partitioned PCR reaction only comprises a small number of template nucleic acids comprising the target nucleic acid sequence. Since the sample normally is distributed randomly into the partitioned PCR reactions it is possible that some reactions comprise more template nucleic acids comprising the target nucleic acid sequence than others. In fact some of the partitioned PCR reactions may comprise no template nucleic acids comprising the target nucleic acid sequence, whereas others may comprise several copies. If the copies of the template nucleic acid are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of the template nucleic acid in the partitions, is described by a Poisson distribution. Some samples will comprise no template nucleic acids comprising the target sequence, and in such embodiment also none of the partitioned PCR reactions will comprise template nucleic acids comprising the target sequence.

In one embodiment the partitioned PCR reactions each comprises at the most 10, such as at the most 5 template nucleic acids comprising the target nucleic acid sequence.

One very useful method for preparing partitioned PCR reactions is by preparing enclosed reaction droplets, wherein each droplet contains a partitioned PCR reaction. Thus, the partitioned PCR reactions may each be contained in droplets prepared using a droplet generator.

The size of such droplets may vary, but the partitioned PCR reactions may for example each be contained in a droplet of a volume in the range of 1 to 10,000 picoliters, for example approximately 1000 picoliters.

The droplets used herein can include emulsion compositions (or mixtures of two or more immiscible fluids) for example as described in U.S. Pat. No. 7,622,280 or as described in the Examples herein below. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets used herein are normally designed to prevent mixing between compartments, with each compartment protecting its contents from evaporation and coalescing with the contents of other compartments.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipet manipulations and centrifugation.

Droplets can be polydisperse or monodisperse, generated through agitation, sonication or microfluidically through a T-channel junction or other means by those familiar with the art.

A droplet can be formed by flowing an oil phase through an aqueous sample. The aqueous phase can comprise a buffered solution and reagents for performing a PCR reaction, including nucleotides, primers, probe(s) for fluorescent detection, template nucleic acids, DNA polymerase enzyme, and optionally, reverse transcriptase enzyme.

The aqueous phase generally comprises the sample, the PCR reagents, the nucleic acid polymerase, the set of primers and optionally the detection reagents.

The oil phase can comprise a fluorinated base oil which can be additionally stabilized by combination with a fluorinated surfactant such as a perfluorinated polyether. In some cases, the base oil can be one or more of HFE 7500, FC-40, FC-43, FC-70, or other common fluorinated oil. In some cases, the anionic surfactant is Ammonium Krytox (Krytox-AM), the ammonium salt of Krytox FSH, or morpholino derivative of Krytox-FSH.

The oil phase can further comprise an additive for tuning the oil properties, such as vapor pressure or viscosity or surface tension. Nonlimiting examples include perfluorooctanol and 1H,1H,2H,2H-Perfluorodecanol.

The emulsion can be formulated to produce highly monodisperse droplets having a liquid-like interfacial film that can be converted by heating into microcapsules having a solid-like interfacial film; such microcapsules can behave as bioreactors able to retain their contents through a reaction process such as AIPR or PCR amplification. The conversion to microcapsule form can occur upon heating. For example, such conversion can occur at a temperature of greater than about 50, 60, 70, 80, 90, or 95 degrees Celsius. In some cases this heating occurs using a thermocycler. During the heating process, a fluid or mineral oil overlay can be used to prevent evaporation. The biocompatible capsules can be resistant to coalescence and/or flocculation across a wide range of thermal and mechanical processing.

In some cases, the droplet is generated using commercially available droplet generator, such as Bio-Rad QX100™ Droplet Generator. The AIPR and the PCR may be carried out using commercially available apparatus, and the droplets may be analyzed using commercially available droplet reader such as generator, such as Bio-Rad QX100™ Droplet Reader.

Asymmetric Incremental Polymerase Reaction

The methods of the invention comprise a step of asymmetric incremental polymerase reaction (AIPR). It is important that the AIPR is performed prior to any steps of exponential PCR. Accordingly, in general step e) is performed before step f). The AIPR comprises the steps of:
 i. incubating the partitioned PCR reactions at a denaturation temperature, thereby denaturing DNA to single-stranded molecules
 ii. incubating the partitioned PCR reactions at a high annealing temperature allowing annealing of primer-H, but not of primer-L,
 iii. optionally incubating the partitioned PCR reactions at the elongation temperature,
 iv. optionally repeating steps i to iii.

In general, AIPR is an asymmetric reaction resulting in amplification of only one strand of the target nucleic acid sequence. Thus, preferably the PCR reaction does not comprise any other primer, which together with primer-H is capable of amplification of the target nucleic acid sequence, wherein said other primer has a melting temperature similar to or higher than the melting temperature of primer-H. In embodiments of the invention, wherein the set of primer comprises multiple primer-Hs it is preferred that the PCR reaction does not comprise any other primers, which together with any of the primer-H are capable of amplification of any of the target nucleic acid sequences, wherein said other primers have a melting temperature similar to or higher than the melting temperature of primer-H. Preferred melting temperatures of the primers are described in the section "Set of primers" and "Primer-L and Primer-H". Thus, at the high annealing temperature only primer-H will be annealed resulting in polymerisation only from primer-H. Thus, multiple rounds of AIPR leads to amplification of only one strand of the target nucleic acid sequence, and AIPR is thus in principle a linear amplification.

Frequently, the nucleic acid polymerase has elongation activity at the high annealing temperature. In such embodiments the high annealing temperature can also be considered to be the elongation temperature even if the high annealing temperature is not the temperature optimum for the nucleic acid polymerase. Thus, the AIPR may comprise only two steps, which are repeated, i.e. a step of denaturing by incubation at the denaturation temperature, and a combined step of annealing and elongation of primer-H by incubation at the high annealing temperature. In said embodiments, the primer-H is preferably designed to have a melting temperature, at a temperature where the nucleic acid polymerase has sufficient activity to catalyse elongation of primer-H.

Accordingly, the AIPR of step e) may comprise the steps of:
  i. incubating the partitioned PCR reactions at a denaturation temperature, thereby denaturing DNA to single-stranded molecules
  ii. incubating the partitioned PCR reactions at a high annealing temperature allowing annealing of primer-H, but not of primer-L, wherein the high annealing temperature also is the elongation temperature, thereby allowing for extension of the annealed primer-H;
  iii. repeating steps i to ii, In other embodiments of the invention, the melting temperature of primer-H is different to the elongation temperature. In such embodiments, the AIPR of step e) may comprise the steps of:
  i. incubating the partitioned PCR reactions at a denaturation temperature, thereby denaturing DNA to single-stranded molecules
  ii. incubating the partitioned PCR reactions at a high annealing temperature allowing annealing of primer-H, but not of primer-L,
  iii. incubating the partitioned PCR reactions at the elongation temperature, thereby allowing elongation of the annealed primer-H,
  iv. repeating steps i to iii.

The step i. of incubating the partitioned PCR reactions at a denaturation temperature, is done sufficiently long to denature DNA to single-stranded molecules. It is possible that the step i. is performed for a longer time during the first cycle of the AIPR than in the later cycles. The skilled person will be able to select appropriate times for incubation at the denaturing temperature. In the first cycle the incubation at the denaturing temperature may for example be for in the range of 0.5 to 10 min (for example for hot-start DNA polymerases), whereas in the following cycles the incubation at the denaturing temperature for example may be for in the range of 0.1 to 2 min.

Similarly, the skilled person will be able to select appropriate times for incubation at the high annealing temperature/elongation temperature. In the last cycle the incubation at the elongation temperature may longer than in the other cycles, for example for in the range of 0.5 to 10 min, whereas in the other cycles the incubation at elongation temperature for example may be for in the range of 0.1 to 2 min. As outlined above, then the high annealing temperature may be the same as the elongation temperature. In embodiments where the high annealing temperature is different to the elongation temperature, then the incubation at the annealing temperature could for example be in the range of 0.1 to 2 min.

Steps i to ii may be repeated for suitable number of times. In general steps i to ii are repeated for a number of times sufficient to ensure a very low to no occurrence of false positive signals. For example, steps i. to ii. may be repeated for in the range of 8 to 256 times, preferably for in the range of 16 to 128 times, for example for in the range of 32 to 128 times, for examples approximately 64 times, such as 64 times.

In embodiments of the invention, wherein the high annealing temperature and the elongation temperature are different then steps i. to iii. may be repeated for in the range of 8 to 256 times, preferably for in the range of 16 to 128 times, for example for in the range of 32 to 128 times, for examples approximately 64 times, such as 64 times.

It is preferred that during the AIPR, then only incremental copying is performed. In other words it is preferred that only one strand of the target nucleic acid serves as a template for copying during the AIPR. If the primer-H is annealing to a sequence complementary to the target nucleic acid sequence, then it is preferred that only the strand comprising the target nucleic acid sequence is synthesized during the AIPR. Since the AIPR is monodirectional, said strands may have differing lengths, but they preferably comprise at least the target nucleic acid sequence. In this embodiment, the sequence complementary to the target nucleic acid sequence, is preferably not synthezised during a the AIPR stage. Similarly, if the primer-H is annealing to the target nucleic acid sequence, then it is preferred that only the strand comprising the sequence complementary to the target nucleic acid sequence is synthesized during the AIPR. Since the AIPR is monodirectional, said strands may have differing lengths, but they preferably comprise at least the sequence complementary to the target nucleic acid sequence. In this embodiment the target nucleic acid sequence is preferably not amplified during the AIPR.

Thus, in one embodiment of the invention step e) results in elongation of primer-H, but in no detectable elongation of primer-L. For example, step e) may result in elongation of primer-H, but in no elongation of primer-L.

In one embodiment step e) results in elongation of primer-H, but in no detectable elongation of any other primer. For example, step e) may result in elongation of primer-H, but in no elongation of any other primer.

The high annealing temperature is selected to allow annealing of primer-H, but not of primer-L. Accordingly, it is preferred that the high annealing temperature is set to be significantly higher than the melting temperature of primer-L. Thus, the high annealing temperature in step e) may be at least 10° C. higher, preferably at least 15° C. higher, for example at least 20° C., such as at least 25° C. higher than the melting temperature of primer-L.

The high annealing temperature could for example be set to be approximately the melting temperature of the primer-H. It could however also be somewhat lower.

Low Temperature PCR

In some embodiments of the invention, the methods comprise a step of low temperature PCR, which is performed after completion of the AIPR and before the exponential PCR.

In such embodiments the primer-L is typically a mismatch-modified primer-L as described herein above.

This may in particular be the case in tricky targets (for example, a target with a very homologous sequence elsewhere in the genome, such as a pseudogene), this mismatch-modified primer-L can allow for use of a shorter primer-L that is more specific for the true target.

The low temperature PCR typically involves the steps of:
  1) incubating the partitioned PCR reactions at a denaturation temperature, thereby denaturing DNA to single-stranded molecules
  2) incubating the PCR at a very low annealing temperature allowing annealing of both primer-H and of the non-mismatched part of primer-L,
  3) incubating the PCR at the elongation temperature thereby allowing extension of all annealed primers
  4) optionally repeating steps 1) to 3), thereby obtaining a PCR product.

This step will allow amplification of a product which incorporates the mismatched part of primer-L. Once enough of said product is available, then a normal exponential PCR may be performed using a low annealing temperature, which for example may be approximately the melting temperature of primer-L.

In general the very low annealing temperature is lower than the low annealing temperature. Typically, the very low annealing temperature is at least 5° C., preferably at least 10° C., more preferably at least 15° C., such as at least 20° C. lower than the low annealing temperature. For example the very low annealing temperature is in the range of 5 to 30° C. lower than the low annealing temperature, for example the very low annealing temperature may be in the range of 20 to 25° C. lower than the low annealing temperature. Thus, the very low annealing temperature may be at least 20° C. lower, for example at least 25° C., such as at least 30° C., for example at least 35° C. lower than the melting temperature of primer-H.

Typically, the steps 1) to 3) may be repeated more than once, for example in the range of 1 to 40. For example, steps 1) to 3) are repeated in the range of 2 to 10 times, for example 4 to 6 times. It is frequently preferred that the total number of PCR cycles performed during the low temperature PCR and the exponential PCR are in the range of 20 to 40, such as in the range of 20 to 30. Thus, depending on how many times steps I to III of the exponential PCR is repeated, steps 1) to 3) of the low temperature PCR may be repeated to reach a total number of cycles in the range of 20 to 40, such as in the range of 20 to 30.

Exponential PCR

The methods of the invention comprise a step of performing a polymerase chain reaction (PCR). In order to discriminate this step from the AIPR, this step may also be referred to as "exponential PCR". In the methods of the invention, the polymerase chain reaction is performed subsequent to the AIPR. The exponential PCR may in general comprise the steps of:

I. incubating the partitioned PCR reactions at a denaturation temperature, thereby denaturing DNA to single-stranded molecules
  II. incubating the PCR at a low annealing temperature allowing annealing of both primer-H and primer-L,
  III. incubating the PCR at the elongation temperature thereby allowing extension of all annealed primers
  IV. optionally repeating steps I to III, thereby obtaining a PCR product.

Incubation at the low annealing temperature preferably allows for annealing of both primers of the pair of primers specifically capable of amplification of the target nucleic acid sequence. Accordingly, the exponential PCR will result in amplification of both strands of the target nucleic acid sequence. In theory said amplification will be exponential, and thus may be referred to as "exponential PCR", even though in practice it is possible that it is not completely exponential.

The exponential PCR may be performed in any manner, for example in any conventional manner for performing PCR known to the skilled person.

The step I. of incubating the partitioned PCR reactions at a denaturation temperature, is done sufficiently long to denature DNA to single-stranded molecules. It is possible that the step I. is performed for a longer time during the first cycle of the PCR than in the later cycles. The skilled person will be able to select appropriate times for incubation at the denaturing temperature. In the first cycle the incubation at the denaturing temperature may for example be for in the range of 0.5 to 10 min, whereas in the following cycles the incubation at the denaturing temperature for example may be for in the range of 0.1 to 2 min.

Similarly, the skilled person will be able to select appropriate times for incubation at the low annealing temperature. For example the incubation at the low annealing temperature could for example be in the range of 0.1 to 2 min.

Similarly, the skilled person will be able to select appropriate times for incubation at the elongation temperature. In the last cycle the incubation at the elongation temperature may longer than in the other cycles, for example for in the range of 0.5 to 10 min, whereas in the other cycles the incubation at elongation temperature for example may be for in the range of 0.1 to 2 min.

Steps I to III may be repeated for suitable number of times. In general it is preferred that steps I to III are not repeated for too many times in order to reduce the risk of false-positive signals. For example step f) may comprise repeating steps I. to III. for in the range of 15 to 60 times, preferably for in the range of 20 to 40 times, for example for in the range of 20 to 30 times, for example in the range of 25 to 30 times.

In embodiments of the invention, wherein the set of primers comprises additional primers in addition to primer-H and primer-L, then said additional primers in some embodiments may also anneal to their template at the low annealing temperature.

Thus, in one embodiment of the invention step f) results in elongation of primer-H and primer-L. In another embodiment of the invention, step f) results in elongation of all primers of the set of primers.

The low annealing temperature is selected so that primer-L can anneal to the target nucleic acid sequence. Thus, low annealing temperature could for example be set to be approximately the melting temperature of the primer-L. It could however also be somewhat lower.

Examples of PCR techniques that can be used for the exponential PCR include, but are not limited to, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), digital PCR (dPCR), droplet digital PCR (ddPCR), bridge PCR, picotiter PCR, and emulsion PCR.

Detection

The methods of the invention in general comprise a step of detecting, whether the PCR product comprises the variant sequence and/or the target nucleic acid sequence. Said detection may be accomplished in any suitable manner known to the skilled person. For example numerous useful detection methods are known in the prior art, which can be employed with the methods of the invention.

In one embodiment of the invention, said detection involves that the partitioned PCR reactions contains a detection reagent. Said detection reagent may be any detectable reagent, for example it may be a compound comprising a detectable label, wherein said detectable label for example may be a dye, a radioactive activity, a fluorophore, a heavy metal or any other detectable label.

Frequently the detection reagent comprises a fluorescent compound.

In one embodiment of the invention the detection reagent comprises or consists of detection probes. Detection probes preferably comprises or consists of nucleotide oligomers or polymers, which optionally may comprise nucleotide analogues, such as any of the nucleotide analogues described herein above in the section "Set of primers". Frequently, the detection probe may be a DNA oligomer. Typically, the detection probe is linked to a detectable label, for example by a covalent bond. The detectable label may be any of the aforementioned detectable labels, but frequently it is a fluorophore. It is preferred that the probe is not specifically capable of amplification of a target nucleic acid together with Primer-H. For example, if Primer-H comprises a sequence identical to a fragment of the target sequence, then the probe(s) may comprise a sequence identical to another fragment of the target sequence. If Primer-H comprises a sequence complementary to a fragment of the target sequence, then the probe(s) may comprise a sequence complementary to another fragment of the target sequence.

The detection probe is in general capable of specifically binding the target nucleic acid sequence. For example the detection probe may be capable of specifically binding the target nucleic acid comprising the variant sequence. Thus, the detection probe may be capable of annealing to the target nucleic acid sequence or to the sequence complementary to the target nucleic acid sequence. Thus, the detection probe may comprise a sequence identical to a fragment of the target nucleic acid sequence or the sequence complementary to the target nucleic acid sequence. It is generally preferred that the detection probe comprises a sequence different to the sequence of any of the primers of the set of primers.

The detection probe(s) are designed to have an appropriate melting temperature. In one embodiment the melting temperature of at least one detection probe is significantly lower than the melting temperature of primer-H. For example, the melting temperature of all detection probes is significantly lower than the melting temperature of primer-H. Thus, the melting temperature of at least one detection probe may be at least 12° C. lower, preferably at least 14° C. lower, even more preferably at least 16° C. lower, yet more preferably 18° C. lower, such as at least 20° C. lower, for example in the range of 15 to 25° C., such as in the range of 30 to 40° C., or even up to 45° C. lower than the melting temperature of the primer-H. For example, the melting temperature of all detection probes may be at least 12° C. lower, preferably at least 14° C. lower, even more preferably at least 16° C. lower, yet more preferably 18° C. lower, such as at least 20° C. lower, for example in the range of 15 to 45° C. lower than the melting temperature of the primer-H. However, probes with a higher melting temperature can also be applied.

The melting temperature of the detection probe(s) is preferably sufficiently high to ensure specific annealing of detection probes, but also significantly lower than the melting temperature of primer-H. Frequently, the melting temperature of the detection probes may be similar to the melting temperature of primer-L. For example the melting temperature of at least one detection probe may be the same as the melting temperature of primer-L+/−10° C., such as the same as the melting temperature of primer-L+/−5° C., for example approximately the same as the melting temperature of primer-L. In other embodiments the melting temperature of the probe may be higher than the melting temperature of Primer-L, for example 15 to 20° C. higher than the melting temperature of Primer-L. Thus, the detection probe may for example have a melting temperature in the range of 35 to 60° C., such as in the range of 35 to 55° C., preferably in the range of 40 to 50° C.

Frequently, it is preferred that the detection probe provides a different detectable signal depending on the presence of the target nucleic acid sequence. This may be achieved in a number of different manners.

In one embodiment the detection probe is linked to at least one fluorophore and at least one quencher, capable of quenching the signal of the fluorophore, when said detection probe is not bound to its target. Accordingly, the fluorescence of said fluorophore will not be detectable. However, if the detection probe binds to the target nucleic acid sequence/ the sequence complementary to the target nucleic acid sequence, then this leads to the quencher becoming sufficiently far removed from the fluorophore in order to abolished quenching allowing fluorescence of the fluorophore to be detected. Removing the quencher from the fluorophore may be accomplished in various manners. For example, the PCR may employ use of a nucleic acid polymerase having 5' to 3' exonuclease activity. Upon elongation any bound probe will be degraded by said 5' to 3' exonuclease activity thereby separating the fluorophore from the quencher. It is also possible that the detection probe changes 3D conformation upon binding leading to the quencher becoming removed from the fluorophore.

In one embodiment of the invention the partitioned PCR reactions each contain a detection reagent, which is a variant detection probe. The variant detection probe is a detection probe as described above, which is capable of hybridizing to the target nucleic acid sequence containing the variant sequence with significantly higher affinity than to the target nucleic acid sequence not containing the variant sequence.

In one embodiment of the invention the partitioned PCR reactions each contains a detection reagent which is a wild-type detection probe. The wild-type detection probe is a detection probe as described above being capable of hybridizing to the target nucleic acid sequence not containing the variant sequence. It may be preferred that the wild-type detection probe is capable of hybridizing to the target nucleic acid sequence not containing the variant sequence with significantly higher affinity than to the target nucleic acid sequence containing the variant sequence. In embodiments relating to detection of the presence of a target nucleic acid sequence, then the partitioned PCR reactions may each contain a detection reagent which is a wild-type detection probe. In such embodiment it may be sufficient the partitioned PCR reactions contain only one type of detection probe. For example, the PCR reactions may contain a wild-type detection probe as the only detection probe or the PCR reactions may contain variant detection probe as the only detection probe.

In one embodiment of the invention, each partitioned PCR reaction contains both a variant detection probe and a wild-type detection probe. This may in particular be the case in embodiments relating to detection of a variant sequence in a target nucleic acid sequence.

The variant detection probe may be linked to at least one fluorophore and at least one quencher, wherein the quencher is capable of quenching the fluorescence of the fluorophore. Preferably, the quencher and the fluorophore are linked to the variant detection probe in a manner, so that the quencher is capable of quenching the fluorescence of the fluorophore, when the probe is present in its free state. Thus, frequently the fluorophore and the quencher are positioned sufficiently close to each other, so that the quencher is capable of quenching the fluorescence of the fluorophore. Frequently, the fluorophore and the quencher are linked to different nucleotides in the variant detection probe.

The wild-type detection probe may be linked to at least one fluorophore and at least one quencher, wherein the quencher is capable of quenching the fluorescence of the fluorophore. Preferably, the quencher and the fluorophore are linked to the wild-type detection probe in a manner, so that the quencher is capable of quenching the fluorescence of the fluorophore, when the probe is present in its free state. Thus, frequently the fluorophore and the quencher are positioned sufficiently close to each other, so that the quencher is capable of quenching the fluorescence of the fluorophore. Frequently, the fluorophore and the quencher are linked to different nucleotides in the wild-type detection probe.

In embodiments of the invention employing both a variant detection probe and a wild-type detection probe, then the variant detection probe may be linked to a different fluorophore than the wild-type detection probe. In particular, the variant detection probe may be linked to at least one fluorophore, which has fluorescence, which is distinguishable from the fluorescence of all fluorophores linked to the wild-type detection probe. Similarly, the variant wild-type detection probe may be linked to at least one fluorophore, which has fluorescence, which is distinguishable from the fluorescence of all fluorophores linked to the variant detection probe.

Step g) of the methods of the invention may involve detection of fluorescence from the variant detection probe. Thus, step g) may comprise detecting fluorescence of the fluorophore linked to the variant detection probe. This may for example be the case in embodiments of the invention, wherein:
  the variant probe is linked to at least one fluorophore, and at least one quencher, capable of quenching the fluorescence of the fluorophore;
  the nucleic acid polymerase is a DNA polymerase having 5' to 3' exonuclease activity; and/or
  the method is method of detecting the presence of a variant sequence in a target nucleic acid sequence.

Similarly, step g) of the methods of the invention may involve detection of fluorescence from the wild-type detection probe. Thus, step g) may comprise detecting fluorescence of the fluorophore linked to the wild-type detection probe. This may for example be the case in embodiments of the invention, wherein:
  the wild-type detection probe is linked to at least one fluorophore, and at least one quencher, capable of quenching the fluorescence of the fluorophore;
  the nucleic acid polymerase is a DNA polymerase having 5' to 3' exonuclease activity; and/or
  the method is method of detecting the presence of a target nucleic acid sequence.

In embodiments of the invention, wherein the PCR is partitioned into PCR reactions contained in droplets, then said fluorescence may for example be detected using detector having handling capabilities for droplet samples, with individual droplets entering the detector, undergoing detection, and then exiting the detector. For example, a flow cytometry device can be adapted for use in detecting fluorescence from droplet samples. In some cases, a microfluidic device equipped with pumps to control droplet movement is used to detect fluorescence from droplets in single file. In some cases, droplets are arrayed on a two-dimensional surface and a detector moves relative to the surface, detecting fluorescence at each position containing a single droplet.

Following acquisition of fluorescence detection data, a computer can be used to store and process the data. A computer-executable logic can be employed to perform such functions as subtraction of background fluorescence, assignment of target and/or reference sequences, and quantification of the data. A computer can be useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or patient information useful in the methods described herein.

The detection signal(s) may be created based on detected light emitted by the wild-type detection probe, and optionally from the variant detection probe in the partitions. The variant detection probes may report whether at least one of two or more particular amplification reactions represented by the signal has occurred in a partition and thus whether at least one copy of the variant sequence is present in the partition. The level or amplitude of the signal corresponding to the probes may be analyzed to determine whether or not at least one of the particular reactions has occurred and at least one copy of one of the particular targets is present. The level or amplitude of the signal may vary among the partitions according to the presence of the target nucleic acid sequence is present or absent in each partition. For example, a partition positive for a particular target may produce a signal level or amplitude that is above a given threshold and/or within a given range. Partitions may be analyzed and signals created at any suitable time(s). Exemplary times include at the end of an assay (endpoint assay), when reactions have run to completion and the data no longer are changing, or at some earlier time, as long as the data are sufficiently and reliably separated. In general it may be preferred that detection is done after performing the number of exponential PCR cycles needed for the true-positive signals to have a sufficiently high amplitude.

In one aspect, provided herein is a method for detecting the presence of a target sequence using a single detection probe.

Figure 1B:
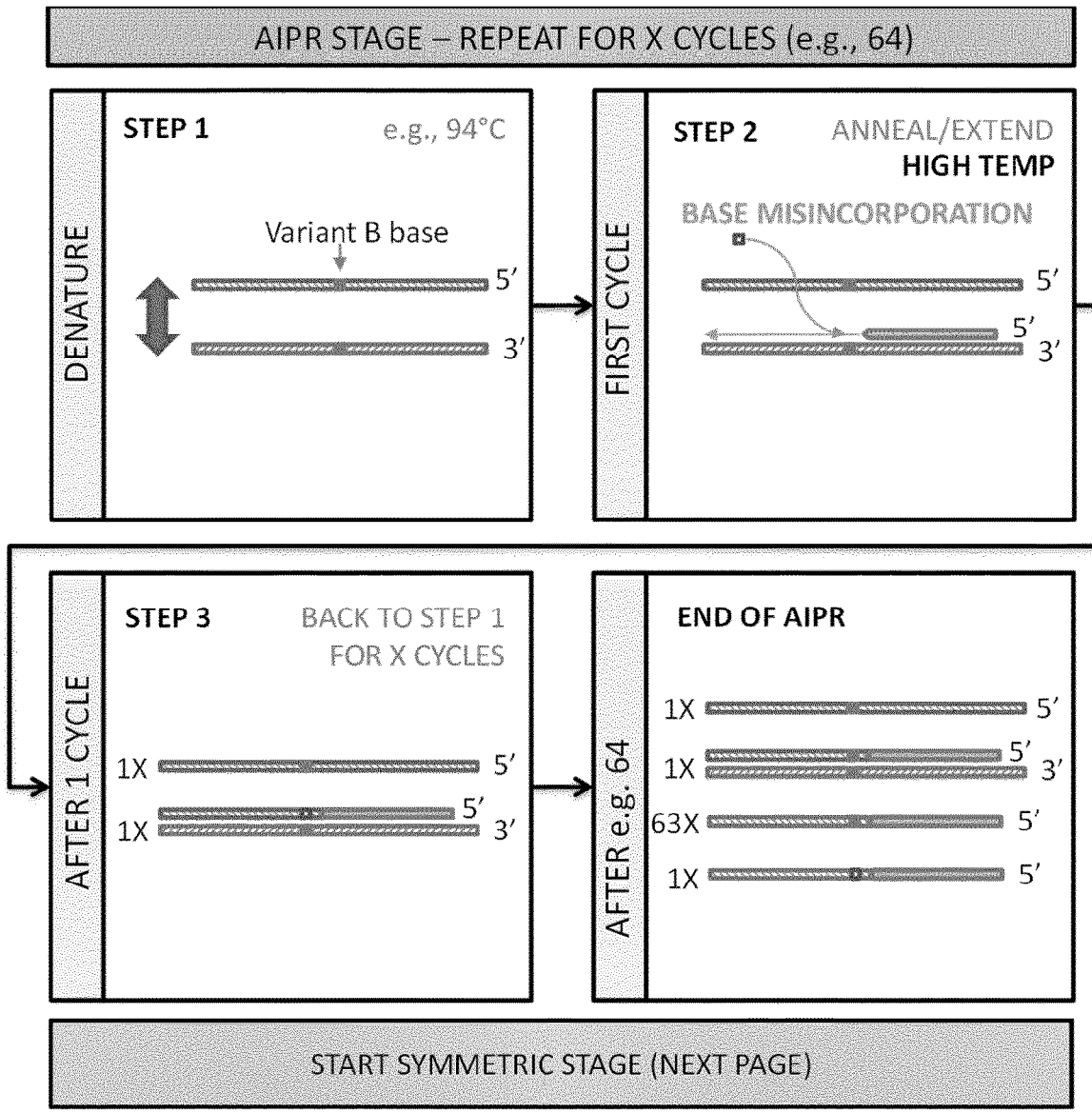
FIG. 1B shows the situation where a wild-type template is present, but a polymerase error occurs. During the AIPR stage several copies of the wild-type sequence are generated, but only one copy of the erroneous mutant sequence. The temperature is kept sufficiently high so that the primer-L and the probes do not anneal. In the symmetric stage both the wild-type DNA and the erroneous mutant DNA are exponentially amplified, however since there are many more copies of wild-type DNA at the onset of the exponential phase, wild-type DNA vastly outnumbers mutant DNA.
Figure 1B:
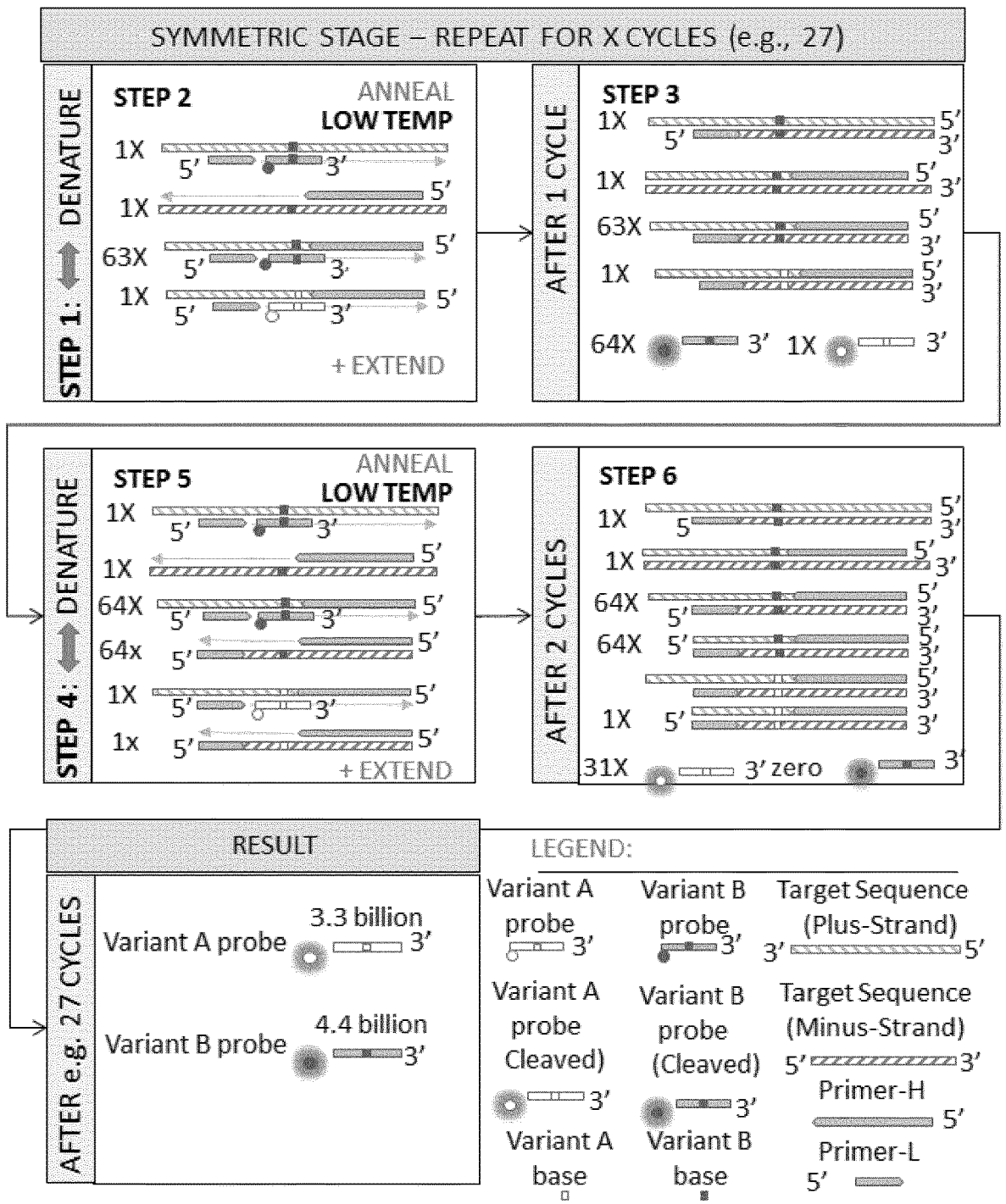
Figure 3A:
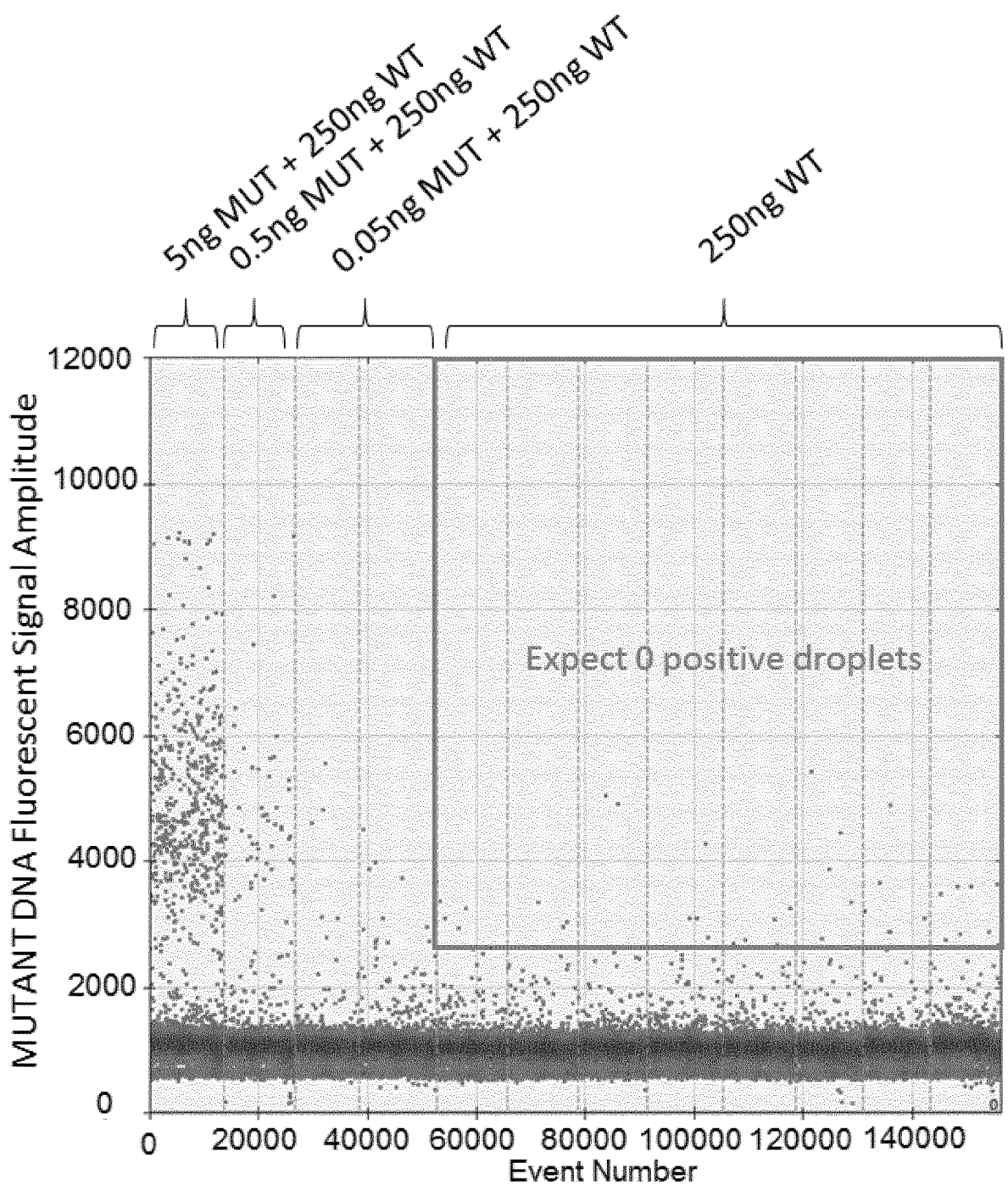
FIG. 3 shows Droplet digital PCR plots. The figure shows the mutant DNA signal obtained from PrimePCR™ Mutation Assay (left side) and IBSAFE assays (right side) for PIK3CA H1047R variant (top half) and PIK3CA E542K variant (bottom half). Droplets (X-axis) are indicated as dots with their fluorescent intensity (Y-axis). Note the lack of false-positive droplets within the negative control wells when using the IBSAFE method (outlined in boxes in the top right corners of each diagram) as compared to the PrimePCR™ Mutation Assay.
Figure 3B:
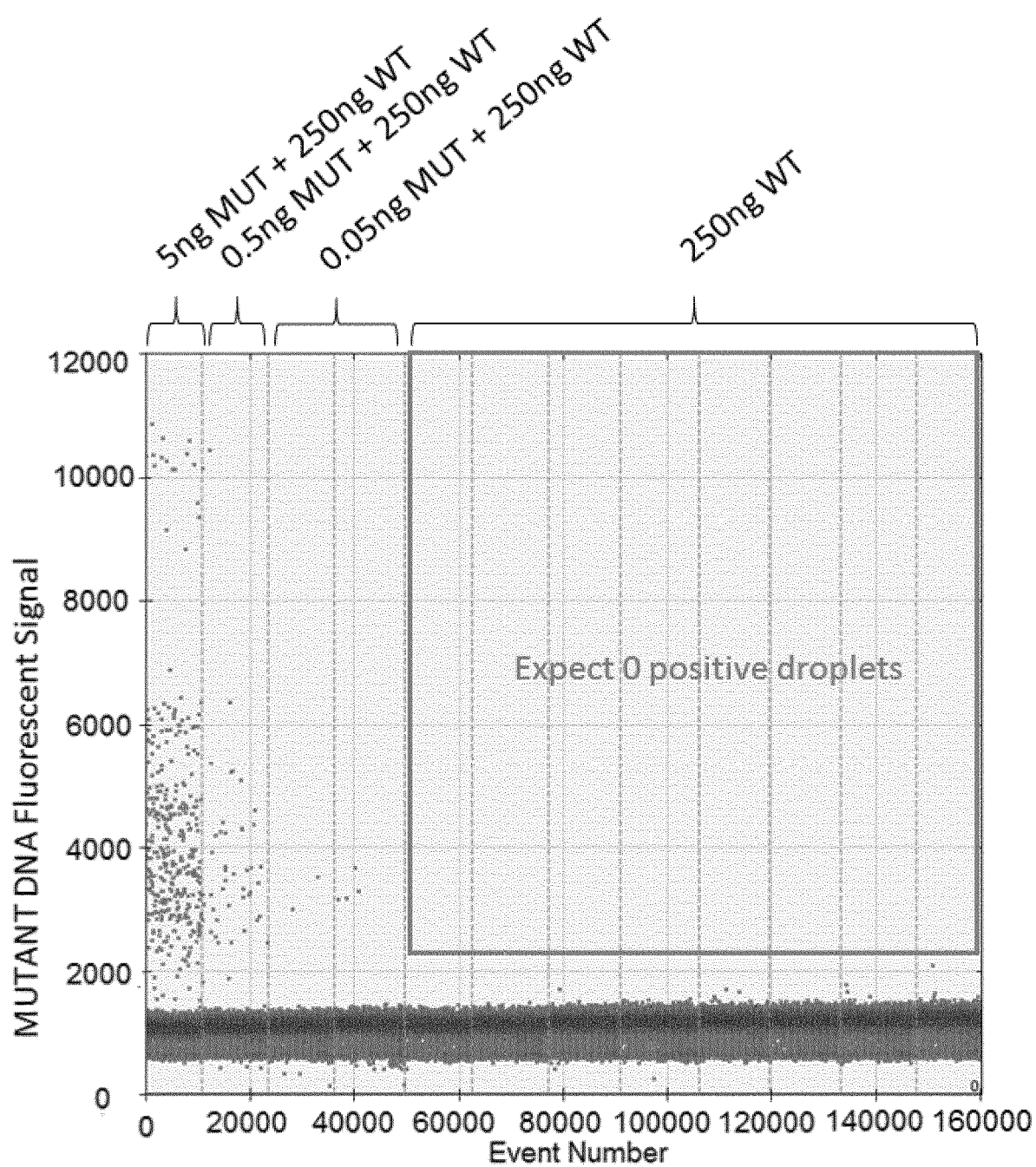
Figure 3C:
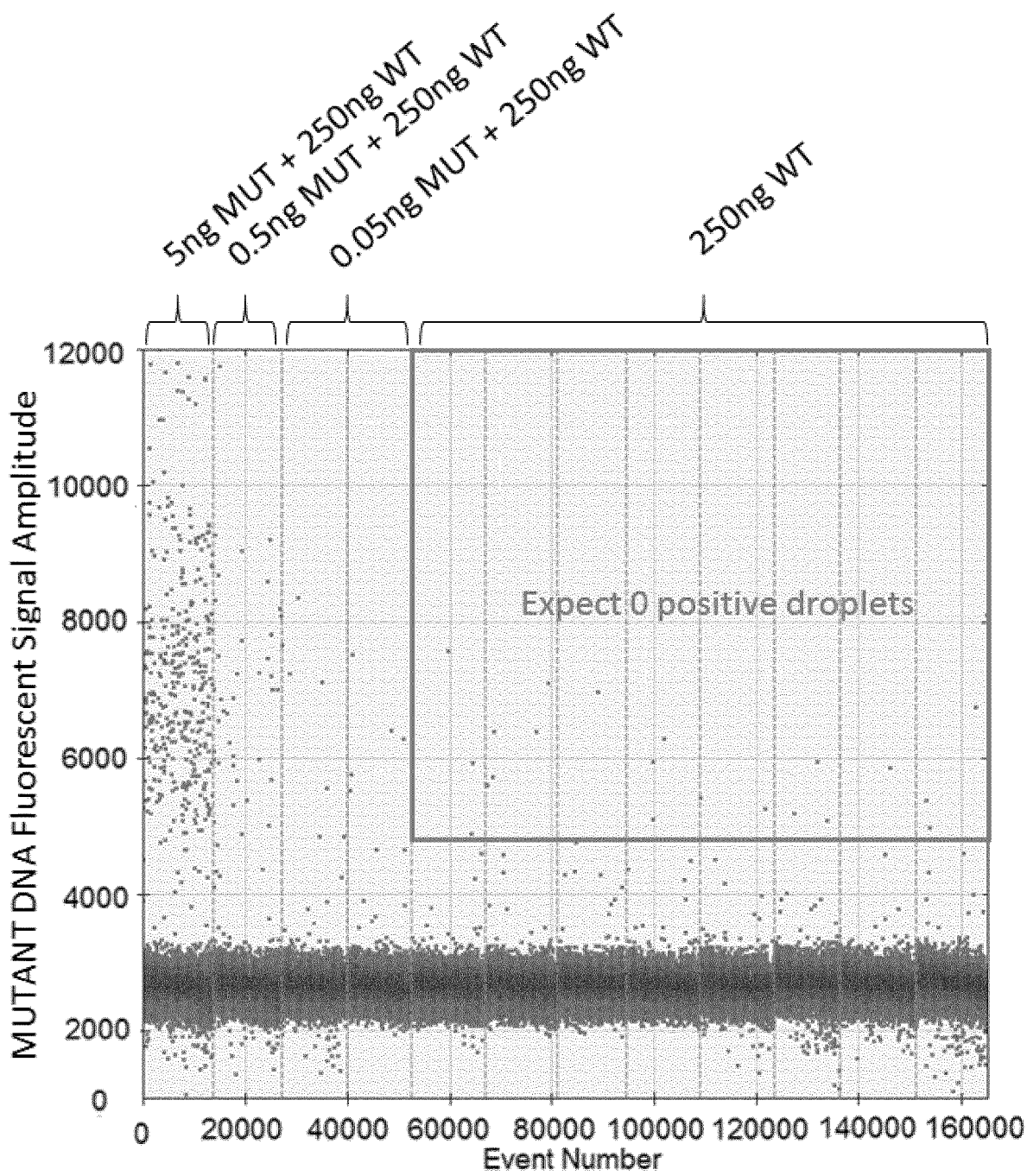
Figure 3D:
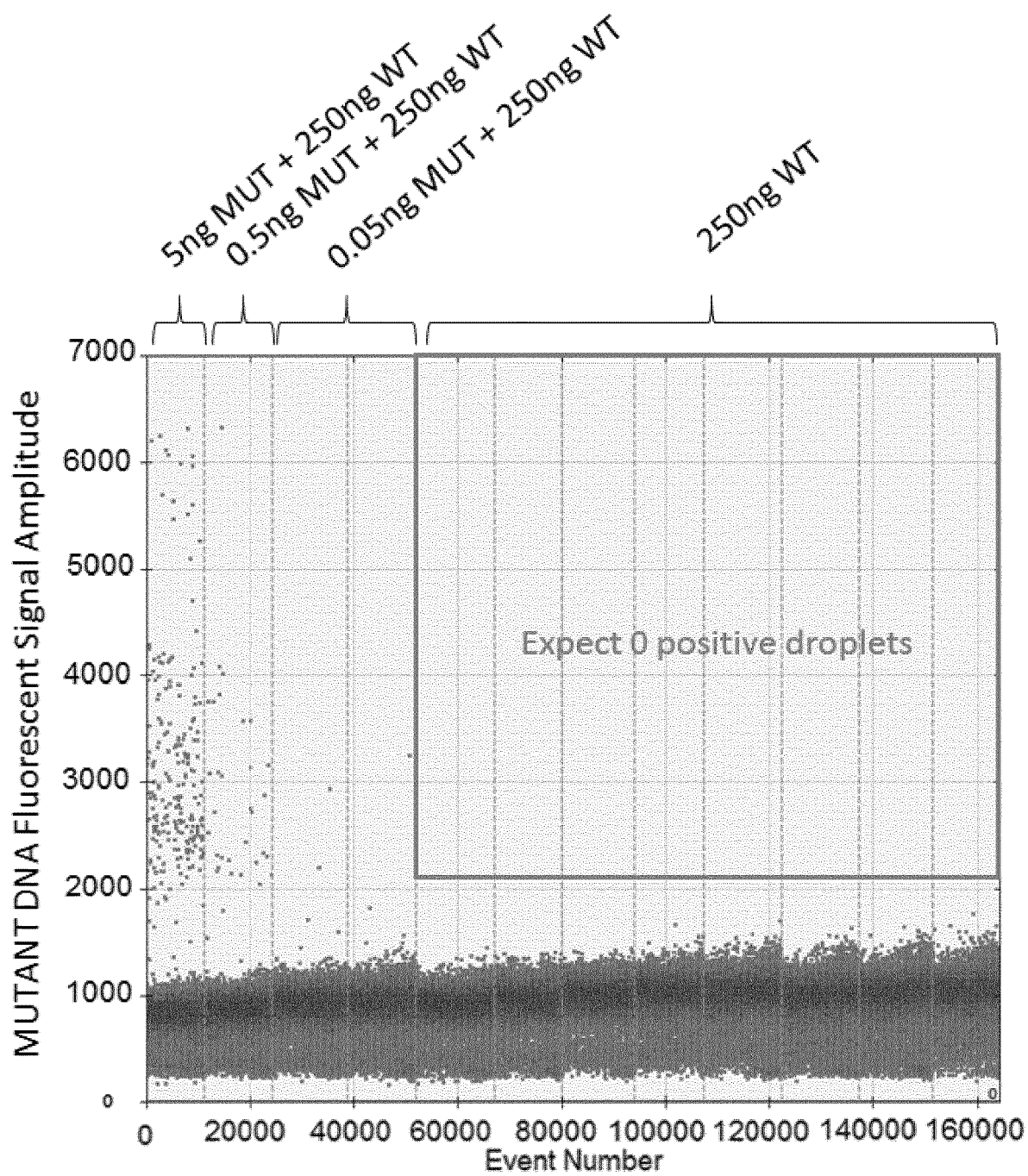

In some cases, the AIPR and the exponential PCR are performed in a dPCR setting, such as ddPCR. Two distinct droplet populations can be detectable and counted to determine the concentration of target nucleic acid sequence comprising a variant sequence (see overview in FIG. 1A) versus not comprising said variant sequence (see FIG. 1B).

The fluorophore as used herein can mean a compound with fluorescent emission, e.g. with a fluorescent emission maximum between about 350 and about 900 nm. A wide variety of fluorophores can be used, including but not limited to: 5-FAM (also called 5-carboxyfluorescein; also called Spiro(isobenzofuran-1(3H), 9'-(9H)xanthene)-5-carboxylic acid,3',6'-dihydroxy-3-oxo-6-carboxyfluorescein); 5-Hexachloro-Fluorescein; ([4,7,2',4',5',7'-hexachloro-(3',6'-dipivaloyl-fluoresceinyl)-6-carboxyli-c acid]); 6-Hexachloro-Fluorescein; ([4,7,2',4',5',7'-hexachloro-(3',6'-dipivaloylfluoresceinyl)-5-carboxylic acid]); 5-Tetrachloro-Fluorescein; ([4,7,2',7'-tetra-chloro-(3',6'-dipivaloylfluoresceinyl)-5-carboxylic acid]); 6-Tetrachloro-Fluorescein; ([4,7,2',7'-tetrachloro-(3',6'-dipivaloylfluoresceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino)naphthalene-1-sulfonic acid); Cy5 (Indodicarbocyanine-5); Cy3 (Indodicarbocyanine-3); and BODIPY FL (2,6-dibromo-4,4-difluoro-5,7-dimethyl-4-bora-3a,4a-diaza-s-indacene-3-proprionic acid); Quasar™-670 dye (Biosearch Technologies); Cal Fluor™ Orange dye (Biosearch Technologies); Rox dyes; Max dyes (Integrated DNA Technologies), as well as suitable derivatives thereof.

Quencher, as used herein, can mean a molecule or part of a compound that is capable of reducing the fluorescence of a fluorophore when attached to or in proximity to the detection probe. Quenching can occur by any of several mechanisms including fluorescence resonance energy transfer, photo-induced electron transfer, paramagnetic enhancement of intersystem crossing, Dexter exchange coupling, and exciton coupling such as the formation of dark complexes. The selection of the quencher can depend on the fluorophore used. A number of commercially available quenchers are known in the art, and include but are not limited to DABCYL, Black Hole™ Quenchers (BHQ-1, BHQ-2, and BHQ-3), Iowa Black™ FQ and Iowa Black™ RQ. These are so-called dark quenchers. They have no native fluorescence, which can eliminate background seen with other quenchers such as TAMRA, which is intrinsically fluorescent.

There is a great deal of practical guidance available in the literature for selecting appropriate reporter-quencher pairs for particular probes, as exemplified by the following references: Clegg, Meth. Enzymol., 211: 353-388 (1992); Wo et al., Anal. Biochem., 218: 1-13 (1994); Pesce et al., editors, Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs, e.g., Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (cited above); Ullman et al., U.S. Pat. No. 3,996,345; Khanna et al., U.S. Pat. No. 4,351,760.

Both the detectable lable (e.g. the fluorophore) and the quencher can be attached to the probe using methods known in the art. In some cases, one of the reporter/quencher pair is attached to the 5' portion of a probe and 5' to the target locus if the probe sequence is complementary to the target locus, and the other of the reporter/quencher pair is attached to the 3' portion of the probe.

Detectable labels and quenchers can be added during oligonucleotide synthesis through standard phosphoramidite chemistry. They can also be added post-synthesis by introducing a linker with an appropriate functional group during oligo synthesis. Following synthesis, a detectable (e.g., fluorophore) can be coupled to an oligonucleotide functional group. For longer sequences, to permit efficient quenching, the sequence immediately 3' of the fluorophore and 5' of the quencher, can be made complementary to each other to permit the formation of a stem of a hairpin (e.g., molecular beacon). Thus, during the annealing phase of AIPR and/or the exponential PCR, such a probe will hybridize to amplified target sequence, thereby physically distancing the detectable label (e.g., fluorophore) from the quencher allowing for higher fluorescence to be detected. However, in the absence of amplified target sequence, the probe creates a hairpin causing the detectable (e.g., fluorophore) and quencher to be close to one another, which limits the fluorescence of the reaction. In these reactions, a polymerase with 5'-3' exonuclease activity is not required to cleave the probe. The proper site of attachment for the signal reporter (e.g., fluorophore) and quencher and the distance between the signal reporter (e.g., fluorophore) and the quencher is known in the art.

In some cases, the detection probe is a TaqMan® probe.

A TaqMan® probe (Heid et. al, 1996) can use the fluorogenic 5' exonuclease activity of Taq polymerase to measure the amount of target sequences in cDNA samples. TaqMan® probes can contain a fluorophore usually at or near the 5' base, and a quencher can be at or near the 3' base. The quencher can be a dye such as TAMRA or can be a non-fluorescent molecule such as 4-(4-dimethylaminophenylazo)benzoic acid (DABCYL). See Tyagi et al., Nature Biotechnology 16:49-53 (1998). When irradiated, the excited fluorescent dye transfers energy to the nearby quenching dye molecule rather than fluorescing (this is called FRET=Forster or fluorescence resonance energy transfer). Thus, the close proximity of the fluorophore and quencher can prevent emission of any fluorescence while the probe is intact. TaqMan® probes can be designed to anneal to an internal region of the PCR product. When the polymerase replicates a template on which a TaqMan® probe is bound, its 5' exonuclease activity can cleave the probe. This cleavage can end the activity of quencher (no FRET) and the reporter dye starts to emit fluorescence which can increase in each cycle proportional to the rate of probe cleavage. Accumulation of PCR products can be detected by monitoring the increase in fluorescence of the fluorophore. Because the cleavage can occur if the detection probe hybridizes to the target nucleic acid sequence, the fluorescence detected can originate from specific amplification. In some cases, the process of hybridization and cleavage does not interfere with the exponential PCR. In some cases, a fluorogenic probe has no G at the 5'-end. A and G adjacent to the reporter dye may quench reporter fluorescence even after cleavage.

In some cases, the detection probe is a molecular beacon. Molecular beacons (MBs) can be oligonucleotides designed for the detection and quantification of target nucleic acids (e.g., target DNAs). 5' and 3' termini of a MB can collectively comprise a pair of moieties which can confer detectable properties on the MB. One of the termini can be attached to a fluorophore and the other can be attached to a quencher molecule capable of quenching a fluorescent emission of the fluorophore. For example, a fluorophore/quencher pair can use a fluorophore such as EDANS or fluorescein, e.g., on the 5'-end and a quencher such as Dabcyl, e.g., on the 3'-end.

When a MB is present free in solution, i.e., not hybridized to a second nucleic acid, the stem of the MB can be stabilized by complementary base pairing. This self-complementary pairing can result in a "hairpin loop" structure for the MB in which the fluorophore and the quenching moieties are proximal to one another. In this confirmation, the fluorescent moiety can be quenched by the fluorophore.

The loop of the molecular beacon can be complementary to or identical to part of the target nucleic acid sequence, such that hybridization of the loop to its complementary sequence in the target forces disassociation of the stem, thereby distancing the fluorophore and quencher from each other. This distancing can result in unquenching of the fluorophore, causing an increase in fluorescence of the MB.

Further details regarding standard methods of making and using MBs are well established in the literature e.g., in Leone et al. (1995) "Molecular beacon probes combined with amplification by NASBA enable homogenous real-time detection of RNA." Nucleic Acids Res. 26:2150-2155; Tyagi and Kramer (1996) "Molecular beacons: probes that fluoresce upon hybridization" Nature Biotechnology 14:303-308; Blok and Kramer (1997), and U.S. Pat. No. 6,548,254.

The detection probe may also be a Scorpions™ probe. A Scorpions™ probe can provide a FRET-based stem-loop detection mechanism similar to Molecular Beacon, except that the probe also has a segment attached that serves as an amplification primer (see e.g., Whitcombe et al. Nat. Biotechnol. 1999, Aug. 17(8): 804-7; U.S. Pat. No. 6,326,145). In some cases, the probe may be a Sunrise™ probe. A Sunrise™ probe can comprise a primer attached to a hairpin probe that is extended during amplification. This arrangement can separate the internal quencher label from the 5' terminal fluorophore (Nazarenko et al., Nucl. Acids Res. 1997, 25: 2516-2521).

The 3' terminal nucleotide of the oligonucleotide probe can be blocked or rendered incapable of extension by a nucleic acid polymerase. Such blocking can be conveniently carried out by the attachment of a reporter or quencher molecule to the terminal 3' carbon of the oligonucleotide probe by a linking moiety.

In some cases, a reference probe may be included in the partitioned PCR reactions. A reference probe can be a nonspecific reference probe or a specific reference probe. The reference probe can hybridize to a reference locus.

In one embodiment, the methods of the invention involve using a single primer pair consisting of primer-H and primer-L combined with one detection probe, such as a variant detection probe or a wild-type detection probe. In other embodiments of the invention the methods involve using a single primer pair consisting of primer-H and primer-L combined with two detection probes, which are a variant detection probe and a wild-type detection probe.

In one embodiment detection is performed by the aid of a detection reagent, which is a dye. The dye may for example be a major groove binder, a minor groove binder, an intercalator, or an external binder, among others. Exemplary dyes that may be suitable include luminescent cyanines, phenanthridines, acridines, indoles, imidazoles, and the like, such as DAPI, Hoechst® 33258 dye, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others.

As used herein "a probe capable of detecting a specific mutation" is typically a probe comprising a consecutive sequence of the target sequence comprising said mutation or a complementary sequence thereof.

Method of Predicting the Presence of a Clinical Condition

The methods of the invention may have a plethora of various applications. In fact, the methods are useful in any application, where it is desirable to detect the presence of a target nucleic acid sequence, and/or to distinguish between target nucleic acid sequences comprising or not comprising a variant sequence.

For example the methods may be useful for forensic application, where analysis of nucleic acids on a very limited material often is made. The methods may for example be used in preparing fingerprints of genetic material to determine the presence of particular polymorphisms.

One very useful application of the methods of the invention is for predicting the presence of a clinical condition in an individual.

Many clinical conditions are associated with the presence of particular target nucleic acid sequences. Some clinical conditions are characterised by the presence of a variant sequence in a target nucleic acid. Other clinical conditions are associated with markers, e.g. the presence of a variant sequence may be an indicator of the clinical conditions.

Thus, in one embodiment the invention relates to methods of predicting the presence of a clinical condition in an individual, wherein said clinical condition is linked to the presence of a variant sequence in a target nucleic acid sequence, said method comprising the steps of
 a) providing a sample from said individual comprising template nucleic acids
 b) performing the methods of detection of a variant sequence in a target nucleic acid sequence described herein wherein the presence of said variant sequence in said target nucleic acid is indicative of the presence of said clinical condition.

Many clinical conditions are associated with the presence of one or more variant sequence(s). Thus, the clinical condition may be any clinical condition linked to the presence of a variant sequence in a target nucleic acid sequence.

The variant sequence may a biomarker, which correlates with e.g. the presence of a clinical condition, the risk of progression of a clinical condition, with the susceptibility of the clinical condition to a given treatment, or with the risk of death. Thus, the variant sequence may be correlated to a prediction in relation to a clinical condition.

In one embodiment of the invention, the clinical condition is cancer. Said cancer may be any cancer, e.g. a cancer selected from the group consisting of carcinoma of the breast, colorectal, pancreas, stomach, GIST, hepatocellular, lung, small cell lung, ovarian, uterine, cervix, bladder, renal, prostate, testis, thyroid carcinoma, malignant melanoma, osteosarcoma, chondrosarcoma, myosarcoma, glioblastoma or other brain tumors, head/neck other gastrointestinal and germ cell tumors, and haematologic malignancies.

The variant sequence may be linked to said cancer. For example the presence of the variant sequence may be indicative of the presence of said cancer. However, frequently additional investigation will be required to determine whether said individual is suffering from said cancer.

The table below provides non-limiting examples of mutations linked to cancer, the presence of which can be detected using the methods of the invention. However, the skilled person will be aware of numerous other mutations linked to cancer that can be detected using the methods of the invention.

| Clinical condition | Protein | UniProt accession No. | RefSeq ID | CCDS ID | Mutation(s) |
|---|---|---|---|---|---|
| Breast cancer | PIK3CA | P42336 | NM_006218 | CCDS43171 (SEQ ID NO: 69) | H1047R, E542K, E545K |
| Melanoma | BRAF | P15056 | NM_004333 | CCDS5863 (SEQ ID NO: 70) | V600E |
| Lung cancer | EGFR | P00533 | NM_005228 | CCDS5514 (SEQ ID NO: 71) | L858R, T790M |
| Colorectal cancer | KRAS | P01116 | NM_004985 | CCDS8702 (SEQ ID NO: 72) | G12D, G12V, G12C, G13D |

The mutations above are indicated at the protein level. The first letter indicates the wild-type amino acid, the number is the position of the amino acid, and the last letter the replacement amino acid found in the mutant. Thus, by way of example H1047R indicates that the histidine at amino acid number 1047 has been replaced by arginine. IUPAC one letter codes or three letter codes for amino acids are used herein.

The invention may thus relate to methods and kits-of-part comprising (use) a pair of primers, wherein
- the primer-H comprises a consecutive sequence of in the range of 50 to 100 nucleotides of SEQ ID NO:69, 70, 71 or 72 and primer-L comprises a consecutive sequence of in the range of 10 to 20 nucleotide of the sequence complementary to SEQ ID NO:69, 70, 71 or 72; OR
- the primer-H comprises a consecutive sequence of in the range of 50 to 100 nucleotides of the sequence complementary to SEQ ID NO:69, 70, 71 or 72 and primer-L comprises a consecutive sequence of in the range of 10 to 20 nucleotide of SEQ ID NO:69, 70, 71 or 72;
- and wherein primer-H and primer-L together are capable of amplifying a target sequence comprising at least one of the nucleotides encoding any of the mutations mentioned herein.

In one embodiment the invention provides methods of predicting the presence of a clinical condition in an individual, wherein said clinical condition is linked to the presence of a target nucleic acid sequence, said method comprising the steps of
a) providing a sample from said individual comprising template nucleic acids
b) performing the methods of detection of a variant sequence in a target nucleic acid sequence described herein
wherein the presence of said target nucleic acid is indicative of the presence of said clinical condition.

The clinical condition is infection by an infectious pathogen in which case the target nucleic acid for example may be a nucleic acid sequence from the genome of said pathogen.

The sample may be any sample from said individual. In particular, the sample should be a sample comprises template nucleic acids. In embodiments of the invention, wherein the clinical condition is cancer it is preferred that the sample comprises DNA from cancer cells. Thus, the sample may comprise cancer cells comprising DNA and/or the sample may comprise free DNA derived from cancer cells.

The sample may for example be selected from the group consisting of blood samples, biopsies, faeces samples, saliva samples, urine samples, vaginal fluid samples, ascites fluid samples, cerebrospinal fluid samples, and tissue exudate sample. The sample may also be a fraction of any of the aforementioned. For example the sample may be a blood sample or a fraction thereof, such as a plasma sample or a serum sample.

The template nucleic acids may be any nucleic acids comprised in the sample, e.g. genomic DNA or RNA. The template nucleic acids may also be cDNA prepared based on the RNA present in the sample.

In one embodiment the template nucleic acids are selected from the group consisting of cell-free DNA, nucleosomal DNA, and circulating tumor DNA (ctDNA), which may be found in the blood circulation and other bodily fluids.

The sample according to the present invention may be extracted from an individual and used for the methods of the invention.

The individual may be any animal, such as a mammal, including human beings. In a preferred embodiment, the individual is a human being.

EXAMPLES

The invention is further illustrated by the following examples, which however should not be construed as being limiting for the invention.

Items

The invention may further be defined by the following items:
1. A method for detection of the presence of a variant sequence in a target nucleic acid sequence in a sample comprising the steps of
   a) providing a sample comprising template nucleic acids
   b) providing a set of primers comprising at least a pair of primers specifically capable of amplification of the target nucleic acid sequence, wherein the set of primers at least comprises a primer-H and a primer-L, wherein the melting temperature of primer-H is at least 10° C. higher than the melting temperature of primer-L, and wherein primer-L contains a sequence complementary to a fragment of the elongation product of primer-H,
   c) providing a nucleic acid polymerase having polymerase activity at an elongation temperature,
   d) preparing partitioned PCR reactions each comprising a part of the sample, the set of primers, the nucleic acid polymerase, PCR reagents and optionally detection reagents
   e) performing an asymmetric incremental polymerase reaction (AIPR) comprising the steps of:
      i. incubating the partitioned PCR reactions at a denaturation temperature, thereby denaturing DNA to single-stranded molecules
      ii. incubating the partitioned PCR reactions at a high annealing temperature allowing annealing of primer-H, but not of primer-L,
      iii. optionally incubating the partitioned PCR reactions at the elongation temperature,
      iv. optionally repeating steps i to iii,
   f) performing a polymerase chain reaction (PCR) comprising the steps of:
      I. incubating the partitioned PCR reactions at a denaturation temperature, thereby denaturing DNA to single-stranded molecules
      II. incubating the PCR at a low annealing temperature allowing annealing of both primer-H and primer-L,
      III. incubating the PCR at the elongation temperature thereby allowing extension of all annealed primers
      IV. optionally repeating steps II to IV, thereby obtaining a PCR product
   g) detecting whether the PCR product comprises the variant sequence in the target nucleic acid sequence.
2. The method according to item 1, wherein step e) results in amplification of only one strand of the target nucleic acid sequence.
3. The method according to any one of the preceding items, wherein step f) results in amplification of both strands of the target nucleic acid sequence, thereby obtaining a PCR product.
4. The method according to any one of the preceding items, wherein the variant sequence is a single nucleotide mutation.
5. The method according to any one of items 1 to 3, wherein the variant sequence is a single nucleotide polymorphism (SNP).

6. The method according to any one of the preceding items, wherein the PCR product may comprise both the target nucleic acid sequence comprising the variant sequence and the target nucleic acid sequence not having the variant sequence.
7. A method for detection of the presence of a target nucleic acid sequence in a sample comprising the steps of
   a) providing a sample comprising template nucleic acids
   b) providing a set of primers comprising at least a pair of primers specifically capable of amplification of the target nucleic acid sequence, wherein the set of primers at least comprises a primer-H and a primer-L, wherein the melting temperature of primer-H is at least 10° C. higher than the melting temperature of primer-L, and wherein primer-L contains a sequence complementary to the elongation product of primer-H,
   c) providing a nucleic acid polymerase having polymerase activity at an elongation temperature, which is higher than the melting temperature of primer-H,
   d) preparing partitioned PCR reactions each comprising a part of the sample, the set of primers, the nucleic acid polymerase, PCR reagents and optionally detection reagents
   e) performing an asymmetric incremental polymerase reaction (AIPR) comprising the steps of:
      i. incubating the partitioned PCR reactions at a denaturation temperature, thereby denaturing DNA to single-stranded molecules
      ii. incubating the partitioned PCR reactions at a high annealing temperature allowing annealing of primer-H, but not of primer-L,
      iii. optionally incubating the partitioned PCR reactions at the elongation temperature,
      iv. optionally repeating steps i to iii,
   f) performing a polymerase chain reaction (PCR) comprising the steps of:
      I. incubating the partitioned PCR reactions at a denaturation temperature, thereby denaturing DNA to single-stranded molecules
      II. incubating the PCR at a low annealing temperature allowing annealing of both primer-H and primer-L,
      III. incubating the PCR at the elongation temperature thereby allowing extension of all annealed primers
      IV. optionally repeating steps II to IV, thereby obtaining a PCR product
   g) detecting whether the PCR product comprises the target nucleic acid sequence.
8. The method according to any one of the preceding items, wherein the AIPR of step e) comprises the steps of:
   i. incubating the partitioned PCR reactions at a denaturation temperature, thereby denaturing DNA to single-stranded molecules
   ii. incubating the partitioned PCR reactions at a high annealing temperature allowing annealing of primer-H, but not of primer-L, wherein the high annealing temperature also is the elongation temperature, thereby allowing for extension of the annealed primer-H;
   iii. repeating steps i to ii.
9. The method according to any one of items 1 to 7, wherein the AIPR of step e) comprises the steps of:
   i. incubating the partitioned PCR reactions at a denaturation temperature, thereby denaturing DNA to single-stranded molecules
   ii. incubating the partitioned PCR reactions at a high annealing temperature allowing annealing of primer-H, but not of primer-L,
   iii. incubating the partitioned PCR reactions at the elongation temperature, thereby allowing elongation of the annealed primer-H,
   iv. repeating steps i to iii.
10. The method according to any one of the preceding items, wherein primer-H is the only primer in the set of primers that has a melting temperature at least 10° C. higher than the melting temperature of primer-L.
11. The method according to any one of the preceding items, wherein the set of primers consists of the primer-H and the primer-L, and wherein the primer-H and primer-L are specifically capable of amplification of the target nucleic acid sequence.
12. The method according to any one of the preceding items, wherein the primer-H is identical to the sequence at the 5'-end of the target nucleic acid sequence and the primer-L is identical to the complementary sequence of the 3'-end of the target nucleic acid sequence.
13. The method according to any one of the preceding items, wherein step e) results in elongation of primer-H, but in no detectable elongation of primer-L.
14. The method according to any one of the preceding items, wherein step e) results in elongation of primer-H, but in no detectable elongation of any other primer.
15. The method according to any one of the preceding items, wherein the melting temperature of primer-H is at least 15° C. higher than the melting temperature of primer-L.
16. The method according to any one of the preceding items, wherein the melting temperature of the primer-H is at least 16° C. higher, preferably at least 18° C. higher, such as at least 20° C. higher, for example in the range of 15 to 50° C., such as in the range of 15 to 25° C. higher than the melting temperature of the primer-L.
17. The method according to any one of the preceding items, wherein the melting temperature of the primer-H is in the range of 60 to 90° C. for example in the range of 60 to 80° C., preferably in the range of 70 to 85° C., such as in the range of 70 to 80° C.
18. The method according to any one of the preceding items, wherein the melting temperature of the primer-L is in the range of 30 to 55° C., such as in the range of 35 to 55° C., preferably in the range of 40 to 50° C.
19. The method according to any one of the preceding items, wherein primer-H has a melting temperature at least 15° C. higher than the melting temperature of any other primer within the set of primer, which together with Primer-H is capable of amplification of the target nucleic acid sequence
20. The method according to any one of the preceding items, wherein the set of primers do not comprise any primers:
   a) which have a melting temperature which is in the range of +/−15° C., preferably in the range of +/−20° C., such as in the range of +/−25° C. of the melting temperature of primer-H; and
   b) which together with primer-H can constitute a pair of primers specifically capable of amplification of the target nucleic acid sequence.
21. The method according to any one of the preceding items, wherein the set of primers comprise more than one primer-H, and any primer, which together with any of the primer-H forms a pair of primers, have a melting temperature, which is at least 15° C. lower than the melting temperature of the primer-H of that pair of primers.

22. The method according to any one of the preceding items, where Primer-H comprise one or more nucleotide analogues, for example one or more LNAs.

23. The method according to any one of the preceding items, wherein the partitioned PCR reactions each comprises in average at the most 10, such as at the most 5 template nucleic acids comprising the target nucleic acid sequence.

24. The method according to any one of the preceding items, wherein the partitioned PCR reactions each are contained in droplets prepared using a droplet generator.

25. The method according to any one of the preceding items, wherein the partitioned PCR reactions each are contained in a droplet of a volume in the range of 1 to 10,000 picoliters, for example approximately 1000 picoliters.

26. The method according to any one of items 1 to 23, wherein the partitioned PCR reactions are contained in microtiter plates.

27. The method according to any one of the preceding items, wherein step e) comprises repeating steps i. to iii. for in the range of 8 to 256 times, preferably for in the range of 16 to 128 times, for example for in the range of 32 to 128 times, for examples approximately 64 times, such as 64 times.

28. The method according to any one of item 9 and 10 to 27, wherein step e) comprises repeating steps i. to iii. for in the range of 8 to 256 times, preferably for in the range of 16 to 128 times, for example for in the range of 32 to 128 times, for examples approximately 64 times, such as 64 times.

29. The method according to any one of the preceding items wherein the high annealing temperature in step e) is at least 10° C. higher, preferably at least 15° C. higher, for example at least 20° C. higher than the melting temperature of primer-L.

30. The method according to any one of the preceding items, wherein step f) comprises repeating steps I. to Ill. for in the range of 15 to 60 times, preferably for in the range of 20 to 40 times, for example for in the range of 20 to 30 times, for examples in the range of 25 to 30 times.

31. The method according to any one of the preceding items, wherein primer-L is a mismatch modified primer-L and the method comprises a step of low temperature PCR between steps e) and f), wherein the low temperature PCR comprises the steps of:
I. incubating the partitioned PCR reactions at a denaturation temperature, thereby denaturing DNA to single-stranded molecules
II. incubating the PCR at a very low annealing temperature allowing annealing of both primer-H and of the non-mismatched part of primer-L,
III. incubating the PCR at the elongation temperature thereby allowing extension of all annealed primers
IV. optionally repeating steps I to III, thereby obtaining a PCR product.

32. The method according to item 31, wherein the very low annealing temperature is at least 5° C. lower than the low annealing temperature.

33. The method according to any one of items 31 to 32, wherein the very low annealing temperature is at least 20° C. lower than the low annealing temperature.

34. The method according to any one of items 31 to 33, wherein primer-L is an oligonucleotide consisting of:
a 5' sequence of 1 to 10 nucleotides; and
a consecutive sequence in the range of 7 to 15 nucleotides, which is identical to or complementary to a fragment of the target nucleic acid sequence.

35. The method according to any one of the preceding items, wherein the partitioned PCR reactions each contains a detection reagent, which is a variant detection probe, said variant detection probe being capable of hybridizing to the target nucleic acid sequence containing the variant sequence with significantly higher affinity than to the target nucleic acid sequence not containing the variant sequence.

36. The method according to any one of the preceding items, wherein the partitioned PCR reactions each contains a detection reagent which is a wild-type detection probe, said wild-type detection probe being capable of hybridizing to the target nucleic acid sequence not containing the variant sequence.

37. The method according to any one of items 35 and 36, wherein each partitioned PCR reaction contains a variant detection probe and a wild-type detection probe.

38. The method according to any one of items 35 to 37, wherein the variant detection probe is linked to a fluorophore and a quencher, wherein the quencher is capable of quenching the fluorescence of the fluorophore, and wherein the fluorophore and the quencher are linked to different nucleotides in the probe.

39. The method according to any one of items 36 to 38, wherein the wild-type detection probe is linked to a fluorophore and a quencher, wherein the quencher is capable of quenching the fluorescence of the fluorophore, and wherein the fluorophore and the quencher are linked to different nucleotides in the probe.

40. The method according to any one of items 37 to 39, wherein the variant detection probe is linked to a different fluorophore than the wild-type detection probe.

41. The method according to any one of items 35 to 40, wherein step g) comprises detecting fluorescence of the fluorophore linked to the variant detection probe.

42. The method according to any one of the preceding items, wherein the primer-H is selected from the group consisting of primer-H listed in table 3.

43. The method according to any one of the preceding items, wherein the primer-L is selected from the group consisting of primer-L listed in table 3.

44. The method according to any one of items 35 to 43, wherein the variant detection probe is selected from the group consisting of Probe-MUT listed in table 3.

45. The method according to any one of items 36 to 44, wherein the wild-type detection probe is selected from the group consisting of Probe-WT listed in table 3.

46. A method of predicting the presence of a clinical condition in an individual, wherein said clinical condition is linked to the presence of a variant sequence in a target nucleic acid sequence, said method comprising the steps of
providing a sample from said individual comprising template nucleic acids performing the method according to any one of items 1 to 45 wherein the presence of said variant sequence in said target nucleic acid is indicative of the presence of said clinical condition.
47. The method according to item 46, wherein the clinical condition is cancer.
48. The method according to item 46, wherein the mutation is a mutation associated with cancer.
49. The method according to any one of items 45 to 48, wherein the sample is a blood sample or a fraction thereof, and the template nucleic acids are selected from the group consisting of cell-free DNA, nucleosomal DNA and circulating tumor DNA.
50. The method according to any one of items 45 to 49, wherein the sample is selected from the group consisting of saliva samples, urine samples, vaginal fluid samples, ascites fluid sample, cerebrospinal fluid samples and tissue exudate samples.
51. The method according to any one of items 45 to 50, wherein the mutation is selected from the group consisting of:
  A. a mutation in PIK3CA, such as any one of the mutations H1047R or E542K or E545K;
  B. a mutation in BRAF, such as V600E;
  C. a mutation in KRAS, such as any one of the mutations G12D, G12V, G12C or G13D; and
  D. a mutation in EGFR, such as any one of the mutations L858R or T790M.
52. The method according to any one of items 45 to 50, wherein the mutation is selected from the group consisting of the mutations listed in Table 3.
53. A method of predicting the presence of a clinical condition in an individual, wherein said clinical condition is linked to the presence of a target nucleic acid sequence, said method comprising the steps of
  providing a sample from said individual comprising template nucleic acids
  performing the method according to any one of items 7 to 45 wherein the presence of said target nucleic acid is indicative of the presence of said clinical condition.
54. The method according to item 53, wherein the clinical condition is infection by an infectious pathogen.
55. The method according to item 54, wherein the target nucleic acid is a nucleic acid sequence from the genome of said pathogen.
56. A kit-of-parts comprising:
  a set of primers comprising at least a pair of primers specifically capable of amplification of a target nucleic acid sequence, wherein the set of primers at least comprises a primer-H and a primer-L, wherein the melting temperature of primer-H is at least 10° C. higher than the melting temperature of primer-L, and wherein primer-L contains a sequence complementary to the elongation product of primer-H,
  a detection probe being capable of hybridizing to the target nucleic acid sequence, said probe being linked to at least one fluorophore and at least one quencher
  a nucleic acid polymerase;
  PCR reagents;
  reagents for preparing droplets containing partitioned PCR reactions.
57. The kit-of-parts according to item 56, wherein the set of primers is as defined in any one of items 10 to 22.
58. The kit-of-parts according to any one of items 56 to 57, wherein primer-H is as defined in any one of items 10 to 22.
59. The kit-of-parts according to any one of items 56 to 58, wherein primer-L is as defined in any one of items 10 to 22.
60. The kit-of-parts according to any one of items 56 to 59, wherein the detection probe is as defined in any one of items 35 to 45.
61. The kit-of-parts according to any one of items 56 to 60, wherein the primer-H is selected from the group consisting of primer-H listed in table 3.
62. The kit-of-parts according to any one items 56 to 61, wherein the primer-L is selected from the group consisting of primer-L listed in table 3.
63. The kit-of-parts according to any one of items 56 to 62, wherein the variant detection probe is selected from the group consisting of Probe-MUT listed in table 3.
64. The kit-of-parts according to any one of items 56 to 63, wherein the wild-type detection probe is selected from the group consisting of Probe-WT listed in table 3.
65. The kit-of-parts according to any one of items 56 to 60, wherein
  the primer-H comprises a consecutive sequence of in the range of 50 to 100 nucleotides of SEQ ID NO:69 and primer-L comprises a consecutive sequence of in the range of 10 to 20 nucleotide of the sequence complementary to SEQ ID NO:69; OR
  the primer-H comprises a consecutive sequence of in the range of 50 to 100 nucleotides of the sequence complementary to SEQ ID NO:69, and primer-L comprises a consecutive sequence of in the range of 10 to 20 nucleotide of SEQ ID NO:69;
  and wherein primer-H and primer-L together are capable of amplifying a target sequence comprising at least one of the nucleotides 3140, 1624 or 1633 of SEQ ID NO:69.
66. The kit-of-parts according to item 65, wherein the kit-of-parts comprise a probe capable of detecting:
  an A to G mutation of nucleotide 3140 of SEQ ID NO:69;
  a G to A mutation of nucleotide 1624 of SEQ ID NO:69; and/or
  a G to A mutation of nucleotide 1633 of SEQ ID NO:69.
67. The kit-of-parts according to any one of items 56 to 60, wherein
  the primer-H comprises a consecutive sequence of in the range of 50 to 100 nucleotides of SEQ ID NO:70 and primer-L comprises a consecutive sequence of in the range of 10 to 20 nucleotide of the sequence complementary to SEQ ID NO:70; OR
  the primer-H comprises a consecutive sequence of in the range of 50 to 100 nucleotides of the sequence complementary to SEQ ID NO:70, and primer-L comprises a consecutive sequence of in the range of 10 to 20 nucleotide of SEQ ID NO:70;
  and wherein primer-H and primer-L together are capable of amplifying a target sequence comprising nucleotide 1799 of SEQ ID NO:70.
68. The kit-of-parts according to item 67, wherein the kit-of-parts comprise a probe capable of detecting a T to A mutation of nucleotide 1799 of SEQ ID NO:70.

69. The kit-of-parts according to any one of items 56 to 60, wherein
the primer-H comprises a consecutive sequence of in the range of 50 to 100 nucleotides of SEQ ID NO:71 and primer-L comprises a consecutive sequence of in the range of 10 to 20 nucleotide of the sequence complementary to SEQ ID NO:71; OR
the primer-H comprises a consecutive sequence of in the range of 50 to 100 nucleotides of the sequence complementary to SEQ ID NO:71, and primer-L comprises a consecutive sequence of in the range of 10 to 20 nucleotide of SEQ ID NO:71;
and wherein primer-H and primer-L together are capable of amplifying a target sequence comprising at least one of nucleotides 2573 or 2369 of SEQ ID NO:71.
70. The kit-of-parts according to item 69, wherein the kit-of-parts comprise a probe capable of detecting:
a T to G mutation of nucleotide 2573 of SEQ ID NO:71; and/or
a C to T mutation of nucleotide 2369 of SEQ ID NO:71.
71. The kit-of-parts according to any one of items 56 to 60, wherein
the primer-H comprises a consecutive sequence of in the range of 50 to 100 nucleotides of SEQ ID NO:72 and primer-L comprises a consecutive sequence of in the range of 10 to 20 nucleotide of the sequence complementary to SEQ ID NO:72; OR
the primer-H comprises a consecutive sequence of in the range of 50 to 100 nucleotides of the sequence complementary to SEQ ID NO:72, and primer-L comprises a consecutive sequence of in the range of 10 to 20 nucleotide of SEQ ID NO:72;
and wherein primer-H and primer-L together are capable of amplifying a target sequence comprising at least nucleotide 34, 35 or 38 of SEQ ID NO:72.
72. The kit-of-parts according to item 71, wherein the kit-of-parts comprise a probe capable of detecting:
a G to A mutation of nucleotide 38 of SEQ ID NO:72;
a G to T mutation of nucleotide 34 of SEQ ID NO:72;
a G to C mutation of nucleotide 34 of SEQ ID NO:72;
a G to A mutation of nucleotide 34 of SEQ ID NO:72;
a G to T mutation of nucleotide 35 of SEQ ID NO:72;
a G to C mutation of nucleotide 35 of SEQ ID NO:72; and/or
a G to A mutation of nucleotide 35 of SEQ ID NO:72.
73. The kit of parts according to any one of items 65 to 73, wherein Primer-H consists of said consecutive sequence of in the range of 50 to 100 nucleotides, wherein up to 20, such as up to 15, for example up to 10 nucleotides may have been substituted with a nucleotide analogue, for example LNA.
74. The kit of parts according to any one of items 65 to 73, wherein Primer-H consists of a consecutive sequence of in the range of 50 to 100 nucleotides, for example of in the range of 50 to 75 nucleotides of said SEQ ID NO.
75. The kit of parts according to any one of items 65 to 74, wherein Primer-L consists of said consecutive sequence of in the range of 10 to 20 nucleotides and up to 10 additional nucleotides.
76. The method according to any one of items 1 to 55, wherein the method is performed using the kit-of-parts according to any one of items 55 to 75.

EXAMPLES

The invention is further illustrated by the following Examples, which however should not be construed as limiting for the invention.

Example 1

IBSAFE (Incremental Before, Symmetric After, Fidelity Enhanced) Methods

The IBSAFE method is an innovative method to reliably diminish the consequence of any potential DNA polymerase errors so that true-positive reactions have a consistent signal advantage over false-positive reactions.

The present example describes the IBSAFE method within a droplet digital PCR setup using target-specific primer pairs and fluorescent probes that discriminate between variant (e.g. mutant) and wild-type sequences (alleles). The method principles can however be applied to many different polymerase-based systems.

The example describes methods for detection of a single nucleotide mutation in a sample which may contain both wild-type and mutant DNA.

For pilot assays, the high-Tm primers (primer-H) were designed with a length of ~60bp and tested to operate relatively efficiently at annealing temperatures at ~72° C. or higher. The probes were designed to overlap the variant base with a length of ~13-16 bp, with a balance between positioning the variant base centrally while attempting to maximize the Tm. The low-Tm primers (primer-L) are designed to be as short as possible with the lowest Tm possible (typically <48° C.) while still achieving adequate sequence specificity and thus sufficient quality fluorescent signal regardless of the fluorophore. For fluorescently-labeled quenched probes, typically FAM was used for the mutant allele and HEX for wild-type; but any fluorophores can be used. The lengths and Tm's of the probes can be similar to that of the primer-L or some degrees higher. The number of AIPR cycles used can vary, but may typically be 64, and the number of symmetric PCR cycles can vary, but may typically be 27. Since there are many thermal cycles and polymerase loses activity based on the amount of total time at high temperatures, in this example each denature step was chosen to run for 10 seconds (see Table 1 for typical thermal cycling program).

An example of a useful assay design is shown in FIG. 2. FIG. 2 shows primer-H and Primer-L, as well as mutant detection Probe (MUT Probe) and wild-type detection probe (WT Probe) for detection of two mutations in the oncogene PIK3CA, namely H1047R and E542K.

Typical results for IBSAFE compared to a prior art assay is shown in FIG. 3. More specifically, FIG. 3 shows the result of an IBSAFE assay performed as a droplet digital PCR using thermal cycling conditions outlined in Table 1, and the primers and probes shown in FIG. 2, compared to the commercial assays from Bio-Rad Laboratories (PrimePCR™ Mutation Assay PIK3CA p.H1047R, Human, catalog #100-31246, and PrimePCR™ Mutation Assay PIK3CA WT for p.H1047R, Human, catalog #100-31249) run according to the manufacturer's standard protocol (hereinafter referred to as "Commercial assay").

For both commercial and IBSAFE assays, the digital droplet PCR was carried out using instrumentation from Bio-Rad Laboratories including the QX100 Droplet Generator (catalog #186-3002) and QX100 Droplet Reader (catalog #186-3001) and QuantaSoft software (catalog #186-3003). For the commercial assays from Bio-Rad Laboratories, the manufacturer's protocol was followed. IBSAFE assays were performed according to our methods herein.

FIG. 6 shows the measured mutant allele frequency versus the expected mutant allele frequency. The experiments were performed essentially as described herein above in relation to FIG. 3 except that the methods were performed using a template comprising a mixture of wild type and mutant DNA in different ratios as indicated in the figure. Whereas no false-positive mutant sequences are detected in the negative controls using the IBSAFE method, the negative control for the commercial assay showed the same amount of mutant (false-positive) as the sample with an expected mutant allele frequency of 0.01%. Thus, when using the IBSAFE method the expected mutant allele frequency is obtained at all tested concentration of mutant template, whereas the commercial assay results in the same frequency of measured mutant alleles for samples comprising no mutant DNA, 0.001% and 0.01% mutant DNA. Thus, the IBSAFE method detects the expected % of mutant alleles even in a sample comprising only 0.001% mutant DNA (see FIG. 6 lower panel).

TABLE 1

Typical IBSAFE Thermal Cycling Conditions

| Step | Cycles | Temperature | Time |
| --- | --- | --- | --- |
| Enzyme Activation | 1 | 95° C. | 10 m |
| Denaturation | 64 | 94° C. | 10 s |
| Annealing/Extension |  | High Temp | 45 s |
| Denaturation | 27 | 94° C. | 10 s |
| Annealing |  | Low Temp | 30 s |
| Extension |  | 72° C. | 30 s |
| Enzyme Deactivation | 1 | 98° C. | 10 m |
| Hold | 1 | 4° C. | Infinite |

FIG. 4 shows two different primer-H, a Primer-L, as well as mutant detection Probe (MUT Probe) and wild-type detection probe (WT Probe) for detection of a mutation in the oncogene PIK3CA, namely H1047R.

The result of using the primers and probes shown in FIG. 4 in different reaction methods is shown in FIG. 5. More specifically, in partitioned reactions including beta 1 or beta 2 Primer-H together with Primer-L and mutation-specific and wildtype specific probes as shown in FIG. 4 were run with mutation-positive DNA template (not shown; all assays detected the mutation) and wildtype template without AIPR (A), with AIPR at a lower (67° C.) temperature (B), and with AIPR at a higher (74°) temperature (C). Significant reduction of false-positive signals is achieved in C.

The digital droplet PCR and IBSAFE were carried out as described herein above using the thermocycling cycling conditions outlined in FIG. 5.

Figure 5A:
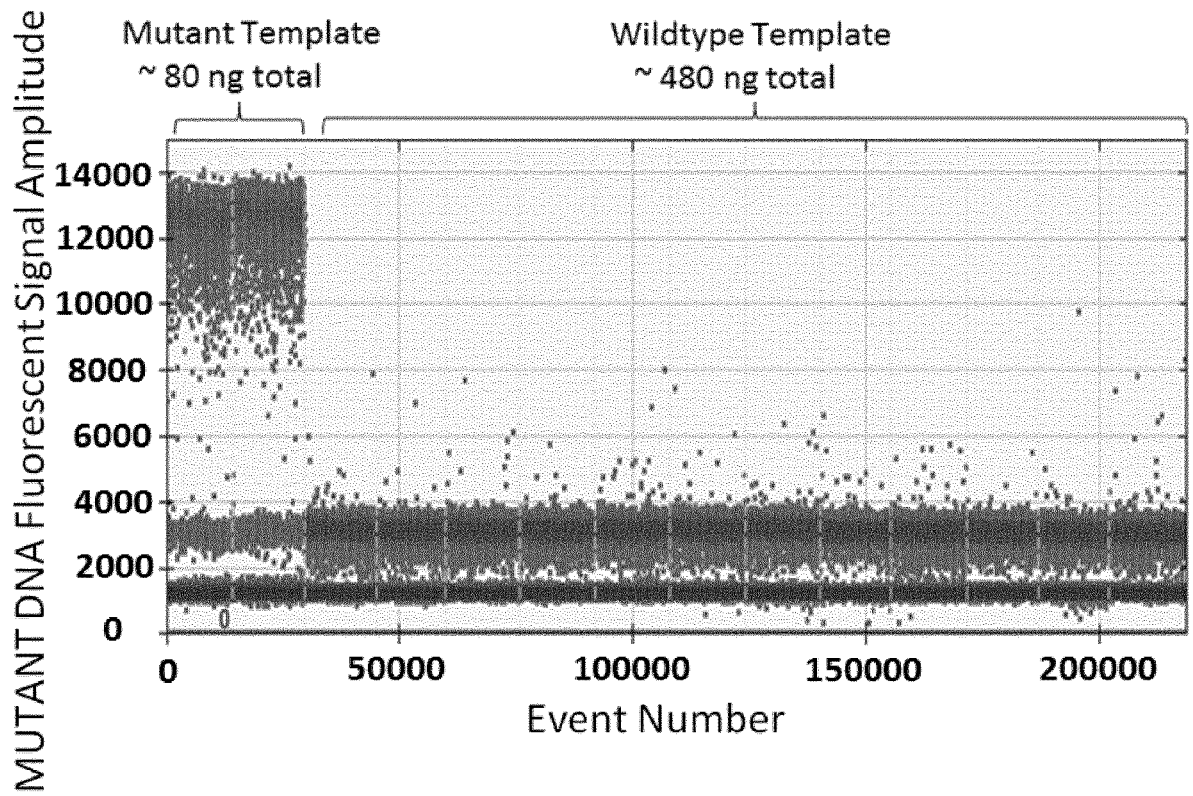
FIG. 5 shows Plots of Mutant (Specific) Signal Demonstrating AIPR Effect on False-Positive Signal-The experimental assay design shown in FIG. 4 was used including beta 1 or beta 2 Primer-H together with Primer-L and mutation-specific and wildtype specific probes (see FIG. 4) were run with mutation-positive DNA template (not shown; all assays detected the mutation) and wildtype template without AIPR (A), with AIPR at a lower (67° C.) temperature (B), and with AIPR at a higher (74°) temperature (C). Panels D, E and F show mutant (Specific) Signal And No False-Positive Signals Using Different AIPR Annealing Temperatures and Symmetric Annealing Temperatures; (D) IBSAFE assay for PIK3CA E542K mutation. In this example AIPR is run with a 75° C. annealing temperature and the symmetric stage with a 46° C. annealing temperature; (E) IBSAFE assay for mutation E545K in PIK3CA. In this example AIPR is run with a 75° C. annealing temperature and the symmetric stage using a 46° C. annealing temperature; (F) IBSAFE assay for NRAS Q61R mutation with AIPR using a 73° C. annealing temperature and the symmetric stage using a 48° C. annealing temperature.
Figure 5B:
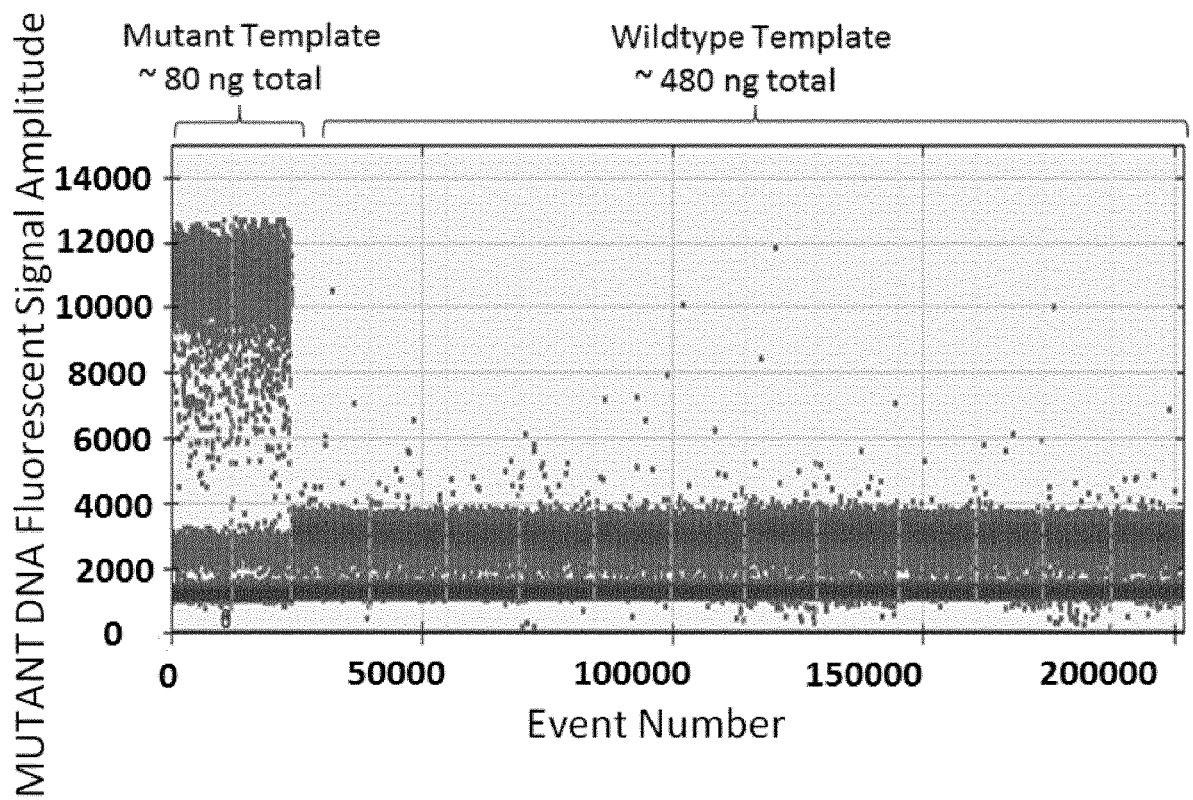
Figure 5C:
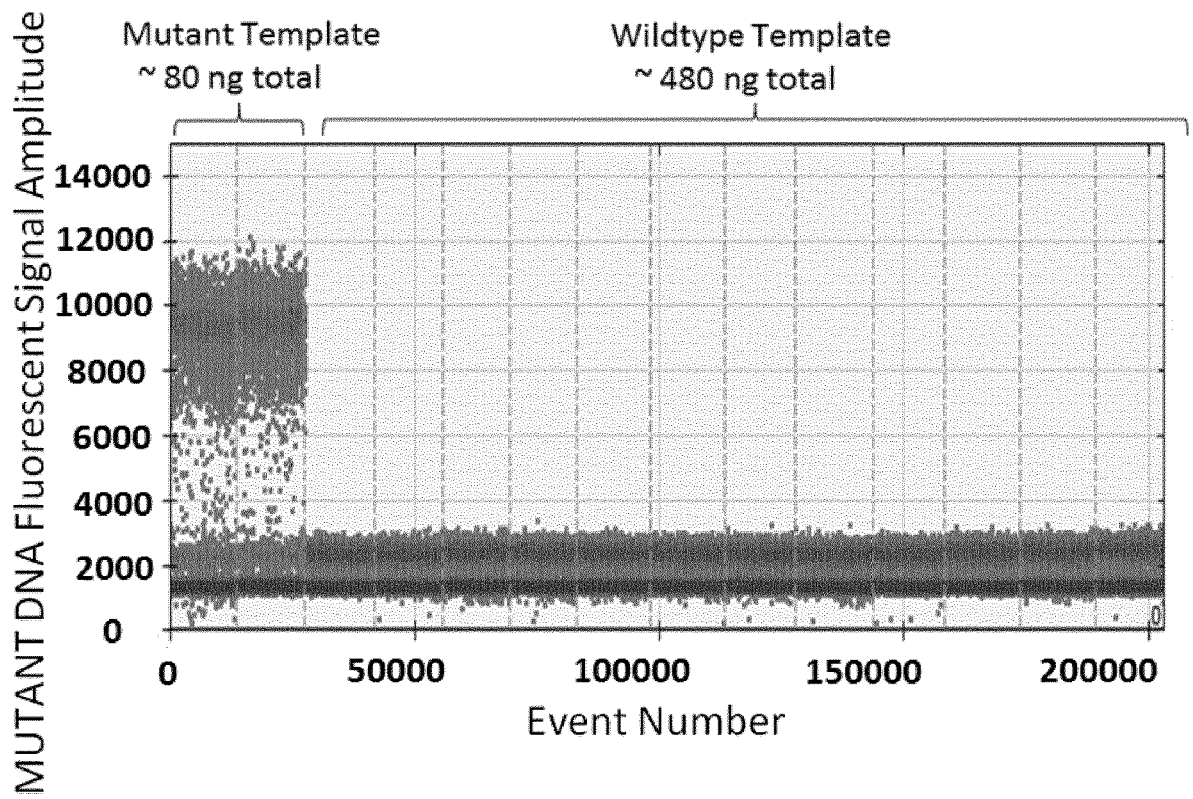
Figure 5D:
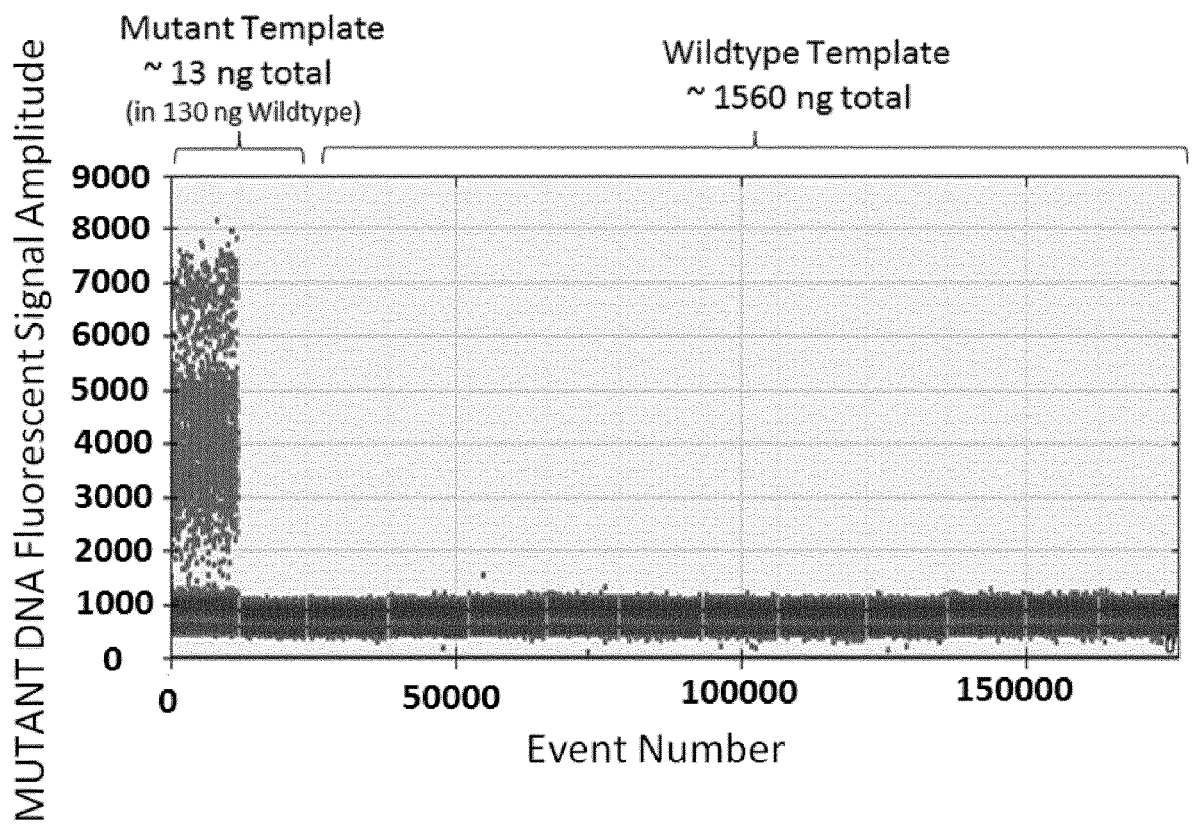

Similar IBSAFE reactions were performed using a range of different primers. FIG. 5D shows a mutant specific signal and no false-positive signals in an assay for detection of the PIK3CA E542K mutation. The following primers and probes were used:

| Gene | AA Mutation | CDS Mutation | Type | Sequence (5' to 3') |
| --- | --- | --- | --- | --- |
| PIK3CA | E542K | c.1624G>A | Primer-H | T+AA+TA+AA+GA+AA AAGAAA+CAGAGAA+T C+TC+CATTTTAGCAC TTACCTGTGAC* |
| PIK3CA | E542K | c.1624G>A | Primer-L | ATTTCTACACGAGATC |
| PIK3CA | E542K | c.1624G>A | Probe-WT | CTCTCTGAAATCACTG AG |
| PIK3CA | E542K | c.1624G>A | Probe-MUT | CTCTCTAAAATCACTG AG |

*LNA Bases indicated by "+" symbol before nucleotide

Figure 5E:
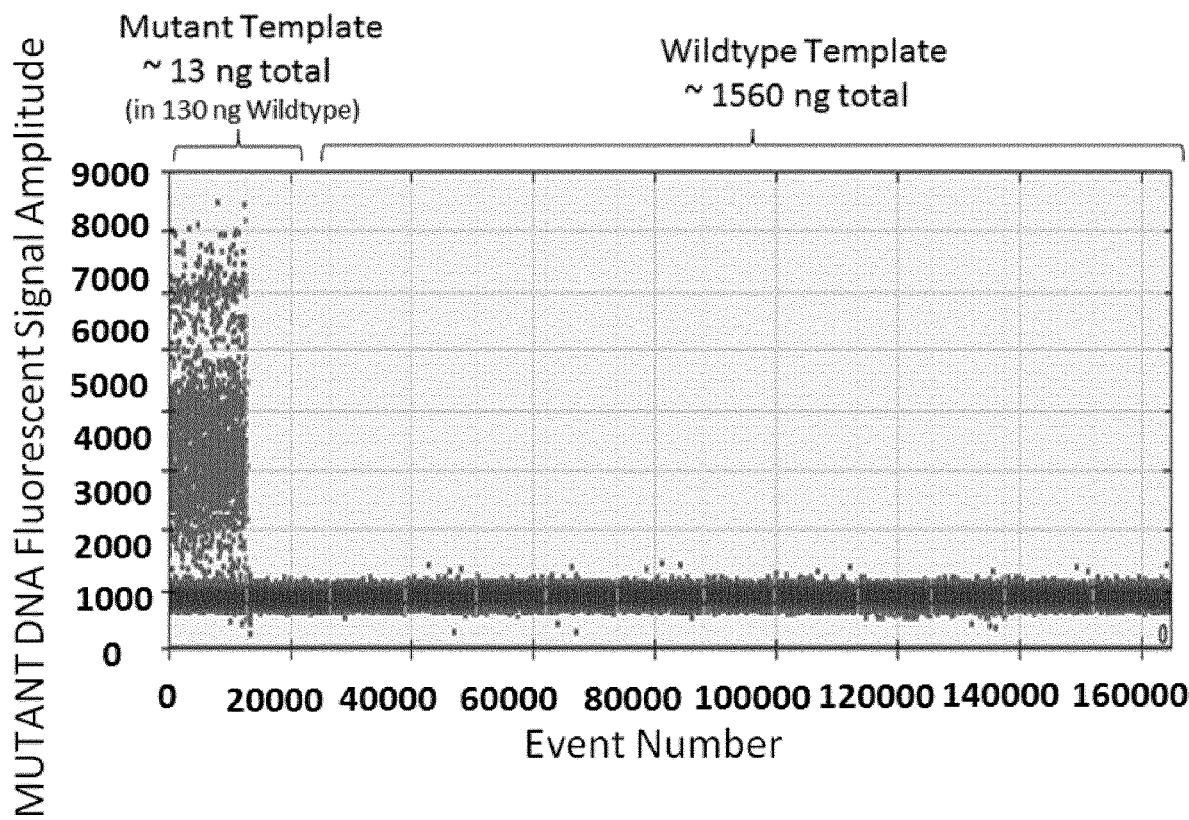

FIG. 5E shows a mutant specific signal and no false-positive signals in an assay for detection of the PIK3CA E545K mutation. The following primers and probes were used:

| Gene | AA Mutation | CDS Mutation | Type | Sequence (5' to 3') |
| --- | --- | --- | --- | --- |
| PIK3CA | E545K | c.1633G>A | Primer-H | T+AA+TA+AA+GA+AAA AGAAA+CAGAGAA+TC+ TC+CATTTTAGCACTTA CCTGTGAC* |
| PIK3CA | E545K | c.1633G>A | Primer-L | ATTTCTACACGAGATC |
| PIK3CA | E545K | c.1633G>A | Probe-WT | TCACTGAGCAGGAG |
| PIK3CA | E545K | c.1633G>A | Probe-MUT | TCACTAAGCAGGAG |

*LNA Bases indicated by "+" symbol before nucleotide

The primer-H used for FIGS. 5D and 5E comprised several LNA bases, which resulted in a high melting temperature providing a high Tm difference between the primer-H and primer-L, such that the AIPR stage was pure asymmetric (one direction) copying of the single-strand template. As is shown no false positives were detected.

Figure 5F:
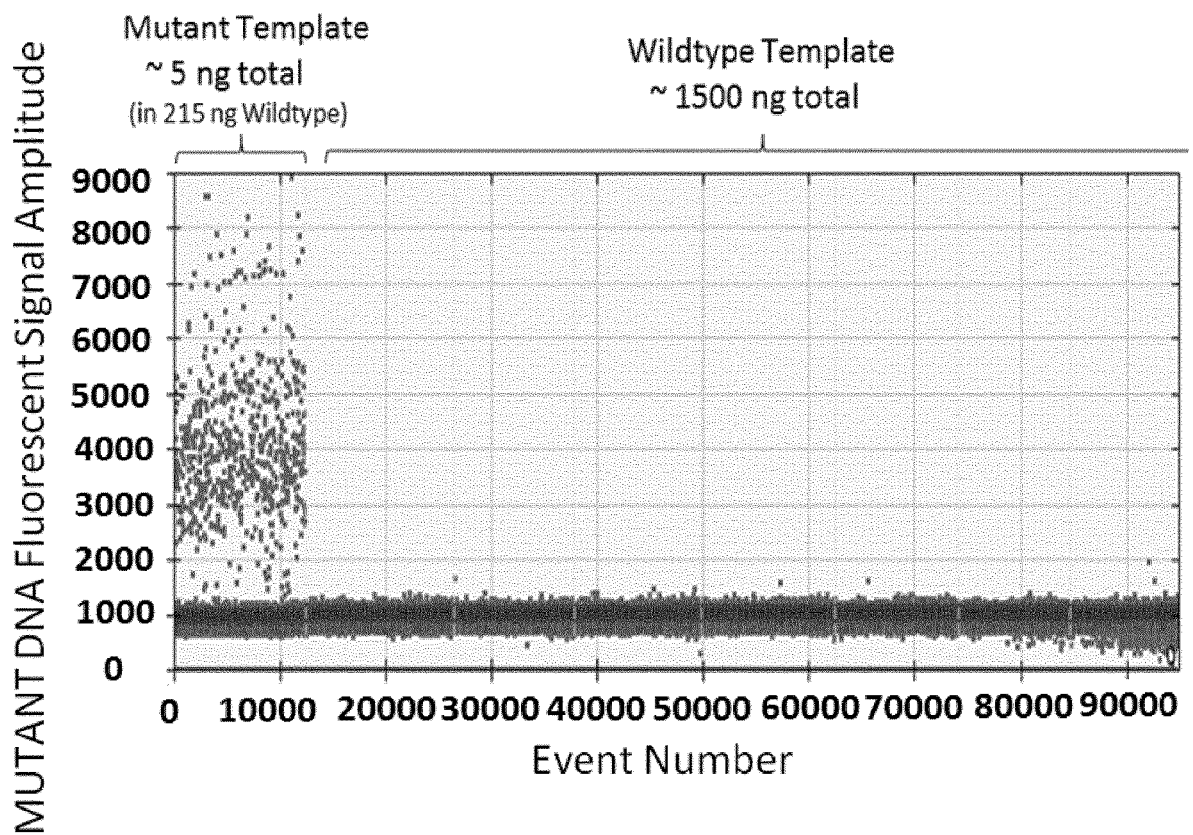

FIG. 5F shows a mutant specific signal and no false-positive signals in an assay for detection of the NRAS Q61R mutation. The following primers and probes were used:

| Gene | AA Mutation | CDS Mutation | Type | Sequence (5' to 3') |
| --- | --- | --- | --- | --- |
| NRAS | Q61R | c.182A>G | Primer-H | CCAGGATTCTTACAGAAA ACAAGTGGTTATAGATGG TGAAACCTGTTTGTTGGA CATACTGG |
| NRAS | Q61R | c.182A>G | Primer-L | GTATTGGTCTCTCATG |
| NRAS | Q61R | c.182A>G | Probe-WT | CTTCTTGTCCAGCTG |
| NRAS | Q61R | c.182A>G | Probe-MUT | CTTCTCGTCCAGCTG |

Theoretical calculations assuming 100% efficiency for the numbers of mutant allele copies per cycle of IBSAFE AIPR and symmetric PCR versus standard PCR are shown in Table 2. As seen, at a typical point for signal detection using the IBSAFE method after cycle 27, the worst-case scenario of the introduction of a false-positive variant in cycle 1 leads to the generation of false nucleic acids at an abundance of approximately 2% compared to the true-positive reaction. Conversely, in a standard PCR assay, the false-positive nucleic acids can be present at approximately 25% of the abundance of the true-positives at essentially any cycle (typically detection is performed at 40 cycles), contributing to a significant false-positive signal.

TABLE 2

Theoretical Calculations for Mutant Allele Copies.

| | | PARTITIONED REACTIONS | | | |
|---|---|---|---|---|---|
| | CYCLE | TOTAL MUT COPIES (FROM 1 DIPLOID MUTANT) AIPR/ SYMMETRIC PCR | TOTAL MUT COPIES (FROM 1ST CYCLE WT -> MUT POLYMERASE ERROR) AIPR/ SYMMETRIC PCR | TOTAL MUT COPIES (FROM 1 DIPLOID MUTANT) STANDARD PCR | TOTAL MUT COPIES (FROM 1ST CYCLE WT -> MUT POLYMERASE ERROR) STANDARD PCR |
| STARTING MUTANT COPIES | 0 | 2 | — | 2 | — |
| | 1 | 3 | 1 (POLYMERASE ERROR) | na | na |
| | 2 | 4 | 1 | na | na |
| | 6 | 8 | 1 | na | na |
| AIPR STAGE | 14 | 16 | 1 | na | na |
| | 30 | 32 | 1 | na | na |
| | 62 | 64 | 1 | na | na |
| | 64 | 66 | 1 | na | na |
| | 1 | 132 | 2 | 4 | 1 (POLYMERASE ERROR) |
| | 2 | 264 | 4 | 8 | 2 |
| | 3 | 528 | 8 | 16 | 4 |
| | 4 | 1,056 | 16 | 32 | 8 |
| | 5 | 2,112 | 32 | 64 | 16 |
| | 6 | 4,224 | 64 | 128 | 32 |
| | 7 | 8,448 | 128 | 256 | 64 |
| | 8 | 16,896 | 256 | 512 | 128 |
| | 9 | 33,792 | 512 | 1,024 | 256 |
| | 10 | 67,584 | 1,024 | 2,048 | 512 |
| | 11 | 135,168 | 2,048 | 4,096 | 1,024 |
| SYMMETRIC PCR | 12 | 270,336 | 4,096 | 8,192 | 2,048 |
| OR | 13 | 540,672 | 8,192 | 16,384 | 4,096 |
| STANDARD PCR | 14 | 1,081,344 | 16,384 | 32,768 | 8,192 |
| | 15 | 2,162,688 | 32,768 | 65,536 | 16,384 |
| | 16 | 4,325,376 | 65,536 | 131,072 | 32,768 |
| | 17 | 8,650,752 | 131,072 | 262,144 | 65,536 |
| | 18 | 17,301,504 | 262,144 | 524,288 | 131,072 |
| | 19 | 34,603,008 | 524,288 | 1,048,576 | 262,144 |
| | 20 | 69,206,016 | 1,048,576 | 2,097,152 | 524,288 |
| | 21 | 138,412,032 | 2,097,152 | 4,194,304 | 1,048,576 |
| | 22 | 276,824,064 | 4,194,304 | 8,388,608 | 2,097,152 |
| | 23 | 553,648,128 | 8,388,608 | 16,777,216 | 4,194,304 |
| | 24 | 1,107,296,256 | 16,777,216 | 33,554,432 | 8,388,608 |
| | 25 | 2,214,592,512 | 33,554,432 | 67,108,864 | 16,777,216 |
| | 26 | 4,429,185,024 | 67,108,864 | 134,217,728 | 33,554,432 |
| TYPICAL POINT FOR SIGNAL DETECTION | 27 | 8,858,370,048 | 134,217,728 | 268,435,456 | 67,108,864 |
| | 28 | 17,716,740,096 | 268,435,456 | 536,870,912 | 134,217,728 |
| | 29 | 35,433,480,192 | 536,870,912 | 1,073,741,824 | 268,435,456 |
| | 30 | 70,866,960,384 | 1,073,741,824 | 2,147,483,648 | 536,870,912 |
| | 31 | 141,733,920,768 | 2,147,483,648 | 4,294,967,296 | 1,073,741,824 |
| | 32 | 283,467,841,536 | 4,294,967,296 | 8,589,934,592 | 2,147,483,648 |
| | 33 | 566,935,683,072 | 8,589,934,592 | 17,179,869,184 | 4,294,967,296 |
| | 34 | 1,133,871,366,144 | 17,179,869,184 | 34,359,738,368 | 8,589,934,592 |
| | 35 | 2,267,742,732,288 | 34,359,738,368 | 68,719,476,736 | 17,179,869,184 |
| | 36 | 4,535,485,464,576 | 68,719,476,736 | 137,438,953,472 | 34,359,738,368 |
| | 37 | 9,070,970,929,152 | 137,438,953,472 | 274,877,906,944 | 68,719,476,736 |
| | 38 | 18,141,941,858,304 | 274,877,906,944 | 549,755,813,888 | 137,438,953,472 |
| | 39 | 36,283,883,716,608 | 549,755,813,888 | 1,099,511,627,776 | 274,877,906,944 |
| | 40 | 72,567,767,433,216 | 1,099,511,627,776 | 2,199,023,255,552 | 549,755,813,888 |

The skilled person will be capable of designing useful primers and probes for detection of other mutations according to the IBSAFE method described herein. Table 3 summarises non-limiting examples of useful primer-H, primer-L and detection probes for detection of a number of different mutations.

Each of the mutations outlined in Table 3 can be detected by performing IBSAFE as described herein, wherein the IBSAFE reaction contains the primer-H, the primer-L the Probe-WT and the Probe-MUT indicated for the particular mutation in Table 3. The IBSAFE method may be performed essentially as described in this example e.g. using the thermal cycling conditions outlined in Table 1. The high and low annealing temperature may be set according to the Tm indicated in table 3.

TABLE 3

| Gene | AA Mutation | CDS Mutation | Type | Direction | Tm (° C.) | Length (bp) | Sequence (5' to 3') |
|---|---|---|---|---|---|---|---|
| PIK3CA | H1047R | c.3140A>G | Primer-H | F | 82 | 60 | AAGACCCTAGCCTTAGATAAAA CTGAGCAAGAGGCTTTGGAGTA TTTCATGAAACAAATG |
| PIK3CA | H1047R | c.3140A>G | Primer-L | R | 51.4 | 16 | CATTTTTGTTGTCCAG |
| PIK3CA | H1047R | c.3140A>G | Probe-WT | R | 54 | 14 | CCACCATGATGTGC |
| PIK3CA | H1047R | c.3140A>G | Probe-MUT | R | 57.7 | 14 | CCACCATGACGTGC |
| PIK3CA | E542K | c.1624G>A | Primer-H | R | 78.7 | 60 | CTGTAATAAAGAAAAAGAAACA GAGAATCTCCATTTTAGCACTTA CCTGTGACTCCATAG |
| PIK3CA | E542K | c.1624G>A | Primer-L | F | 31.8 | 12 | CTACACGAGATC |
| PIK3CA | E542K | c.1624G>A | Probe-WT | F | 46.9 | 16 | CTCTGAAATCACTGAG |
| PIK3CA | E542K | c.1624G>A | Probe-MUT | F | 43.9 | 16 | TCTCTAAAATCACTGA |
| PIK3CA | E545K | c.1633G>A | Primer-H | R | 78.7 | 60 | CTGTAATAAAGAAAAAGAAACA GAGAATCTCCATTTTAGCACTTA CCTGTGACTCCATAG |
| PIK3CA | E545K | c.1633G>A | Primer-L | F | 31.8 | 12 | CTACACGAGATC |
| PIK3CA | E545K | c.1633G>A | Probe-WT | F | 49.2 | 14 | TCACTGAGCAGGAG |
| PIK3CA | E545K | c.1633G>A | Probe-MUT | F | 44.9 | 14 | TCACTAAGCAGGAG |
| BRAF | V600E | c.1799T>A | Primer-H | R | 89.6 | 60 | TCTTACCATCCACAAAATGGATC CAGACAACTGTTCAAACTGATG GGACCCACTCCATCG |
| BRAF | V600E | c.1799T>A | Primer-L | F | 45.6 | 15 | GATTTTGGTCTAGCT |
| BRAF | V600E | c.1799T>A | Probe-WT | F | 44.2 | 14 | ACAGTGAAATCTCG |
| BRAF | V600E | c.1799T>A | Probe-MUT | F | 43.3 | 14 | ACAGAGAAATCTCG |
| EGFR | L858R | c.2573T>G | Primer-H | R | 89.5 | 60 | AAGCCACCTCCTTACTTTGCCTC CTTCTGCATGGTATTCTTTCTC TTCCGCACCCAGCAG |
| EGFR | L858R | c.2573T>G | Primer-L | F | 42 | 14 | TGTCAAGATCACAG |
| EGFR | L858R | c.2573T>G | Probe-WT | F | 60.7 | 13 | TTTTGGGCTGGCG |
| EGFR | L858R | c.2573T>G | Probe-MUT | F | 60.4 | 12 | TTTTGGGCGGGC |
| EGFR | T790M | c.2369C>T | Primer-H | R | 93 | 60 | TGGGAGCCAATATTGTCTTTGTG TTCCCGGACATAGTCCAGGAGG CAGCCGAAGGGCATG |
| EGFR | T790M | c.2369C>T | Primer-L | F | 43.5 | 10 | ACCGTGCAGC |
| EGFR | T790M | c.2369C>T | Probe-WT | F | 51.2 | 13 | TCATCACGCAGCT |
| EGFR | T790M | c.2369C>T | Probe-MUT | F | 47 | 13 | TCATCATGCAGCT |
| KRAS | G13D | c.38G>A | Primer-H | R | 84.4 | 60 | ATTGTTGGATCATATTCGTCCAC AAAATGATTCTGAATTAGCTGTA TCGTCAAGGCACTC |
| KRAS | G13D | c.38G>A | Primer-L | F | 37.9 | 13 | CTTGTGGTAGTTG |
| KRAS | G13D | c.38G>A | Probe-WT | F | 53.4 | 13 | CTGGTGGCGTAGG |
| KRAS | G13D | c.38G>A | Probe-MUT | F | 45.6 | 13 | CTGGTGACGTAGG |
| KRAS | G12C | c.34G>T | Primer-H | R | 84.4 | 60 | ATTGTTGGATCATATTCGTCCAC AAAATGATTCTGAATTAGCTGTA TCGTCAAGGCACTC |
| KRAS | G12C | c.34G>T | Primer-L | F | 37.9 | 13 | CTTGTGGTAGTTG |
| KRAS | G12C | c.34G>T | Probe-MUT | F | 50.3 | 13 | AGCTTGTGGCGTA |

TABLE 3-continued

| Gene | AA Mutation | CDS Mutation | Type | Direction | Tm (° C.) | Length (bp) | Sequence (5' to 3') |
|---|---|---|---|---|---|---|---|
| KRAS | G12C | c.34G>T | Probe-WT | F | 53.6 | 13 | AGCTGGTGGCGTA |
| KRAS | G12R | c.34G>C | Primer-H | R | 84.4 | 60 | ATTGTTGGATCATATTCGTCCAC AAAATGATTCTGAATTAGCTGTA TCGTCAAGGCACTC |
| KRAS | G12R | c.34G>C | Primer-L | F | 37.9 | 13 | CTTGTGGTAGTTG |
| KRAS | G12R | c.34G>C | Probe-MUT | F | 53.8 | 13 | AGCTCGTGGCGTA |
| KRAS | G12R | c.34G>C | Probe-WT | F | 53.6 | 13 | AGCTGGTGGCGTA |
| KRAS | G12S | c.34G>A | Primer-H | R | 84.4 | 60 | ATTGTTGGATCATATTCGTCCAC AAAATGATTCTGAATTAGCTGTA TCGTCAAGGCACTC |
| KRAS | G12S | c.34G>A | Primer-L | F | 37.9 | 13 | CTTGTGGTAGTTG |
| KRAS | G12S | c.34G>A | Probe-MUT | F | 45.7 | 13 | AGCTAGTGGCGTA |
| KRAS | G12S | c.34G>A | Probe-WT | F | 53.6 | 13 | AGCTGGTGGCGTA |
| KRAS | G12V | c.35G>T | Primer-H | R | 84.4 | 60 | ATTGTTGGATCATATTCGTCCAC AAAATGATTCTGAATTAGCTGTA TCGTCAAGGCACTC |
| KRAS | G12V | c.35G>T | Primer-L | F | 37.9 | 13 | CTTGTGGTAGTTG |
| KRAS | G12V | c.35G>T | Probe-MUT | F | 50.3 | 13 | AGCTGTTGGCGTA |
| KRAS | G12V | c.35G>T | Probe-WT | F | 53.6 | 13 | AGCTGGTGGCGTA |
| KRAS | G12A | c.35G>C | Primer-H | R | 84.4 | 60 | ATTGTTGGATCATATTCGTCCAC AAAATGATTCTGAATTAGCTGTA TCGTCAAGGCACTC |
| KRAS | G12A | c.35G>C | Primer-L | F | 37.9 | 13 | CTTGTGGTAGTTG |
| KRAS | G12A | c.35G>C | Probe-MUT | F | 54.1 | 13 | AGCTGCTGGCGTA |
| KRAS | G12A | c.35G>C | Probe-WT | F | 53.6 | 13 | AGCTGGTGGCGTA |
| KRAS | G12D | c.35G>A | Primer-H | R | 84.4 | 60 | ATTGTTGGATCATATTCGTCCAC AAAATGATTCTGAATTAGCTGTA TCGTCAAGGCACTC |
| KRAS | G12D | c.35G>A | Primer-L | F | 37.9 | 13 | CTTGTGGTAGTTG |
| KRAS | G12D | c.35G>A | Probe-MUT | F | 50.1 | 13 | AGCTGATGGCGTA |
| KRAS | G12D | c.35G>A | Probe-WT | F | 53.6 | 13 | AGCTGGTGGCGTA |

Example 2

Figure 7B:
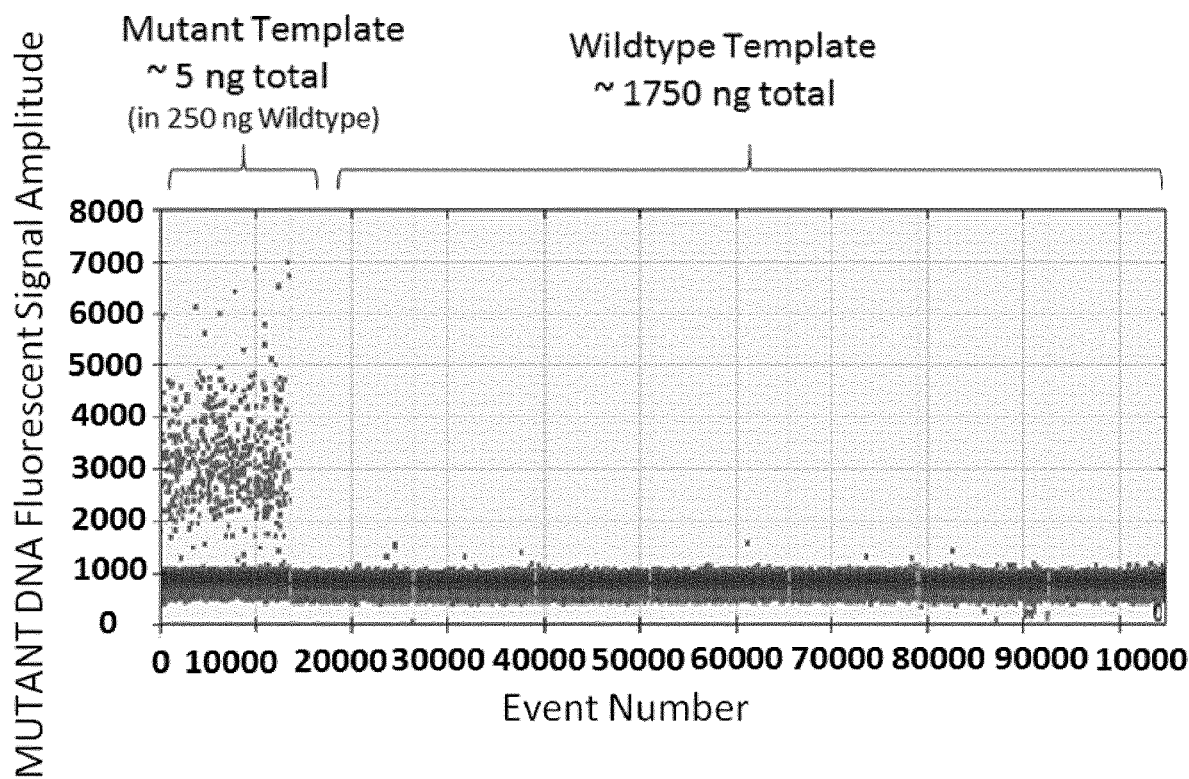
FIG. 7 shows the assay design (A) and the results (B) of a method according to the invention using a mismatch modified primer-L targeting the KRAS G13D mutation.

IBSAFE methods were performed essentially as described in Example 1 except that an extra step of low temperature PCR was also used. In this example of an IBSAFE method a mismatched sequence is used for Primer-L. This results in a further gap in the effective melting temperature difference between Primer-H and Primer-L during the AIPR stage The assay design used in this example is shown in FIG. 7A and includes a primer-H, a wild-type detection probe (WT probe) and a variant detection probe (MUT probe). Furthermore, the assay includes use of a Primer-L comprising 4 mismatched nucleotides. The method used in this example comprises a step of AIPR, a step of low temperature PCR followed by an exponential PCR. The exact thermocycler programme used is shown in FIG. 7B.

This example is an IBSAFE assay for the KRAS G13D mutation. A 4-base mismatching sequence is included at the 5' end of the Primer-L and the primer sequence complementary to the target is short. Therefore, Primer-L has a very low melting temperature and will not anneal at the high annealing temperature during the AIPR stage (73° C. in this example). In the symmetric stage, the annealing temperature used is very low (30° C. in this example). After some cycles (in this example, 5 cycles), the complementary sequence to the full length of Primer-L is incorporated into the synthesized product and the symmetric PCR can be continued at a higher annealing temperature (53° C. in this example), where now the full length of Primer-L is a perfect match.

The result is shown in FIG. 7B showing a mutant specific signal and no false positives.

The invention claimed is:

1. A method for detection of the presence of a target nucleic acid sequence or detection of the presence of a variant sequence in a target nucleic acid sequence in a sample comprising the steps of
   a) providing a sample comprising template nucleic acids,
   b) providing a set of primers comprising at least a pair of primers specifically capable of amplification of the target nucleic acid sequence, wherein the set of primers at least comprises a primer-H and a primer-L, wherein the melting temperature of primer-H is at least 16° C. higher than the melting temperature of primer-L, and wherein primer-L contains a sequence complementary to a fragment of the elongation product of primer-H,
   c) providing a nucleic acid polymerase having polymerase activity at an elongation temperature,
   d) preparing partitioned PCR reactions each comprising a part of the sample, the set of primers, the nucleic acid polymerase, PCR reagents and optionally detection reagents,
   e) performing an asymmetric incremental polymerase reaction (AIPR) comprising the steps of:
      i) incubating the partitioned PCR reactions at a denaturation temperature, thereby denaturing DNA to single-stranded molecules,
      ii) incubating the partitioned PCR reactions at a high annealing temperature allowing annealing of primer-H, but not of primer-L,
      iii) optionally incubating the partitioned PCR reactions at the elongation temperature,
      iv) optionally repeating steps i to iii,
   f) performing a polymerase chain reaction (PCR) comprising the steps of:
      1) incubating the partitioned PCR reactions from step e) at a denaturation temperature, thereby denaturing DNA to single-stranded molecules,
      2) incubating the PCR at a low annealing temperature allowing annealing of both primer-H and primer-L,
      3) incubating the PCR at the elongation temperature thereby allowing extension of all annealed primers,
      4) optionally repeating steps 1 to 3,
   g) detecting whether the PCR product comprises the target nucleic acid sequence or the variant sequence in the target nucleic acid sequence.

2. The method according to claim 1, wherein the variant sequence is a single nucleotide mutation.

3. The method according to claim 1, wherein the AIPR of step e) comprises the steps of:
   i) incubating the partitioned PCR reactions at a denaturation temperature, thereby denaturing DNA to single-stranded molecules;
   ii) incubating the partitioned PCR reactions at a high annealing temperature allowing annealing of primer-H, but not of primer-L, wherein the high annealing temperature also is the elongation temperature, thereby allowing for extension of the annealed primer-H;
   iii) repeating steps i to ii.

4. The method according to claim 1, wherein primer-H is the only primer in the set of primers that has a melting temperature at least 16° C. higher than the melting temperature of primer-L.

5. The method according to claim 1, wherein the set of primers comprises more than one pair of primers capable of amplification of different target nucleic acid sequences.

6. The method according to claim 1, wherein primer-H has a melting temperature at least 16° C. higher than the melting temperature of any other primer within the set of primer, which together with Primer-H is capable of amplification of the target nucleic acid sequence.

7. The method according to claim 1, wherein the set of primers do not comprise any primers:
   a) which have a melting temperature which is in the range of +/−15° C. of the melting temperature of primer-H; and
   b) which together with primer-H can constitute a pair of primers specifically capable of amplification of the target nucleic acid sequence.

8. The method according to claim 1, wherein the high annealing temperature in step e) is at least 10° C. higher than the melting temperature of primer-L.

9. The method according to claim 1, wherein step e) results in elongation of primer-H, but in no detectable elongation of any other primer.

10. The method according to claim 1, wherein primer-L is a mismatch modified primer-L and the method comprises a step of low temperature PCR between steps e) and f), wherein the low temperature PCR comprises the steps of:
    1) incubating the partitioned PCR reactions at a denaturation temperature, thereby denaturing DNA to single-stranded molecules,
    2) incubating the PCR at a very low annealing temperature allowing annealing of both primer-H and of the non-mismatched part of primer-L,
    3) incubating the PCR at the elongation temperature thereby allowing extension of all annealed primers,
    4) optionally repeating steps 1) to 3), thereby obtaining a PCR product.

11. The method according to claim 10, wherein the very low annealing temperature is at least 5° C. lower than the low annealing temperature.

12. The method according to claim 10, wherein primer-L is an oligonucleotide consisting of:
    a) a 5' sequence of 1 to 10 nucleotides; and
    b) a consecutive sequence in the range of 7 to 15 nucleotides, which is identical to or complementary to a fragment of the target nucleic acid sequence.

13. The method according to claim 1, wherein the partitioned PCR reactions each contains a detection reagent, which is a variant detection probe, said variant detection probe being capable of hybridizing to the target nucleic acid sequence containing the variant sequence with significantly higher affinity than to the target nucleic acid sequence not containing the variant sequence and/or the partitioned PCR reactions each contains a detection reagent which is a wild-type detection probe, said wild-type detection probe being capable of hybridizing to the target nucleic acid sequence not containing the variant sequence.

* * * * *

SEQUENCE LISTING

<160> NUMBER OF SEQ ID NOS: 72

<210> SEQ ID NO 1
<211> LENGTH: 60
<212> TYPE: DNA
<213> ORGANISM: Artificial Sequence
<220> FEATURE:
<223> OTHER INFORMATION: Primer-H

<400> SEQUENCE: 1
aagaccctag ccttagataa aactgagcaa gaggctttgg agtatttcat gaaacaaatg     60

<210> SEQ ID NO 2
<211> LENGTH: 16
<212> TYPE: DNA
<213> ORGANISM: Artificial Sequence
<220> FEATURE:
<223> OTHER INFORMATION: Primer-L

<400> SEQUENCE: 2 cattttttgtt gtccag                                                   16

<210> SEQ ID NO 3
<211> LENGTH: 14
<212> TYPE: DNA
<213> ORGANISM: Artificial Sequence
<220> FEATURE:
<223> OTHER INFORMATION: Probe WT

<400> SEQUENCE: 3
ccaccatgat gtgc                                                      14

<210> SEQ ID NO 4
<211> LENGTH: 14
<212> TYPE: DNA
<213> ORGANISM: Artificial Sequence
<220> FEATURE:
<223> OTHER INFORMATION: Probe MUT

<400> SEQUENCE: 4
ccaccatgac gtgc                                                      14

<210> SEQ ID NO 5
<211> LENGTH: 60
<212> TYPE: DNA
<213> ORGANISM: Artificial Sequence
<220> FEATURE:
<223> OTHER INFORMATION: Primer-H

<400> SEQUENCE: 5
ctgtaataaa gaaaagaaa cagagaatct ccattttagc acttacctgt gactccatag      60

<210> SEQ ID NO 6
<211> LENGTH: 12
<212> TYPE: DNA
<213> ORGANISM: Artificial Sequence
<220> FEATURE:
<223> OTHER INFORMATION: Primer-L

<400> SEQUENCE: 6
ctacacgaga tc                                                        12

<210> SEQ ID NO 7
<211> LENGTH: 16
<212> TYPE: DNA
<213> ORGANISM: Artificial Sequence
<220> FEATURE:
<223> OTHER INFORMATION: Probe-WT

<400> SEQUENCE: 7
ctctgaaatc actgag                                                    16

<210> SEQ ID NO 8
<211> LENGTH: 16
<212> TYPE: DNA
<213> ORGANISM: Artificial Sequence
<220> FEATURE:
<223> OTHER INFORMATION: Probe-MUT

<400> SEQUENCE: 8
tctctaaaat cactga                                                    16

<210> SEQ ID NO 9
<211> LENGTH: 60
<212> TYPE: DNA
<213> ORGANISM: Artificial Sequence
<220> FEATURE:
<223> OTHER INFORMATION: Primer-H

<400> SEQUENCE: 9
ctgtaataaa gaaaagaaa cagagaatct ccattttagc acttacctgt gactccatag     60

<210> SEQ ID NO 10
<211> LENGTH: 12
<212> TYPE: DNA
<213> ORGANISM: Artificial Sequence
<220> FEATURE:
<223> OTHER INFORMATION: Primer-L

<400> SEQUENCE: 10
ctacacgaga tc                                                        12

<210> SEQ ID NO 11
<211> LENGTH: 14
<212> TYPE: DNA
<213> ORGANISM: Artificial Sequence
<220> FEATURE:
<223> OTHER INFORMATION: Probe-WT

<400> SEQUENCE: 11
tcactgagca ggag                                                      14

<210> SEQ ID NO 12
<211> LENGTH: 14
<212> TYPE: DNA
<213> ORGANISM: Artificial Sequence
<220> FEATURE:
<223> OTHER INFORMATION: Probe-MUT

<400> SEQUENCE: 12
tcactaagca ggag                                                      14

<210> SEQ ID NO 13
<211> LENGTH: 60
<212> TYPE: DNA
<213> ORGANISM: Artificial Sequence
<220> FEATURE:
<223> OTHER INFORMATION: Primer-H

<400> SEQUENCE: 13
tcttaccatc cacaaaatgg atccagacaa ctgttcaaac tgatgggacc cactccatcg    60

```
<210> SEQ ID NO 14
<211> LENGTH: 15
<212> TYPE: DNA
<213> ORGANISM: Artificial Sequence
<220> FEATURE:
<223> OTHER INFORMATION: Primer-L

<400> SEQUENCE: 14
gattttggtc tagct                                                      15

<210> SEQ ID NO 15
<211> LENGTH: 14
<212> TYPE: DNA
<213> ORGANISM: Artificial Sequence
<220> FEATURE:
<223> OTHER INFORMATION: Probe-WT

<400> SEQUENCE: 15
acagtgaaat ctcg                                                       14

<210> SEQ ID NO 16
<211> LENGTH: 14
<212> TYPE: DNA
<213> ORGANISM: Artificial Sequence
<220> FEATURE:
<223> OTHER INFORMATION: Probe-MUT

<400> SEQUENCE: 16
acagagaaat ctcg                                                       14

<210> SEQ ID NO 17
<211> LENGTH: 60
<212> TYPE: DNA
<213> ORGANISM: Artificial Sequence
<220> FEATURE:
<223> OTHER INFORMATION: Primer-H

<400> SEQUENCE: 17
aagccacctc cttactttgc ctccttctgc atggtattct ttctcttccg cacccagcag     60

<210> SEQ ID NO 18
<211> LENGTH: 14
<212> TYPE: DNA
<213> ORGANISM: Artificial Sequence
<220> FEATURE:
<223> OTHER INFORMATION: Primer-L

<400> SEQUENCE: 18
tgtcaagatc acag                                                       14

<210> SEQ ID NO 19
<211> LENGTH: 13
<212> TYPE: DNA
<213> ORGANISM: Artificial Sequence
<220> FEATURE:
<223> OTHER INFORMATION: Probe-WT

<400> SEQUENCE: 19
ttttgggctg gcg                                                        13

<210> SEQ ID NO 20
<211> LENGTH: 12
<212> TYPE: DNA
<213> ORGANISM: Artificial Sequence
<220> FEATURE:
<223> OTHER INFORMATION: Probe-MUT
```

<400> SEQUENCE: 20
ttttgggcgg gc                                                              12

<210> SEQ ID NO 21
<211> LENGTH: 60
<212> TYPE: DNA
<213> ORGANISM: Artificial Sequence
<220> FEATURE:
<223> OTHER INFORMATION: Primer-H

<400> SEQUENCE: 21
tgggagccaa tattgtcttt gtgttcccgg acatagtcca ggaggcagcc gaagggcatg          60

<210> SEQ ID NO 22
<211> LENGTH: 10
<212> TYPE: DNA
<213> ORGANISM: Artificial Sequence
<220> FEATURE:
<223> OTHER INFORMATION: Primer-L

<400> SEQUENCE: 22
accgtgcagc                                                                 10

<210> SEQ ID NO 23
<211> LENGTH: 13
<212> TYPE: DNA
<213> ORGANISM: Artificial Sequence
<220> FEATURE:
<223> OTHER INFORMATION: Probe-WT

<400> SEQUENCE: 23
tcatcacgca gct                                                             13

<210> SEQ ID NO 24
<211> LENGTH: 13
<212> TYPE: DNA
<213> ORGANISM: Artificial Sequence
<220> FEATURE:
<223> OTHER INFORMATION: Probe-MUT

<400> SEQUENCE: 24
tcatcatgca gct                                                             13

<210> SEQ ID NO 25
<211> LENGTH: 60
<212> TYPE: DNA
<213> ORGANISM: Artificial Sequence
<220> FEATURE:
<223> OTHER INFORMATION: Primer-H

<400> SEQUENCE: 25
attgttggat catattcgtc cacaaaatga ttctgaatta gctgtatcgt caaggcactc          60

<210> SEQ ID NO 26
<211> LENGTH: 13
<212> TYPE: DNA
<213> ORGANISM: Artificial Sequence
<220> FEATURE:
<223> OTHER INFORMATION: Primer-L

<400> SEQUENCE: 26
cttgtggtag ttg                                                             13

<210> SEQ ID NO 27

-continued

<210> SEQ ID NO 27
<211> LENGTH: 13
<212> TYPE: DNA
<213> ORGANISM: Artificial Sequence
<220> FEATURE:
<223> OTHER INFORMATION: Probe-WT

<400> SEQUENCE: 27
ctggtggcgt agg                                              13

<210> SEQ ID NO 28
<211> LENGTH: 13
<212> TYPE: DNA
<213> ORGANISM: Artificial Sequence
<220> FEATURE:
<223> OTHER INFORMATION: Probe-MUT

<400> SEQUENCE: 28
ctggtgacgt agg                                              13

<210> SEQ ID NO 29
<211> LENGTH: 60
<212> TYPE: DNA
<213> ORGANISM: Artificial Sequence
<220> FEATURE:
<223> OTHER INFORMATION: Primer-H

<400> SEQUENCE: 29
attgttggat catattcgtc cacaaaatga ttctgaatta gctgtatcgt caaggcactc    60

<210> SEQ ID NO 30
<211> LENGTH: 13
<212> TYPE: DNA
<213> ORGANISM: Artificial Sequence
<220> FEATURE:
<223> OTHER INFORMATION: Primer-L

<400> SEQUENCE: 30
cttgtggtag ttg                                              13

<210> SEQ ID NO 31
<211> LENGTH: 13
<212> TYPE: DNA
<213> ORGANISM: Artificial Sequence
<220> FEATURE:
<223> OTHER INFORMATION: Probe-MUT

<400> SEQUENCE: 31
agcttgtggc gta                                              13

<210> SEQ ID NO 32
<211> LENGTH: 13
<212> TYPE: DNA
<213> ORGANISM: Artificial Sequence
<220> FEATURE:
<223> OTHER INFORMATION: Probe-WT

<400> SEQUENCE: 32
agctggtggc gta                                              13

<210> SEQ ID NO 33
<211> LENGTH: 60
<212> TYPE: DNA
<213> ORGANISM: Artificial Sequence
<220> FEATURE:
<223> OTHER INFORMATION: Primer-H

<400> SEQUENCE: 33

```
attgttggat catattcgtc cacaaaatga ttctgaatta gctgtatcgt caaggcactc    60
```

<210> SEQ ID NO 34
<211> LENGTH: 13
<212> TYPE: DNA
<213> ORGANISM: Artificial Sequence
<220> FEATURE:
<223> OTHER INFORMATION: Primer-L

<400> SEQUENCE: 34

```
cttgtggtag ttg                                                       13
```

<210> SEQ ID NO 35
<211> LENGTH: 13
<212> TYPE: DNA
<213> ORGANISM: Artificial Sequence
<220> FEATURE:
<223> OTHER INFORMATION: Probe-MUT

<400> SEQUENCE: 35

```
agctcgtggc gta                                                       13
```

<210> SEQ ID NO 36
<211> LENGTH: 13
<212> TYPE: DNA
<213> ORGANISM: Artificial Sequence
<220> FEATURE:
<223> OTHER INFORMATION: Probe-WT

<400> SEQUENCE: 36

```
agctggtggc gta                                                       13
```

<210> SEQ ID NO 37
<211> LENGTH: 60
<212> TYPE: DNA
<213> ORGANISM: Artificial Sequence
<220> FEATURE:
<223> OTHER INFORMATION: Primer-H

<400> SEQUENCE: 37

```
attgttggat catattcgtc cacaaaatga ttctgaatta gctgtatcgt caaggcactc    60
```

<210> SEQ ID NO 38
<211> LENGTH: 13
<212> TYPE: DNA
<213> ORGANISM: Artificial Sequence
<220> FEATURE:
<223> OTHER INFORMATION: Primer-L

<400> SEQUENCE: 38

```
cttgtggtag ttg                                                       13
```

<210> SEQ ID NO 39
<211> LENGTH: 13
<212> TYPE: DNA
<213> ORGANISM: Artificial Sequence
<220> FEATURE:
<223> OTHER INFORMATION: Probe-MUT

<400> SEQUENCE: 39

```
agctagtggc gta                                                       13
```

<210> SEQ ID NO 40
<211> LENGTH: 13
<212> TYPE: DNA

```
<213> ORGANISM: Artificial Sequence
<220> FEATURE:
<223> OTHER INFORMATION: Probe-WT

<400> SEQUENCE: 40
agctggtggc gta                                                          13

<210> SEQ ID NO 41
<211> LENGTH: 60
<212> TYPE: DNA
<213> ORGANISM: Artificial Sequence
<220> FEATURE:
<223> OTHER INFORMATION: Primer-H

<400> SEQUENCE: 41
attgttggat catattcgtc cacaaaatga ttctgaatta gctgtatcgt caaggcactc        60

<210> SEQ ID NO 42
<211> LENGTH: 13
<212> TYPE: DNA
<213> ORGANISM: Artificial Sequence
<220> FEATURE:
<223> OTHER INFORMATION: Primer-L

<400> SEQUENCE: 42
cttgtggtag ttg                                                          13

<210> SEQ ID NO 43
<211> LENGTH: 13
<212> TYPE: DNA
<213> ORGANISM: Artificial Sequence
<220> FEATURE:
<223> OTHER INFORMATION: Probe-MUT

<400> SEQUENCE: 43
agctgttggc gta                                                          13

<210> SEQ ID NO 44
<211> LENGTH: 13
<212> TYPE: DNA
<213> ORGANISM: Artificial Sequence
<220> FEATURE:
<223> OTHER INFORMATION: Probe-WT

<400> SEQUENCE: 44
agctggtggc gta                                                          13

<210> SEQ ID NO 45
<211> LENGTH: 60
<212> TYPE: DNA
<213> ORGANISM: Artificial Sequence
<220> FEATURE:
<223> OTHER INFORMATION: Primer-H

<400> SEQUENCE: 45
attgttggat catattcgtc cacaaaatga ttctgaatta gctgtatcgt caaggcactc        60

<210> SEQ ID NO 46
<211> LENGTH: 13
<212> TYPE: DNA
<213> ORGANISM: Artificial Sequence
<220> FEATURE:
<223> OTHER INFORMATION: Primer-L

<400> SEQUENCE: 46
cttgtggtag ttg                                                          13
```

<210> SEQ ID NO 47
<211> LENGTH: 13
<212> TYPE: DNA
<213> ORGANISM: Artificial Sequence
<220> FEATURE:
<223> OTHER INFORMATION: Probe-MUT

<400> SEQUENCE: 47
agctgctggc gta                                                        13

<210> SEQ ID NO 48
<211> LENGTH: 13
<212> TYPE: DNA
<213> ORGANISM: Artificial Sequence
<220> FEATURE:
<223> OTHER INFORMATION: Probe-WT

<400> SEQUENCE: 48
agctggtggc gta                                                        13

<210> SEQ ID NO 49
<211> LENGTH: 60
<212> TYPE: DNA
<213> ORGANISM: Artificial Sequence
<220> FEATURE:
<223> OTHER INFORMATION: Primer-H

<400> SEQUENCE: 49
attgttggat catattcgtc cacaaaatga ttctgaatta gctgtatcgt caaggcactc     60

<210> SEQ ID NO 50
<211> LENGTH: 13
<212> TYPE: DNA
<213> ORGANISM: Artificial Sequence
<220> FEATURE:
<223> OTHER INFORMATION: Primer-L

<400> SEQUENCE: 50
cttgtggtag ttg                                                        13

<210> SEQ ID NO 51
<211> LENGTH: 13
<212> TYPE: DNA
<213> ORGANISM: Artificial Sequence
<220> FEATURE:
<223> OTHER INFORMATION: Probe-MUT

<400> SEQUENCE: 51
agctgatggc gta                                                        13

<210> SEQ ID NO 52
<211> LENGTH: 13
<212> TYPE: DNA
<213> ORGANISM: Artificial Sequence
<220> FEATURE:
<223> OTHER INFORMATION: Probe-WT

<400> SEQUENCE: 52
agctggtggc gta                                                        13

<210> SEQ ID NO 53
<211> LENGTH: 60
<212> TYPE: DNA
<213> ORGANISM: Artificial Sequence
<220> FEATURE:

<223> OTHER INFORMATION: Primer-H

<400> SEQUENCE: 53
aagaccctag ccttagataa aactgagcaa gaggctttgg agtatttcat gaaacaaatg    60

<210> SEQ ID NO 54
<211> LENGTH: 100
<212> TYPE: DNA
<213> ORGANISM: Artificial Sequence
<220> FEATURE:
<223> OTHER INFORMATION: Sequence fragment of PIK3CA

<400> SEQUENCE: 54
gaaagaccct agccttagat aaaactgagc aagaggcttt ggagtatttc atgaaacaaa    60
tgaatgatgc acatcatggt ggctggacaa caaaaatgga                         100

<210> SEQ ID NO 55
<211> LENGTH: 14
<212> TYPE: DNA
<213> ORGANISM: Artificial Sequence
<220> FEATURE:
<223> OTHER INFORMATION: MUT-probe

<400> SEQUENCE: 55
ccaccatgac gtgc                                                     14

<210> SEQ ID NO 56
<211> LENGTH: 16
<212> TYPE: DNA
<213> ORGANISM: Artificial Sequence
<220> FEATURE:
<223> OTHER INFORMATION: Primer-L

<400> SEQUENCE: 56
catttttgtt gtccag                                                   16

<210> SEQ ID NO 57
<211> LENGTH: 14
<212> TYPE: DNA
<213> ORGANISM: Artificial Sequence
<220> FEATURE:
<223> OTHER INFORMATION: WT-probe

<400> SEQUENCE: 57
ccaccatgat gtgc                                                     14

<210> SEQ ID NO 58
<211> LENGTH: 16
<212> TYPE: DNA
<213> ORGANISM: Artificial Sequence
<220> FEATURE:
<223> OTHER INFORMATION: WT-probe

<400> SEQUENCE: 58
ctctgaaatc actgag                                                   16

<210> SEQ ID NO 59
<211> LENGTH: 12
<212> TYPE: DNA
<213> ORGANISM: Artificial Sequence
<220> FEATURE:
<223> OTHER INFORMATION: Primer-L

<400> SEQUENCE: 59
ctacacgaga tc                                                       12

<210> SEQ ID NO 60
<211> LENGTH: 16
<212> TYPE: DNA
<213> ORGANISM: Artificial Sequence
<220> FEATURE:
<223> OTHER INFORMATION: MUT-probe

<400> SEQUENCE: 60
tctctaaaat cactga                                                          16

<210> SEQ ID NO 61
<211> LENGTH: 111
<212> TYPE: DNA
<213> ORGANISM: Artificial Sequence
<220> FEATURE:
<223> OTHER INFORMATION: Fragment of PIK3CA

<400> SEQUENCE: 61
ttctacacga gatcctctct ctgaaatcac tgagcaggag aaagattttc tatggagtca          60
caggtaagtg ctaaaatgga gattctctgt ttcttttct ttattacaga a                  111

<210> SEQ ID NO 62
<211> LENGTH: 60
<212> TYPE: DNA
<213> ORGANISM: Artificial Sequence
<220> FEATURE:
<223> OTHER INFORMATION: Primer-L

<400> SEQUENCE: 62
ctgtaataaa gaaaagaaa cagagaatct ccattttagc acttacctgt gactccatag          60

<210> SEQ ID NO 63
<211> LENGTH: 38
<212> TYPE: DNA
<213> ORGANISM: Artificial Sequence
<220> FEATURE:
<223> OTHER INFORMATION: Primer-H (beta-1)

<400> SEQUENCE: 63
ctgagcaaga ggctttggag tatttcatga aacaaatg                                  38

<210> SEQ ID NO 64
<211> LENGTH: 60
<212> TYPE: DNA
<213> ORGANISM: Artificial Sequence
<220> FEATURE:
<223> OTHER INFORMATION: Primer-H (beta-2)

<400> SEQUENCE: 64
tagccttaga taaaactgag caagaggctt tggagtattt catgaaacaa atgaatgatg          60

<210> SEQ ID NO 65
<211> LENGTH: 100
<212> TYPE: DNA
<213> ORGANISM: Artificial Sequence
<220> FEATURE:
<223> OTHER INFORMATION: Fragment of PIK3CA

<400> SEQUENCE: 65
cctagcctta gataaaactg agcaagaggc tttggagtat tcatgaaac aaatgaatga          60 tgcacatcat ggtggctgga caacaaaaat ggattggatc                              100

<210> SEQ ID NO 66

-continued

```
<211> LENGTH: 15
<212> TYPE: DNA
<213> ORGANISM: Artificial Sequence
<220> FEATURE:
<223> OTHER INFORMATION: MUT-Probe

<400> SEQUENCE: 66
ccaccatgac gtgca                                                          15

<210> SEQ ID NO 67
<211> LENGTH: 18
<212> TYPE: DNA
<213> ORGANISM: Artificial Sequence
<220> FEATURE:
<223> OTHER INFORMATION: Primer-L

<400> SEQUENCE: 67
tccaatccat ttttgttg                                                       18

<210> SEQ ID NO 68
<211> LENGTH: 15
<212> TYPE: DNA
<213> ORGANISM: Artificial Sequence
<220> FEATURE:
<223> OTHER INFORMATION: WT-probe

<400> SEQUENCE: 68
ccaccatgat gtgca                                                          15

<210> SEQ ID NO 69
<211> LENGTH: 3207
<212> TYPE: DNA
<213> ORGANISM: Homo sapiens

<400> SEQUENCE: 69
atgcctccac gaccatcatc aggtgaactg tggggcatcc acttgatgcc cccaagaatc           60
ctagtagaat gtttactacc aaatggaatg atagtgactt tagaatgcct ccgtgaggct          120
acattaataa ccataaagca tgaactattt aaagaagcaa gaaaataccc cctccatcaa          180
cttcttcaag atgaatcttc ttacattttc gtaagtgtta ctcaagaagc agaaagggaa          240
gaattttttg atgaaacaag acgactttgt gaccttcggc ttttttcaacc cttttttaaaa        300 gtaattgaac cagtaggcaa ccgtgaagaa aagatcctca atcgagaaat tggttttgct          360
atcggcatgc cagtgtgtga atttgatatg gttaaagatc cagaagtaca ggacttccga          420
agaaatattc tgaacgtttg taaagaagct gtggatctta gggacctcaa ttcacctcat          480
agtagagcaa tgtatgtcta cctccaaat gtagaatctt caccagaatt gccaaagcac          540
atatataata aattagataa agggcaaata atagtggtga tctgggtaat agtttctcca          600
aataatgaca agcagaagta tactctgaaa atcaaccatg actgtgtacc agaacaagta          660
attgctgaag caatcaggaa aaaaactcga agtatgttgc tatcctctga caactaaaa           720 ctctgtgttt tagaatatca gggcaagtat attttaaaag tgtgtggatg tgatgaatac          780
ttcctagaaa aatatcctct gagtcagtat aagtatataa aagctgtat aatgcttggg          840 aggatgccca atttgatgtt gatggctaaa gaaagccttt attctcaact gccaatggac          900
tgttttacaa tgccatctta ttccagacgc atttccacag ctacaccata tatgaatgga          960
gaaacatcta caaatccct tgggttata aatagtgcac tcagaataaa aattctttgt          1020
gcaacctacg tgaatgtaaa tattcgagac attgataaga tctatgttcg aacaggtatc          1080
taccatggag gagaaccctt atgtgacaat gtgaacactc aaagagtacc ttgttccaat          1140
```

```
cccaggtgga atgaatggct gaattatgat atatacattc ctgatcttcc tcgtgctgct    1200
cgactttgcc tttccatttg ctctgttaaa ggccgaaagg gtgctaaaga ggaacactgt    1260
ccattggcat ggggaaatat aaacttgttt gattacacag acactctagt atctggaaaa    1320
atggctttga atctttggcc agtacctcat ggattagaag atttgctgaa ccctattggt    1380
gttactggat caaatccaaa taaagaaact ccatgcttag agttggagtt tgactggttc    1440
agcagtgtgg taaagttccc agatatgtca gtgattgaag agcatgccaa ttggtctgta    1500
tcccgagaag caggatttag ctattcccac gcaggactga gtaacagact agctagagac    1560
aatgaattaa gggaaaatga caagaacag ctcaaagcaa tttctacacg agatcctctc    1620
tctgaaatca ctgagcagga gaagattttt ctatggagtc acagacacta ttgtgtaact    1680
atccccgaaa ttctacccaa attgcttctg tctgttaaat ggaattctag agatgaagta    1740
gcccagatgt attgcttggt aaaagattgg cctccaatca aacctgaaca ggctatggaa    1800
cttctggact gtaattaccc agatcctatg gttcgaggtt ttgctgttcg gtgcttggaa    1860
aaatatttaa cagatgacaa actttctcag tatttaattc agctagtaca ggtcctaaaa    1920
tatgaacaat atttggataa cttgcttgtg agattttttac tgaagaaagc attgactaat    1980
caaaggattg ggcactttttt cttttggcat ttaaaatctg agatgcacaa taaaacagtt    2040
agccagaggt ttggcctgct tttggagtcc tattgtcgtg catgtgggat gtatttgaag    2100
cacctgaata ggcaagtcga ggcaatggaa aagctcatta acttaactga cattctcaaa    2160
caggagaaga aggatgaaac acaaaaggta cagatgaagt ttttagttga gcaaatgagg    2220
cgaccagatt tcatggatgc tctacagggc tttctgtctc ctctaaaccc tgctcatcaa    2280
ctaggaaacc tcaggcttga agagtgtcga attatgtcct ctgcaaaaag gccactgtgg    2340
ttgaattggg agaacccaga catcatgtca gagttactgt ttcagaacaa tgagatcatc    2400
tttaaaaatg gggatgattt acggcaagat atgctaacac ttcaaattat tcgtattatg    2460
gaaaatatct ggcaaaatca aggtcttgat cttcgaatgt taccttatgg ttgtctgtca    2520
atcggtgact gtgtgggact tattgaggtg gtgcgaaatt ctcacactat tatgcaaatt    2580
cagtgcaaag gcggcttgaa aggtgcactg cagttcaaca gccacacact acatcagtgg    2640
ctcaaagaca gaacaaaagg agaaatatat gatgcagcca ttgacctgtt tacacgttca    2700
tgtgctggat actgtgtagc taccttcatt ttgggaattg gagatcgtca caatagtaac    2760
atcatggtga agacgatgg acaactgttt catatagatt ttggacactt tttggatcac    2820
aagaagaaaa aatttggtta taacgagaaa cgtgtgccat tgttttttgac acaggatttc    2880 ttaatagtga ttagtaaagg agcccaagaa tgcacaaaga caagagaatt tgagaggttt    2940
caggagatgt gttacaaggc ttatctagct attcgacagc atgccaatct cttcataaat    3000
cttttctcaa tgatgcttgg ctctggaatg ccagaactac aatcttttga tgacattgca    3060
tacattcgaa agaccctagc cttagataaa actgagcaag aggctttgga gtatttcatg    3120
aaacaaatga atgatgcaca tcatggtggc tggacaacaa aaatggattg gatcttccac    3180
acaattaaac agcatgcatt gaactga                                        3207
```

<210> SEQ ID NO 70
<211> LENGTH: 2301
<212> TYPE: DNA
<213> ORGANISM: Homo sapiens

<400> SEQUENCE: 70

```
atggcggcgc tgagcggtgg cgtggtggc ggcgcggagc cgggccaggc tctgttcaac      60
ggggacatgg agcccgaggc cggcgccggc gccggcgccg cggcctcttc ggctgcggac     120
cctgccattc cggaggaggt gtggaatatc aaacaaatga ttaagttgac acaggaacat    180
atagaggccc tattggacaa atttggtggg gagcataatc caccatcaat atatctggag    240
gcctatgaag aatacaccag caagctagat gcactccaac aaagagaaca acagttattg    300
gaatctctgg ggaacggaac tgattttttct gtttctagct ctgcatcaat ggataccgtt    360
acatcttctt cctcttctag cctttcagtg ctaccttcat ctctttcagt ttttcaaaat    420
cccacagatg tggcacggag caaccccaag tcaccacaaa aacctatcgt tagagtcttc    480
ctgcccaaca aacagaggac agtggtacct gcaaggtgtg gagttacagt ccgagacagt    540
ctaaagaaag cactgatgat gagaggtcta atcccagagt gctgtgctgt ttacagaatt    600
caggatggag agaagaaacc aattggttgg gacactgata tttcctggct tactggagaa    660
gaattgcatg tggaagtgtt ggagaatgtt ccacttacaa cacacaactt tgtacgaaaa    720
acgttttca ccttagcatt tgtgactttt tgtcgaaagc tgcttttcca gggtttccgc    780
tgtcaaacat gtggttataa atttcaccag cgttgtagta cagaagttcc actgatgtgt    840
gttaattatg ccaacttga tttgctgttt gtctccaagt tctttgaaca ccacccaata    900
ccacaggaag aggcgtcctt agcagagact gccctaacat ctggatcatc cccttccgca    960
cccgcctcgg actctattgg gccccaaatt ctcaccagtc cgtctccttc aaaatccatt   1020
ccaattccac agcccttccg accagcagat gaagatcatc gaaatcaatt tgggcaacga   1080
gaccgatcct catcagctcc caatgtgcat ataaacacaa tagaacctgt caatattgat   1140
gacttgatta gagaccaagg atttcgtggt gatggaggat caaccacagg tttgtctgct   1200
accccccctg cctcattacc tggctcacta actaacgtga aagccttaca gaatctccaa   1260
ggacctcagc gagaaaggaa gtcatcttca tcctcagaag acaggaatcg aatgaaaaca   1320
cttggtagac gggactcgag tgatgattgg gagattcctg atgggcagat tacagtggga   1380
caaagaattg gatctggatc atttggaaca gtctacaagg gaaagtggca tggtgatgtg   1440
gcagtgaaaa tgttgaatgt gacagcacct acacctcagc agttacaagc cttcaaaaat   1500
gaagtaggag tactcaggaa aacacgacat gtgaatatcc tactcttcat gggctattcc   1560
acaaagccac aactggctat tgttacccag tggtgtgagg gctccagctt gtatcaccat   1620
ctccatatca ttgagaccaa atttgagatg atcaaactta tagatattgc acgacagact   1680
gcacagggca tggattactt acacgccaag tcaatcatcc acagagacct caagagtaat   1740
aatatatttc ttcatgaaga cctcacagta aaaataggtg attttggtct agctacagtg   1800
aaatctcgat ggagtgggtc ccatcagttt gaacagttgt ctggatccat tttgtggatg   1860
gcaccagaag tcatcagaat gcaagataaa aatccataca gctttcagtc agatgtatat   1920
gcatttggaa ttgttctgta tgaattgatg actggacagt taccttattc aaacatcaac   1980
aacagggacc agataatttt tatggtggga cgaggatacc tgtctccaga tctcagtaag   2040
gtacggagta actgtccaaa agccatgaag agattaatgg cagagtgcct caaaaagaaa   2100
agagatgaga gaccactctt tccccaaatt ctcgcctcta ttgagctgct ggcccgctca   2160
ttgccaaaaa ttcaccgcag tgcatcagaa ccctccttga tcgggctgg tttccaaaca   2220
gaggatttta gtctatatgc ttgtgcttct ccaaaaacac ccatccaggc agggggatat   2280
ggtgcgtttc ctgtccactg a                                              2301
```

```
<210> SEQ ID NO 71
<211> LENGTH: 3633
<212> TYPE: DNA
<213> ORGANISM: Homo sapiens

<400> SEQUENCE: 71
atgcgaccct ccgggacggc cggggcagcg ctcctggcgc tgctggctgc gctctgcccg    60
gcgagtcggg ctctggagga aaagaaagtt tgccaaggca cgagtaacaa gctcacgcag   120
ttgggcactt ttgaagatca ttttctcagc ctccagagga tgttcaataa ctgtgaggtg   180
gtccttggga atttggaaat tacctatgtg cagaggaatt atgatctttc cttcttaaag   240
accatccagg aggtggctgg ttatgtcctc attgccctca acacagtgga gcgaattcct   300
ttggaaaacc tgcagatcat cagaggaaat atgtactacg aaaattccta tgccttagca   360
gtcttatcta actatgatgc aaataaaacc ggactgaagg agctgcccat gagaaattta   420
caggaaatcc tgcatggcgc cgtgcggttc agcaacaacc ctgccctgtg caacgtggag   480
agcatccagt ggcgggacat agtcagcagt gactttctca gcaacatgtc gatggacttc   540
cagaaccacc tgggcagctg ccaaaagtgt gatccaagct gtcccaatgg agctgctgg    600 ggtgcaggag aggagaactg ccagaaactg accaaaatca tctgtgccca gcagtgctcc   660
gggcgctgcc gtggcaagtc ccccagtgac tgctgccaca accagtgtgc tgcaggctgc   720
acaggccccc gggagagcga ctgcctggtc tgccgcaaat ccgagacga gccacgtgc    780 aaggacacct gccccccact catgctctac aaccccacca cgtaccagat ggatgtgaac   840
cccgagggca aatacagctt tggtgccacc tgcgtgaaga gtgtccccg taattatgtg   900 gtgacagatc acggctcgtg cgtccgagcc tgtggggccg acagctatga gatggaggaa   960
gacggcgtcc gcaagtgtaa gaagtgcgaa gggccttgcc gcaaagtgtg taacggaata  1020
ggtattggtg aatttaaaga ctcactctcc ataaatgcta cgaatattaa acacttcaaa  1080
aactgcacct ccatcagtgg cgatctccac atcctgccgg tggcatttag gggtgactcc  1140
ttcacacata ctcctcctct ggatccacag gaactggata ttctgaaaac cgtaaaggaa  1200
atcacagggt ttttgctgat tcaggcttgg cctgaaaaca ggacggacct ccatgccttt  1260
gagaacctag aaatcatacg cggcaggacc aagcaacatg gtcagttttc tcttgcagtc  1320
gtcagcctga acataacatc cttgggatta cgctccctca aggagataag tgatggagat  1380
gtgataattt caggaaacaa aaatttgtgc tatgcaaata atataaactg gaaaaaactg  1440
tttgggacct ccggtcagaa aaccaaaatt ataagcaaca gaggtgaaaa cagctgcaag  1500
gccacaggcc aggtctgcca tgccttgtgc tcccccgagg ctgctgggg cccggagccc  1560 agggactgcg tctcttgccg gaatgtcagc cgaggcaggg aatgcgtgga caagtgcaac  1620
cttctggagg tgagccaagg gagtttgtg gagaactctg agtgcataca gtgccaccca  1680
gagtgcctgc ctcaggccat gaacatcacc tgcacaggac ggggaccaga caactgtatc  1740
cagtgtgccc actacattga cggccccac tgcgtcaaga cctgcccggc aggagtcatg  1800
ggagaaaaca caccctggt ctggaagtac gcagacgccg ccatgtgtg ccacctgtgc  1860 catccaaact gcacctacgg atgcactggg ccaggtcttg aaggctgtcc aacgaatggg  1920
cctaagatcc cgtccatcgc cactgggatg gtggggcc tcctcttgct gctggtggtg  1980
gccctgggga tcggcctctt catgcgaagg cgccacatcg ttcggaagcg cacgctgcgg  2040
aggctgctgc aggagaggga gcttgtggag cctcttacac ccagtggaga agctcccaac  2100
caagctctct tgaggatctt gaaggaaact gaattcaaaa agatcaaagt gctgggctcc  2160
```

-continued

```
ggtgcgttcg gcacggtgta taagggactc tggatcccag aaggtgagaa agttaaaatt    2220
cccgtcgcta tcaaggaatt aagagaagca acatctccga aagccaacaa ggaaatcctc    2280
gatgaagcct acgtgatggc cagcgtggac aaccccacg tgtgccgcct gctgggcatc     2340
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaatttt acacagaatc tatacccacc agagtgatgt ctggagctac    2700
ggggtgactg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc     2940 attcagggg atgaaagaat gcatttgcca agtcctacag actccaactt ctaccgtgcc     3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg gcaaccccga gtatctcaac    3420
actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                 3633
```

<210> SEQ ID NO 72
<211> LENGTH: 567
<212> TYPE: DNA
<213> ORGANISM: Homo sapiens

<400> SEQUENCE: 72

```
atgactgaat ataaacttgt ggtagttgga gctggtggcg taggcaagag tgccttgacg      60
atacagctaa ttcagaatca ttttgtggac gaatatgatc caacaataga ggattcctac    120
aggaagcaag tagtaattga tgaaaacc tgtctcttgg atattctcga cacagcaggt      180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggactag caagaagtta tggaattcct    420
tttattgaaa catcagcaaa gacaagacag ggtgttgatg atgccttcta tacattagtt    480
cgagaaattc gaaacataa agaaaagatg agcaaagatg gtaaaagaa gaaaagaag     540 tcaaagacaa agtgtgtaat tatgtaa                                        567
```